United States Patent
Crauste et al.

(10) Patent No.: US 12,195,437 B2
(45) Date of Patent: Jan. 14, 2025

(54) LIPOPHENOLIC FLAVONOID DERIVATIVES USEFUL TO REDUCE CARBONYL AND OXIDATIVE STRESSES (COS)

(71) Applicants: Centre National de la Recherche Scientifique (CNRS), Paris (FR); Universite De Montpellier, Montpellier (FR); Ecole Nationale Superieure de Chimie, Montpellier (FR); Institut National de la Sante et de la Recherche Medicale (INSERM), Paris (FR)

(72) Inventors: Céline Crauste, Montpellier (FR); Espérance Moine, Montpellier (FR); Philippe Brabet, Matelles (FR); Thierry Durand, Montpellier (FR); Joseph Vercauteren, Castelnau le Lez (FR)

(73) Assignees: Centre National de la Recherche Scientifique (CNRS) (FR); Universite De Montpellier (FR); Ecole Nationale Superieure de Chimie (FR); Institut National de la Sante et de la Recherche Medicale (INSERM) (FR)

( * ) Notice: Subject to any disclaimer, the term of this patent is extended or adjusted under 35 U.S.C. 154(b) by 899 days.

(21) Appl. No.: 17/259,733

(22) PCT Filed: Jul. 12, 2019

(86) PCT No.: PCT/EP2019/068872
§ 371 (c)(1),
(2) Date: Jan. 12, 2021

(87) PCT Pub. No.: WO2020/012003
PCT Pub. Date: Jan. 16, 2020

(65) Prior Publication Data
US 2021/0139447 A1 May 13, 2021

(30) Foreign Application Priority Data

Jul. 13, 2018 (EP) .................................. 18305957

(51) Int. Cl.
*C07D 311/62* (2006.01)
*A23L 33/00* (2016.01)
(Continued)

(52) U.S. Cl.
CPC ............ *C07D 311/62* (2013.01); *A23L 33/10* (2016.08); *A23L 33/40* (2016.08); *A61P 39/06* (2018.01); *A23V 2002/00* (2013.01)

(58) Field of Classification Search
None
See application file for complete search history.

(56) References Cited

FOREIGN PATENT DOCUMENTS

| JP | 2008239504 A | 10/2008 |
|---|---|---|
| WO | 2010129138 A2 | 11/2010 |

(Continued)

OTHER PUBLICATIONS

Ahmed et al. Role of fatty acid chain length on the induction of apoptosis by newly synthesized catechin derivatives, Chemico-Biological Interactions, vol. 185, Issue 3, 2010, pp. 182-188, ISSN 0009-2797, doi.org/10.1016/j.cbi.2010.02.045 (Year: 2010).*

(Continued)

*Primary Examiner* — Jeffrey S Lundgren
*Assistant Examiner* — Anthony Joseph Seitz
(74) *Attorney, Agent, or Firm* — Lerner David LLP

(57) ABSTRACT

The invention relates to compound of formula (I): in particular flavonoid derivatives (quercetin and catechin derivatives), for use in the prevention and/or the treatment of a disease or disorder involving both carbonyl and oxidative stresses.

(Continued)

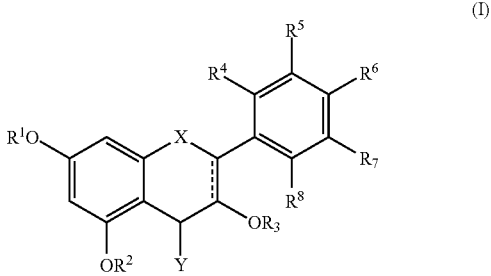

(I)

18 Claims, 5 Drawing Sheets

(51) Int. Cl.
  *A23L 33/10* (2016.01)
  *A61P 39/06* (2006.01)

(56) References Cited

FOREIGN PATENT DOCUMENTS

| WO | WO-2012032509 A2 | * | 3/2012 | ........... A61K 31/401 |
|---|---|---|---|---|
| WO | 2014049561 A2 | | 4/2014 | |
| WO | WO-2015162265 A1 | * | 10/2015 | .............. A61P 29/00 |
| WO | 2019008537 A1 | | 1/2019 | |
| WO | 2019008537 A9 | | 2/2020 | |

OTHER PUBLICATIONS

Panche et al., Flavonoids: an overview. J Nutr Sci. Dec. 29, 2016 (Year: 2016).*
The red wine phenolics trans-resveratrol and quercetin block human platelet aggregation and eicosanoid synthesis: implications for protection against coronary heart disease. Clin Chim Acta. Mar. 31, 1995;235(2):207-19 (Year: 1995).*
Kim et al., Effect of phloroglucinol on oxidative stress and inflammation. Food Chem Toxicol. Oct. 2010;48(10):2925-33 (Year: 2010).*
Gatto et al., Antimicrobial and Anti-Lipase Activity of Quercetin and its C2-C16 3-O-Acyl-Esters, Bioorganic & Medicinal Chemistry, vol. 10, Issue 2, 2002, pp. 269-272 (Year: 2002).*
Allikmets, R. et al., "A photoreceptor cell-specific ATP-binding transporter gene (ABCR) is mutated in recessive Stargardt macular dystrophy" Nature Publishing Group, Mar. 1997, pp. 236-246, vol. 15.
Berge S. M. et al., "Pharmaceutical Salts", Journal of Pharmaceutical Sciences, Jan. 1977, pp. 1-19, vol. 66, No. 1.
Database CA, Golyshin, P. N. et al.: "Preparation of fluorescent probe-based reactome array for detection, immobilization and isolation of enzymes" Sep. 2010, Chemical Abstracts Service, Columbus, Ohio, XP002785561, pp. 1-5.
Database CA, Nimura. Y.: "Polyphenols as fibroblast cell activators, and foods and cosmetics containing them", Nov. 2006, Chemical Abstracts Service, Columbus, Ohio, XP002785562, pp. 1-4.
Feng, J. et al., "Decoration of gemini alkyl O-glucosides based vesicles by electrostatic deposition of sodium carboxymethyl cellulose: Mechanism, structure and improved stability", Food Hydrocolloids, Mar. 2016, pp. 284-297, vol. 58, Elsevier Ltd.
International Search Report for Application No. PCT/EP2019/068872 mailed Aug. 29, 2019, pp. 1-5.
Khlebnikov, A. I. et al., "Improved quantitative structure-activity relationship models to predict antioxidant activity of flavonoids in chemical, enzymatic, and cellular systems", Bioorganic & Medicinal Chemistry, Nov. 2006, pp. 1749-1770, vol. 15, Elsevier Ltd.
Lin S. F. et al., "Synthesis and structure-activity relationship of 3-0-acylated (-)-epigallocatechins as 5@a-reductase inhibitors" European Journal of Medicinal Chemistry, Oct. 2010, pp. 6068-6076, vol. 45, Elsevier Masson SAS.
Parish C. A. et al., "Isolation and one-step preparation of A2E and iso-A2E, fluorophores from human retinal pigment epithelium" Proceedings of the National Academy of Sciences, Dec. 1998, pp. 14609-14613, vol. 95.
Sears A. E. et al., "Towards Treatment of Stargardt Disease: Workshop Organized and Sponsored by the Foundation Fighting Blindness" Translational Vision Science and Technology, Sep. 2017, pp. 1-12, vol. 6, No. 5, Article 6.
Sparrow, J. R. et al. "The Bisretinoids of Retinal Pigment Epithelium" National Institutes of Health, Available in PMC Mar. 2013, pp. 1-32, vol. 31(2), Elsevier Ltd.
Temkitthawon, P. et al., "Kaempferia parviflora, a plant used in traditional medicine to enhance sexual performance contains large amounts of low affinity PDE5 inhibitors", Journal of Ethnopharmacology, Aug. 2011, pp. 1437-1441, vol. 137, Elsevier Ireland Ltd.
Moine, E. et al., "New lipophenols prevent carbonyl and oxidative stresses involved in macular degeneration ," Free Radical Biology and Medicine, Oct. 28, 2020, vol. 162 (2021), pp. 367-382.
Crauste, C. et al., "Synthesis and Evaluation of Polyunsaturated Fatty Acid-Phenol Conjugates as Anti-Carbonyl-Stress Lipophenols," European Journal of Organic Chemistry, Jul. 2014, pp. 4548-4561.
Dell'Albani, Paola et al. "Quercetin derivatives as potent inducers of selective cytotoxicity in glioma cells", European journal of pharmaceutical sciences : official journal of the European Federation for Pharmaceutical Sciences, vol. 101 (Jan. 2017): 56-65. doi:10.1016/j.ejps.2017.01.036.
Shibnath Ghosal, et al., "Xanthone and flavonol constituents of Swertia hookeri", Phytochemistry, vol. 19, Issue 1, Jan. 1980, pp. 123-126, ISSN 0031-9422, https://doi.org/10.1016/0031-9422(80)85027-8.
B Pignataro, et al., "From micro- to nanometric scale patterning by Langmuir-Blodgett technique", Materials Science and Engineering: C, vol. 22, Issue 2, Dec. 2002, pp. 177-181, ISSN 0928-4931, https://doi.org/10.1016/S0928-4931(02)00168-6.
Gatto, Maria Teresa et al., "Antimicrobial and anti-lipase activity of quercetin and its C2-C16 3-O-acyl-esters", Bioorganic & medicinal chemistry vol. 10, 2 (Feb. 2002): 269-72. doi: 10.1016/s0968-0896(01)00275-9.

* cited by examiner

LIPOPHENOLIC FLAVONOID DERIVATIVES USEFUL TO REDUCE CARBONYL AND OXIDATIVE STRESSES (COS)

CROSS-REFERENCE TO RELATED APPLICATIONS

The present application is a national phase entry under 35 U.S.C. § 371 of International Application No. PCT/EP2019/068872, filed Jul. 12, 2019, which claims priority from European Patent Application No. 18305957.5 filed Jul. 13, 2018, all of which are incorporated herein by reference.

FIELD OF THE INVENTION

The present invention relates to lipophenolic derivatives, in particular flavonoid derivatives, able to prevent or reduce both carbonyl and oxidative stresses (COS), and their uses in therapeutic and non-therapeutic applications, in particular in the prevention and/or treatment of retinal pathologies and neurodegenerative disease.

BACKGROUND OF THE INVENTION

It is known from the art that oxidative stress, resulting from an overproduction of reactive oxygen species (ROS) within cells or in the extracellular matrix, leads to an important damage to key cellular proteins, lipids and DNA. In parallel, reactive carbonyl species are involved in glycation and cross-linking reactions of proteins and thus affect as well, cellular viability leading to tissue injury.

So, these two carbonyl and oxidative stress (COS) mechanisms play a crucial role in aging-associated pathologies such as age-related macular degeneration (AMD, dry form) or genetic macular degeneration (Stargardt) which is a hereditary retinal dystrophia linked to mutations of a gene encoding a lipidic (retinal) carrier of ATP-Binding Cassette subtype A4 (ABCA4) (Allikmets et al., 1997), or neurodegenerative diseases. Epidemiological studies of the last two decades show that AMD is one of the first diseases that cause mostly central and irreversible visual loss in old population of occidental countries. Because the physiopathology of the disease has been poorly understood in the past, there is no currently available treatment in the market to stop retinal degeneration, especially in the dry AMD (the most common form 80-85%).

Recent advances in the understanding of the Stargardt physiopathology, show that therapeutic strategies for this rare disease (incidence of 1:8000 to 10,000) may be proposed for both diseases (A. E. Sears et al. *Transl Vis Sci Technol* 2017, 6, p. 6). It is now known that carbonyl and oxidative stress (COS) mechanisms are responsible for accumulation in retinal pigment epithelium (RPE) of a toxic bis-retinoid conjugate called A2E (its photoisomers and its oxidized metabolites).

Pathologic A2E biosynthesis occurs when molecules of trans-retinal, a reactive carbonyl specie, rather than undergoing reduction to retinol, upon their removal from the photoreceptor to RPE cells, accumulate abnormally (because of age or genetic mutation) and react with phosphatidylethanolamine through a dual carbonyl and oxidative stress (COS) (J. R. Sparrow et al. *Prog. Retin. Eye Res.* 2012, 31, 121-135).

These two carbonyl and oxidative stress (COS) mechanisms are also involved in biological, cellular and/or physiological processes such as food oxidation, ageing and sporting activities.

So there is still a need for providing compounds able to act as potent antioxidant and to trap the main carbonyl stressor trans-retinal, to reduce A2E formation and to slow down progression of the diseases. Such new compounds anti-COS, able to prevent or reduce both carbonyl and oxidative stresses (COS), would be of great interest in particular in the prevention and/or treatment of retinal pathologies (e.g macular degeneration) and neurodegenerative disease.

Phloroglucinol derivatives were previously disclosed as being able to reduce carbonyl stress in RPE cells (WO 2015/162265). Unfortunately, these compounds were not able to reduce ROS (reactive oxygen species) formed by $H_2O_2$ treatment in cellular assay and thus were not efficient to reduce main toxic mechanism involved in retina dystrophy: the oxidative stress.

Surprisingly, the applicant developed new lipophenolic flavonoid derivatives and demonstrated their efficiency on both carbonyl and oxidative stresses (COS). Such lipophenolic derivatives having this complementary action are expected to be more efficient in the prevention and/or treatment of diseases or disorders involving these both mechanisms.

The lipophenolic flavonoids derivatives of the invention comprise three cycles wherein the third one is in position 2, which distinguishes from the isoflavone compounds as disclosed in the prior art WO2014/049561, wherein the third cycle is in position 3 as figured in the following general structure:

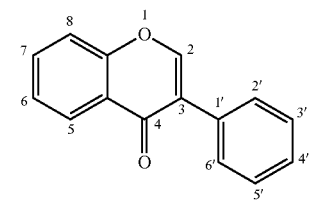

SUMMARY OF THE INVENTION

A first object of the invention is a compound of formula (I):

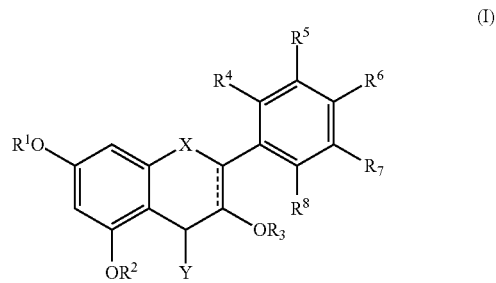

wherein
$R^1$ and $R^2$ are identical or different and are each independently selected from the group consisting of H, ($C_1$-$C_6$)alkyl, —C(O)—($C_{11}$-$C_{21}$)alkyl or —C(O)—($C_{11}$-$C_{21}$)alkenyl,
$R^3$ is selected from the group consisting of ($C_1$-$C_6$)alkyl, —C(O)—($C_{11}$-$C_{21}$)alkyl or —C(O)—($C_{11}$-$C_{21}$)alkenyl, $R^4$ to $R^8$ are identical or different and are each independently selected from the group consisting of H, OH, O($C_1$-$C_6$)alkyl, —OC(O)—($C_{11}$-$C_{21}$)alkyl or —OC(O)—($C_{11}$-$C_{21}$)alkenyl, X is selected from the group consisting of O, S, $CH_2$ or NH, Y is absent or oxo group, ═══ is simple or double bond, or its pharmaceutically acceptable salts, racemates, diastereoisomers, enantiomers or mixtures thereof, for use in the prevention and/or the treatment of a disease or disorder involving both carbonyl and oxidative stresses.

The present invention also concerns a compound of formula (I)

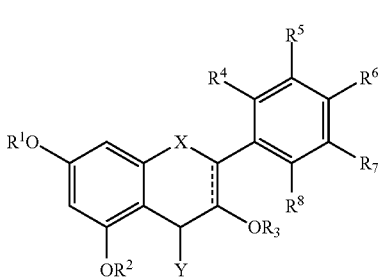

(I)

wherein X, Y, ═══ and $R^1$ to $R^8$ are as defined above, provided that one of $R^1$ or $R^2$ is H and the other is not H, or its pharmaceutically acceptable salts, racemates, diastereoisomers, enantiomers or mixtures thereof.

Another object of the present invention is a composition, in particular a pharmaceutical composition comprising, in a pharmaceutically acceptable vehicle, at least one compound as defined just above.

DETAILED DESCRIPTION OF THE INVENTION

The present invention concerns a compound of formula (I):

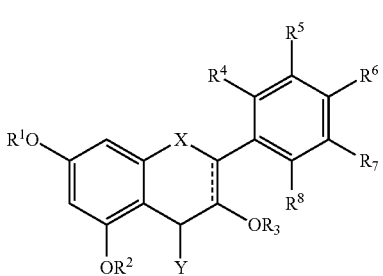

(I)

wherein $R^1$ and $R^2$ are identical or different and are each independently selected from the group consisting of H, ($C_1$-$C_6$)alkyl, —C(O)—($C_{11}$-$C_{21}$)alkyl or —C(O)—($C_{11}$-$C_{21}$)alkenyl, $R^3$ is selected from the group consisting of ($C_1$-$C_6$)alkyl, —C(O)—($C_{11}$-$C_{21}$)alkyl or —C(O)—($C_{11}$-$C_{21}$)alkenyl, $R^4$ to $R^8$ are identical or different and are each independently selected from the group consisting of H, OH, O($C_1$-$C_6$)alkyl, —OC(O)—($C_{11}$-$C_{21}$)alkyl or —OC(O)—($C_{11}$-$C_{21}$)alkenyl, X is selected from the group consisting of O, S, $CH_2$ or NH, Y is absent or oxo group, ═══ is simple or double bond, or its pharmaceutically acceptable salts, racemates, diastereoisomers, enantiomers or mixtures thereof, for use in the prevention and/or the treatment of a disease or disorder involving both carbonyl and oxidative stresses.

The term 'lipophenolic' flavonoids derivatives according to the invention means that the flavonoids compounds of the invention comprise at least one lipidic chain as substituent. So, it means that at least one of the substituents of the cycles of compounds of the formula (I) according to the invention comprises a lipidic chain. In particular, at least one of substituents $R^1$, $R^2$, $R^3$, $R^4$, $R^5$, $R^6$, $R^7$, $R^8$ of the compounds of formula (I) according to the invention is selected from the group consisting of —OC(O)—($C_{11}$-$C_{21}$)alkyl or —OC(O)—($C_{11}$-$C_{21}$)alkenyl.

And the lipophenolic flavonoids derivatives of the present invention are able to deal with both carbonyl and oxidative stresses, for the prevention or treatment of related disorders.

The term 'diseases' and 'disorders' are used interchangeably in the present disclosure.

The term 'treatment' or 'treating' according to the invention means reversing, alleviating, reducing the progression, inhibiting the progress of, or preventing the disorder or condition to which such term applies, or one or more symptoms of such disorder or condition.

According to the present invention, the term "disease or disorder involving both carbonyl and oxidative stress" refers to a disease or disorder which involves abnormal alkylation of important intra or extracellular biological molecules: proteins, nucleic acids, glutathione, phosphatidylethanolamine and many other ones like. This deleterious bond formation being due either to the reaction between nucleophilic functions of these molecules with reactive electrophiles (carbonyl species), thus said the carbonyl stress (leading to glycation or Maillard reactions), or as well as to oxidant reactive oxygen species (ROS), thus said the oxidative stress.

According to the present invention, the disease or disorder involving carbonyl and oxidative stresses may be selected from the group consisting of: inflammatory and infectious diseases, cardiovascular diseases, metabolic diseases, cancer, infertility, retinal pathologies, neuromuscular and muscular diseases, psychiatric diseases and neurodegenerative diseases. In a particular and preferred embodiment, the disease or disorder involving carbonyl and oxidative stresses is selected from the group consisting of retinal pathologies and neurodegenerative disorders.

The term "disorder" also encompasses biochemical, cellular, biological and/or physiological processes in which carbonyl stress and/or oxidative stress are modulated such as food oxidation, ageing or sporting activities.

In the context of the invention, the term "carbonyl stress" is the abnormal metabolism resulting from the enhanced electrophilic reactivity of carbonyl species, said the carbonyl stressors, such as osides (glucose, fructose, and like) and their derivatives (osones, glyoxal, methylglyoxal, glyoxylic acid and like), but also, such as the aldehydes formed upon lipid peroxidation (malondialdehyde, 4-hydroxynonenal=4-HNE, and like). In the context of the invention the term "carbonyl stress" is the abnormal accumulation of endogenous electrophilic carbonyl species such as trans-retinal.

A compound according to the invention has an anti-carbonyl stress activity because is able to efficiently reduce carbonyl stressor toxicity. It could then limit the formation of pathological products such as lipofuscins.

In the context of the invention, the term "oxidative stress" is the result of an abnormal radical oxidation reaction taking place when a ROS is formed upon electron leakage during the respiration process, or when the anti-oxidant enzymatic system of the cells is deficient or not sufficient to reduce normal ROS production. If this occurs for example in the bilayer membranes and in the presence of dioxygen, the alkyl radical oxidizes to the alkylperoxide radical which further reacts by abstracting one proton and one electron to another lipid of the membrane, which starts a chain oxidation reaction. This oxidative stress not only causes new bond formation or the breaking down of the lipids, but also the harmful peroxidation processes, eventually leading to inflammation through the eicosanoid cascade and the release of the cytokines. A compound according to the invention has an anti-oxidative stress activity and is able to scavenge oxidative stressors (ROS) or to activate enzymatic antioxidant responses of the cell, and thus to avoid the formation of the toxic oxidation products and the inflammatory response, to quench any chain oxidation reaction, thus, in case of Stargardt disease, the production of the lipofuscin A2E, and its degradation in toxic oxidized metabolites.

The compound according to the present invention can be in the form of a stereoisomer or a mixture of stereoisomers, such as a mixture of enantiomers, notably a racemic mixture.

The term "stereoisomers" used in this invention refers to configurational stereoisomers and more particularly to optical isomers.

The optical isomers result from the different position in space of substituents or lone pair of electrons on an atom (such as a carbon or sulphur atom) comprising four different substituents (including potentially a lone pair of electron). This atom thus represents a chiral or asymmetric center. Optical isomers that are not mirror images of one another are thus designated as "diastereoisomers," and optical isomers, which are non-superimposable mirror images, are designated as "enantiomers".

An equimolar mixture of two enantiomers of a chiral compound is designated as a racemic mixture or racemate.

For the purpose of the invention, the term "pharmaceutically acceptable" is intended to mean what is useful to the preparation of a pharmaceutical composition, and what is generally safe and non-toxic, for a pharmaceutical use.

The term "pharmaceutically acceptable salts" refers to salts which retain the biological effectiveness and properties of the compounds of the invention and which are not biologically or otherwise undesirable. Pharmaceutically acceptable acid addition salts may be prepared from inorganic and organic acids, while pharmaceutically acceptable base addition salts can be prepared from inorganic and organic bases. For a review of pharmaceutically acceptable salts see Berge, et al. ((1977) "*Pharmacologically acceptable salts*" J. Pharm. Sd, vol. 66, 1). For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, and toluenesulfonic acid and the like.

The term "$(C_1-C_6)$alkyl", as used in the present invention, refers to a straight or branched monovalent saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "$C(O)-(C_{11}-C_{21})$ alkyl" as used in the present invention, refers to an acyl group wherein the $-(C_{11}-C_{21})$ alkyl part is a, linear or branched, saturated alkyl radical.

The term "$C(O)-(C_{11}-C_{21})$ alkenyl" as used in the present invention, refers to an acyl group wherein the $-(C_{11}-C_{21})$ alkenyl part is a, linear or branched, alkyl radical interrupted by one or several double bonds.

The terms "$C(O)-(C_{11}-C_{21})$ alkyl" and "$C(O)-(C_{11}-C_{21})$ alkenyl" corresponds to lipidic chain and are also named fatty acid in the description.

The $-(C_{11}-C_{21})$ alkyl or alkenyl part encompasses a carbon chain having from 11 to 21 carbon atoms, in particular from 12 to 21, preferably from 13 to 21, and even preferably from 15 to 21 carbon atoms.

In a particular embodiment, the lipidic chain comprises $C(O)-(C_{13}-C_{21})$ alkyl or $C(O)-(C_{13}-C_{21})$ alkenyl, preferably $C(O)-(C_{15}-C_{21})$ alkyl or $C(O)-(C_{15}-C_{21})$ alkenyl ---- refers to a single bond or to a double bond.

In a particular embodiment of the present invention, ---- is advantageously a double bond.

In another particular embodiment, X is advantageously an oxygen atom.

In another embodiment, Y is advantageously an oxo group.

In a particular embodiment, ---- is a double bond and X is an oxygen atom. According to another particular embodiment, ---- is a double bond and Y is an oxo group. According to another particular embodiment, X is an oxygen atom and Y is an oxo group.

In a preferred embodiment, ---- is a double bond, X is an oxygen atom and Y is an oxo group.

In a particular embodiment, $R^1$ and $R^2$ are identical or different and are each independently selected from the group consisting of H or $(C_1-C_6)$alkyl, but preferably provided that at least one of $R^1$ or $R^2$ is not H. Preferably, said $(C_1-C_6)$alkyl is an isopropyl group.

In a preferred embodiment, at least two of $R^4$ to $R^8$ are OH and the others are H.

In another preferred embodiment, only two of $R^4$ to $R^8$ are OH and the others are H. in particular, two of $R^5$ to R7 are OH and the others are H.

Preferably, only two of $R^4$ to $R^8$ are OH and the others are H, ---- is a double bond, X is an oxygen atom, and $R^1$ and $R^2$ are identical or different and are each independently selected from the group consisting of H or $(C_1-C_6)$alkyl, provided that at least one of $R^1$ or $R^2$ is not H. Preferably, said $(C_1-C_6)$alkyl is an isopropyl group.

Preferably, at least two of $R^4$ to $R^8$ are OH and the others are H, ---- is a double bond, X is an oxygen atom and Y is an oxo group.

More preferably, at least two of $R^4$ to $R^8$ are OH and the others are H, ---- is a double bond, X is an oxygen atom and Y is an oxo group, and $R^1$ and $R^2$ are identical or different and are each independently selected from the group consisting of H or $(C_1-C_6)$alkyl, provided that at least one of $R^1$ or $R^2$ is not H. Preferably, said $(C_1-C_6)$alkyl is an isopropyl group.

Quercetin Derivatives

In a preferred embodiment, compound for use according to the present invention is a compound of formula (II):

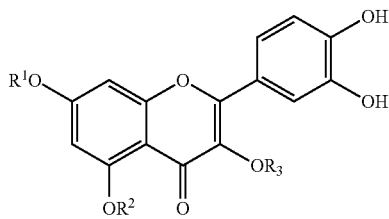
(II)

wherein $R^1$, $R^2$ and $R^3$ are as defined above.

In one embodiment, at least one of $R^1$ or $R^2$ is not H.

In another embodiment, $R^1$ and $R^2$ are identical or different and are each independently selected from the group consisting of H or $(C_1-C_6)$alkyl. Preferably, said $(C_1-C_6)$alkyl is an isopropyl group.

In particular, $R^2$ is a $(C_1-C_6)$alkyl and $R^1$ is H. Preferably, $R^2$ is an isopropyl group and $R^1$ is H, more preferably $R^1$ is a $(C_1-C_6)$alkyl and $R^2$ is H and even more preferably $R^1$ is an isopropyl group and $R^2$ is H.

Advantageously, $R^3$ is selected from the group consisting of —CO—$(C_{11}-C_{21})$alkyl or —CO—$(C_{11}-C_{21})$alkenyl. Preferably, $R^3$ is a linear —CO—$(C_{11}-C_{21})$alkyl or —CO—$(C_{11}-C_{21})$alkenyl group.

In a preferred embodiment, $R^3$ is selected from the group consisting of —CO—$(C_{13}-C_{21})$alkyl or —CO—$(C_{13}-C_{21})$alkenyl, and more preferably —CO—$(C_{15}-C_{21})$alkyl or —CO—$(C_{15}-C_{21})$alkenyl.

In a preferred embodiment, $R^3$ is a linear —CO—$(C_{15}-C_{21})$ alkyl chain, with said alkyl chain preferably containing an uneven number of carbon atoms, or a linear —CO—$(C_{15}-C_{21})$alkenyl chain, with said alkenyl chain preferably containing an uneven number of carbon atoms and advantageously cis double bond(s).

Advantageously, $R_3$ is selected from the group consisting of:

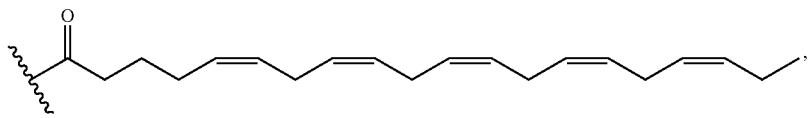

also named eicosapentaenoic acid (EPA) derivative,

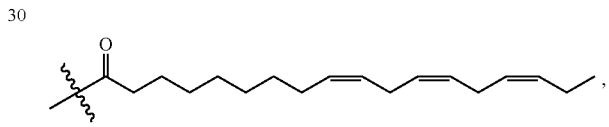

also named α-linolenic acid (ALA) derivative,

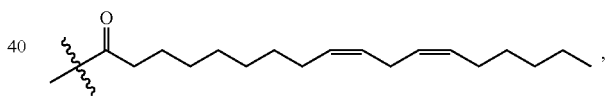

also named linoleic acid (LA) derivative or

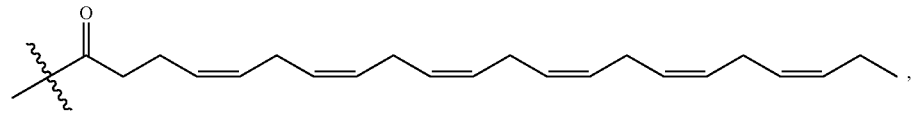

also named docosahexaenoic acid (DHA) derivative, preferably

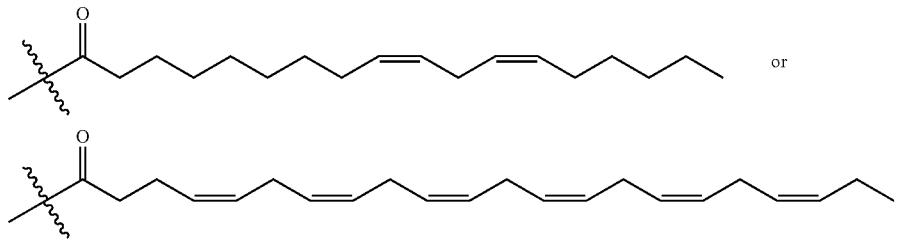

or and more preferably

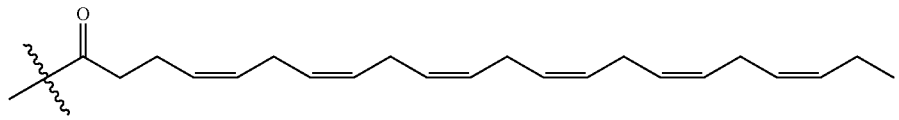

In an embodiment, the compound according to the present invention is a compound of formula (II) wherein $R^1$ and $R^2$ are H and $R^3$ is selected from the group consisting of LA and DHA, preferably $R^3$ is DHA.

In a particular embodiment, the compound according to the present invention is a compound of formula (II) wherein $R^1$ is H, $R^2$ is an isopropyl group and $R^3$ is selected from the group consisting of LA, ALA and DHA, preferably $R^3$ is DHA.

Preferably, the compound according to the present invention is a compound of formula (II) wherein $R^1$ is an isopropyl group, $R^2$ is H and $R^3$ is selected from the group consisting of LA, ALA and DHA, more preferably, $R^3$ is DHA.

Catechin Derivatives

In a particular embodiment, --- is a simple bond.

In another particular embodiment, X is advantageously an oxygen atom.

In another particular embodiment, Y is absent.

In another embodiment, --- is a simple bond, X is an oxygen atom and Y is absent.

In particular, compound for use according to the invention is a compound of formula (III):

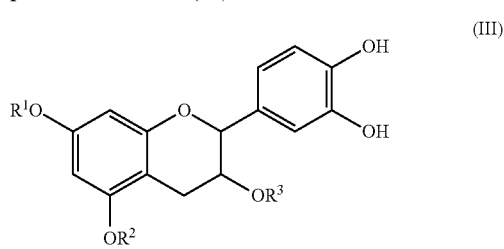

wherein $R^1$, $R^2$ and $R^3$ are as defined above.

In another embodiment, $R^1$ and $R^2$ are identical or different and are each independently selected from the group consisting of H or $(C_1-C_6)$alkyl. Preferably, said $(C_1-C_6)$alkyl is an isopropyl group. In a particular embodiment, one of $R^1$ and $R^2$ is not H.

In particular, $R^2$ is a $(C_1-C_6)$alkyl and $R^1$ is H. Preferably, $R^2$ is an isopropyl group and $R^1$ is H, more preferably $R^1$ is a $(C_1-C_6)$alkyl and $R^2$ is H and even more preferably $R^1$ is an isopropyl group and $R^2$ is H.

Advantageously, $R^3$ is selected from the group consisting of —CO—$(C_{11}-C_{21})$alkyl or —CO—$(C_{11}-C_{21})$alkenyl. Preferably, $R^3$ is a linear —CO—$(C_{11}-C_{21})$alkyl or —CO—$(C_{11}-C_{21})$alkenyl group.

In a preferred embodiment, $R^3$ is selected from the group consisting of —CO—$(C_{13}-C_{21})$alkyl or —CO—$(C_{13}-C_{21})$alkenyl, and more preferably —CO—$(C_{15}-C_{21})$alkyl or —CO—$(C_{15}-C_{21})$alkenyl.

In a preferred embodiment, $R^3$ is a linear —CO—$(C_{15}-C_{21})$ alkyl chain, with said alkyl chain preferably containing an uneven number of carbon atoms, or a linear —CO—$(C_{15}-C_{21})$alkenyl chain, with said alkenyl chain preferably containing an uneven number of carbon atoms and advantageously cis double bond(s).

Advantageously, $R_3$ is selected from the group consisting of:

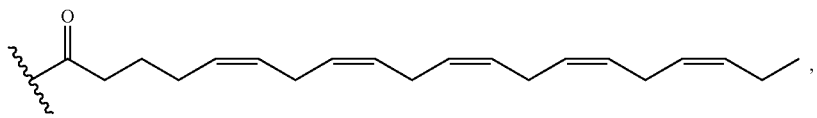 [SMILES: *C(=O)CCC/C=C\C/C=C\C/C=C\C/C=C\C/C=C\CC]

also named eicosapentaenoic acid (EPA) derivative,

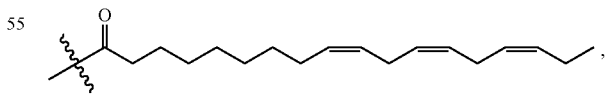

also named α-linolenic acid (ALA) derivative,

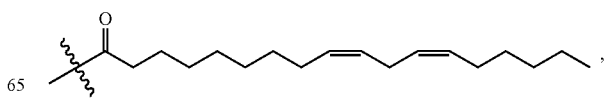

also named linoleic acid (LA) derivative or

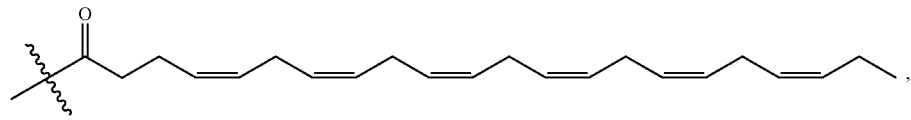

also named docosahexaenoic acid (DHA) derivative, preferably

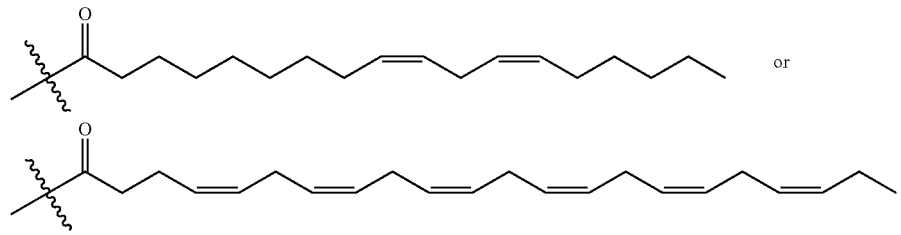

and more preferably

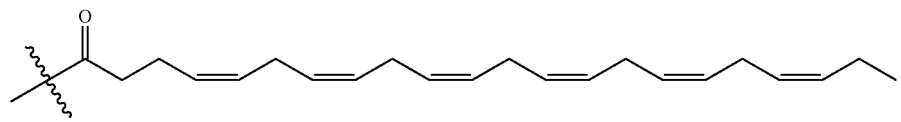 [SMILES: *C(=O)CC/C=C\C/C=C\C/C=C\C/C=C\C/C=C\C/C=C\CC]

In an embodiment, the compound according to the present invention is a compound of formula (III) wherein $R^1$ and $R^2$ are H and $R^3$ is selected from the group consisting of LA and DHA, preferably $R^3$ is DHA. In another preferred embodiment, $R^3$ is LA.

In a particular embodiment, the compound according to the present invention is a compound of formula (III) wherein $R^1$ is H, $R^2$ is an isopropyl group and $R^3$ is selected from the group consisting of LA and DHA, preferably $R^3$ is DHA. In another preferred embodiment, $R^3$ is LA.

Preferably, the compound according to the present invention is a compound of formula (III) wherein $R^1$ is an isopropyl group, $R^2$ is H and $R^3$ is selected from the group consisting of LA and DHA, more preferably, $R^3$ is DHA. In another embodiment, $R^3$ is LA.

According to a particular embodiment, compounds of the invention correspond to the following compounds:

Q-3LA-5OiP

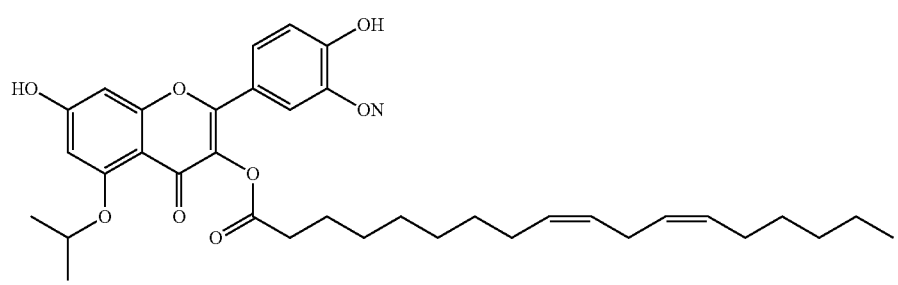

Q-3ALA-5OiP

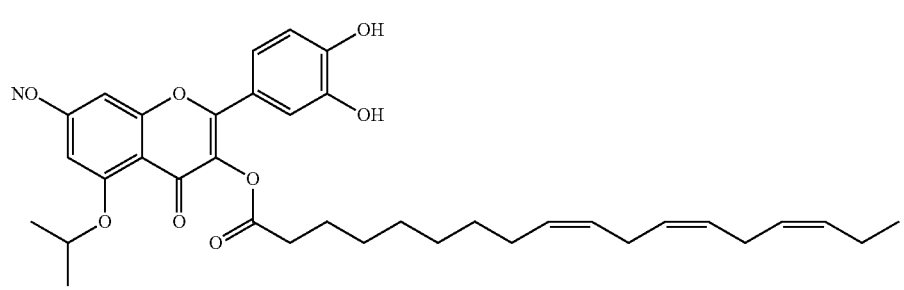

-continued
Q-3DHA-5OiP
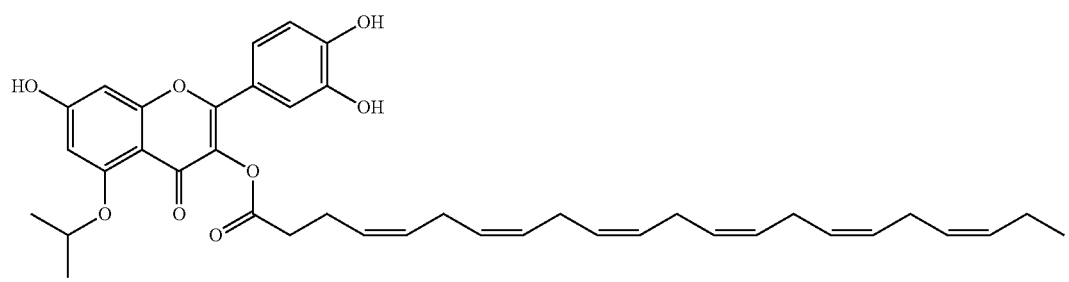
Q-3LA-7OiP
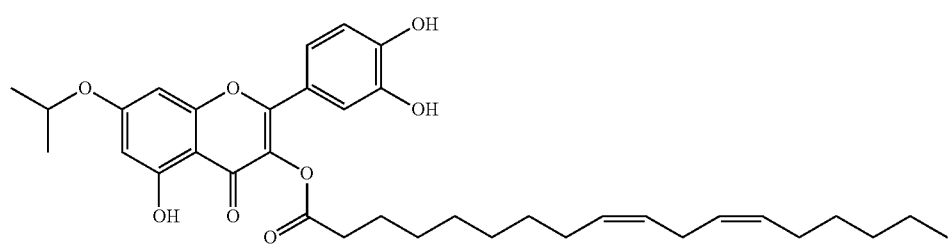
Q-3DHA-7OiP
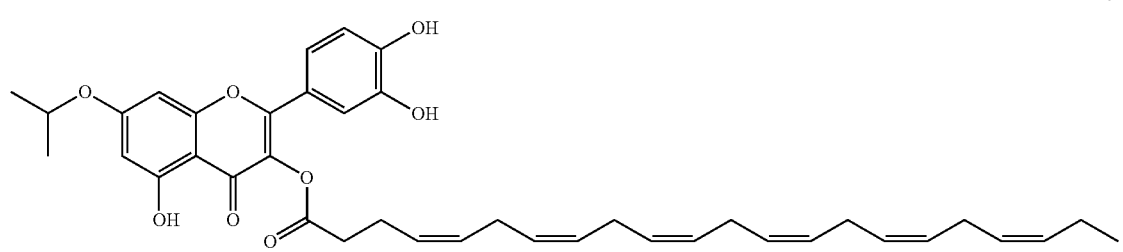
Q-3ALA-7OiP
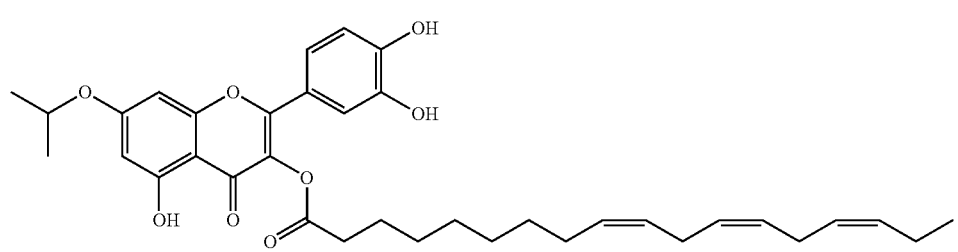
C-3LA-5OiP
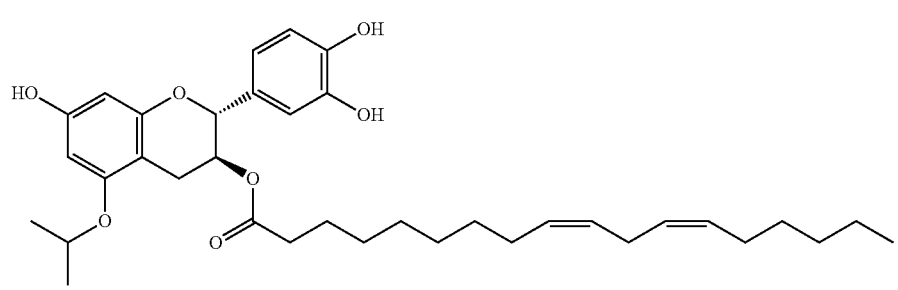
C-3;A-7OiP
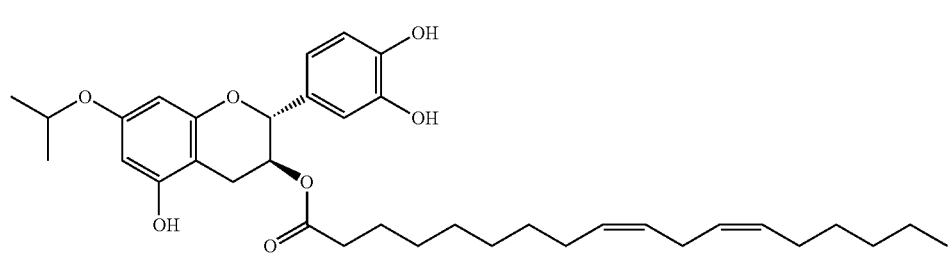

-continued
Q-3LA
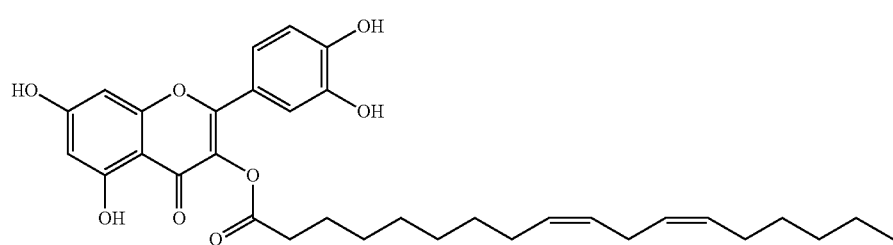
Q-3DHA
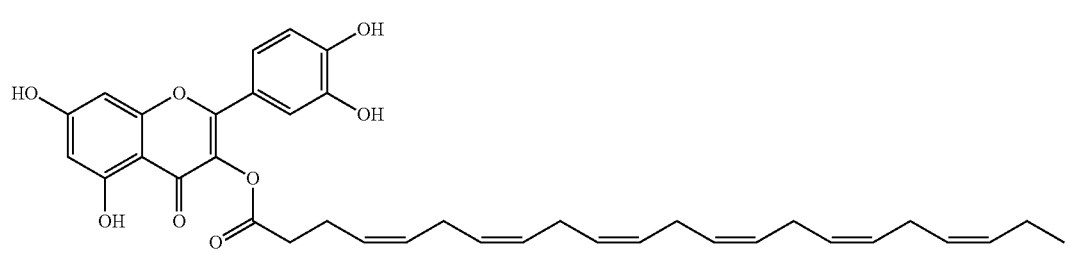
C-3LA
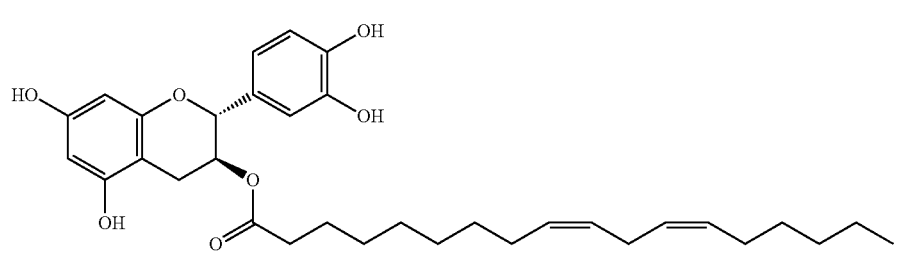
More preferably
Q-3LA-5OiP
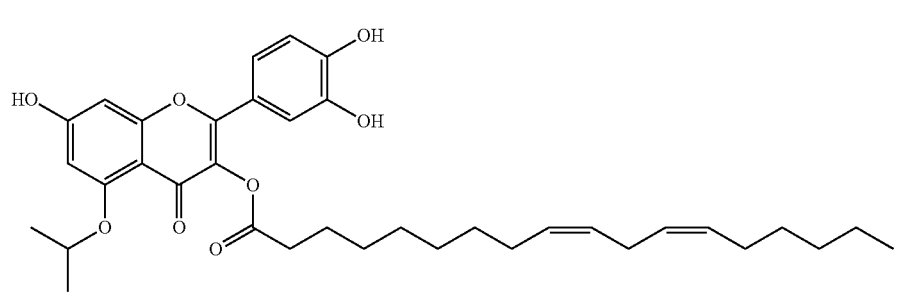
Q-3ALA-5OiP
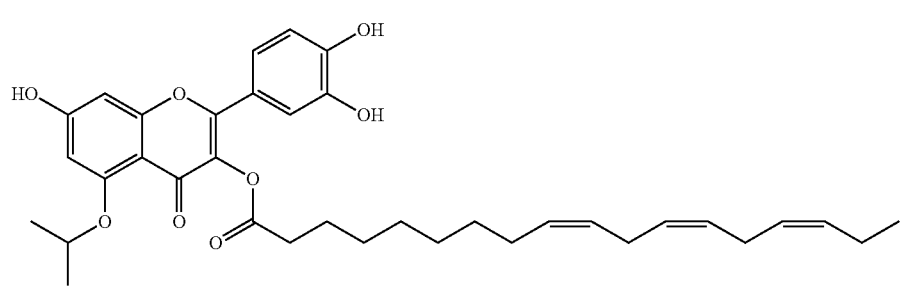

-continued

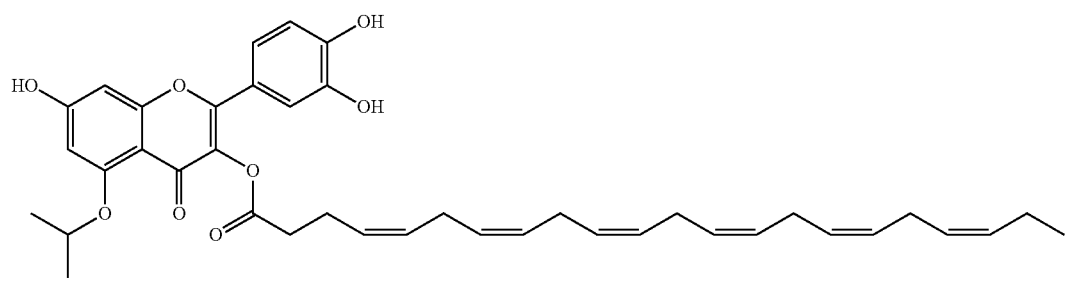
Q-3DHA-5OiP

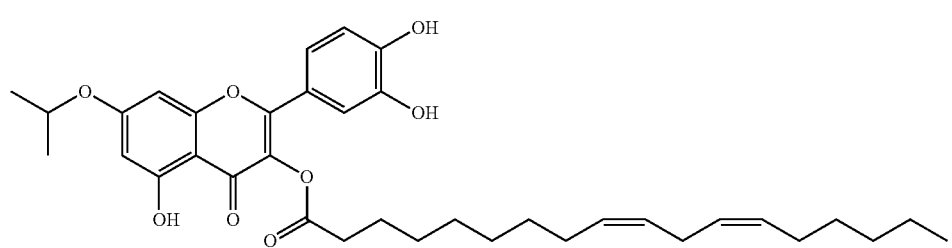
Q-3LA-7OiP

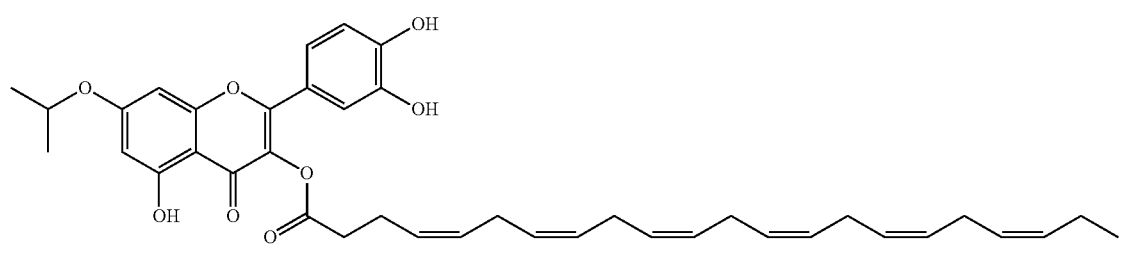
Q-3DHA-7OiP

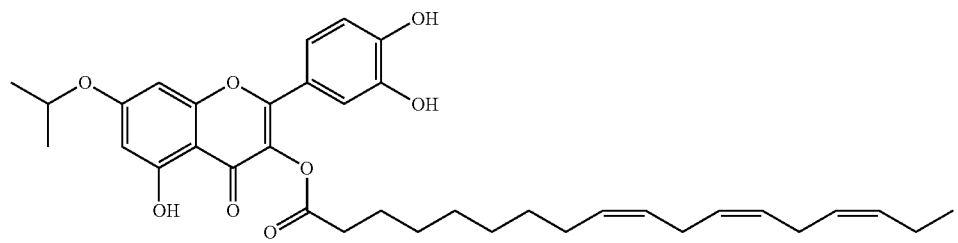
Q-3ALA-7OiP

Therapeutic and Non-Therapeutic Applications

As disclosed above, the compounds according to the present invention are used in the prevention and/or treatment of disease or disorder involving carbonyl and oxidative stresses, in particular selected from the group consisting of: inflammatory and infectious diseases, cardiovascular diseases, metabolic diseases, cancer, infertility, retinal pathologies, neuromuscular and muscular diseases, psychiatric diseases and neurodegenerative diseases.

In particular, compounds according to the present invention are used in the prevention and/or treatment of disease or disorder selected from the group consisting of cardiovascular diseases, retinal pathologies, neuromuscular and muscular diseases, and neurodegenerative diseases.

In a preferred embodiment, compounds according to the present invention are used in the prevention and/or treatment of disease or disorder selected from the group consisting of retinal pathologies, neuromuscular and muscular diseases, and neurodegenerative diseases.

In a particular and preferred embodiment, the disease or disorder involving carbonyl and oxidative stresses is selected from the group consisting of retinal pathologies and neurodegenerative disorders.

In another embodiment, the compounds according to the present invention are used in the prevention and/or treatment of biochemical, cellular, biological and/or physiological processes in which carbonyl stress and/or oxidative stress are modulated such as food oxidation, ageing or sporting activities.

In a preferred embodiment, the present invention relates to a compound of formula (I) for use in the prevention and/or treatment of retinal pathologies or neurodegenerative disease.

In a particular embodiment, compound of formula (I) according to the present invention, provided that at least one of $R^1$ or $R^2$ is not H, is used for preventing and/or treating a neurodegenerative disease.

The term "neurodegenerative disease" is used throughout the specification to identify a disease which is caused by damage to the central nervous system and can be identified by neuronal death. The neuronal cell death observed in a neurodegenerative disease is often preceded by neuronal dysfunction, sometimes by several years. Accordingly, the term "neurodegenerative disease" includes a disease or disorder that is characterized by neuronal dysfunction and eventually neuronal cell death. Exemplary neurodegenerative diseases include HIV-associated Dementia, multiple sclerosis, Alzheimer's Disease, Parkinson's Disease, amyotrophic lateral sclerosis, and Pick's Disease.

According to another particular embodiment, the neurodegenerative disease includes Alzheimer's disease and Parkinson's disease.

Advantageously, the present invention relates to a compound of formula (I) as defined above or below, or a hydrate or a solvate thereof, for use in the prevention and/or treatment of a retinal pathologies. According to a particular embodiment, the retinal pathologies include retinal aging-associated pathologies, such as Age-related Macular Degeneration (AMD), and retinal genetic pathologies, such as Stargardt disease.

In particular embodiments, the following lipophenolic compounds are preferably used for the following disorders according to the invention:

TABLE 1

|  | Retinal pathologies (ex: AMD, Stargardt disease) | Neurodegenerative disease (ex: Alzheimer's disease and Parkinson's disease) | Neuro-muscular and muscular diseases | Cardio-vascular diseases |
| --- | --- | --- | --- | --- |
| 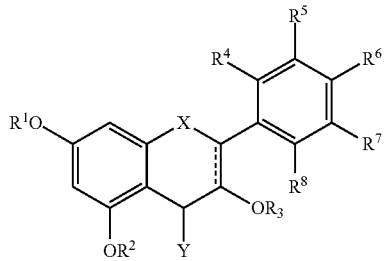<br>(I)<br>wherein<br>$R^2$ is an isopropyl group and $R^1$ is H, more preferably $R^1$ is a $(C_1-C_6)$ alkyl and $R^2$ is H and even more preferably $R^1$ is an isopropyl group and $R^2$ is H, $R^3$ is selected from the group consisting of —C(O)—($C_{11}$-$C_{21}$) alkyl or —C(O)—($C_{11}$-$C_{21}$) alkenyl, preferably —C(O)-($C_{15}$-$C_{21}$) alkyl or —C(O)—($C_{15}$-$C_{21}$) alkenyl, at least two $R^4$ to $R^8$ are OH and the other are H, X is O, Y is an oxo goup,<br>===== is a double bond,<br>or its pharmaceutically acceptable salts, racemates, diastereoisomers, enantiomers or mixtures thereof. | x | x | x | x |
| 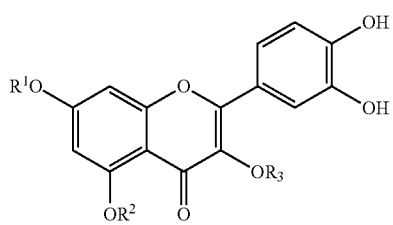<br>(II)<br>wherein<br>$R^2$ is an isopropyl group and $R^1$ is H, more preferably $R^1$ is a $(C_1-C_6)$ alkyl and $R^2$ is H and even more preferably $R^1$ is an isopropyl group and $R^2$ is H, $R^3$ is a linear —CO—($C_{13}$-$C_{21}$) alkyl or —CO—($C_{13}$-$C_{21}$) alkenyl group, prefereably-a linear CO—($C_{15}$- | x | x | x | x |

TABLE 1-continued

| | Retinal pathologies (ex: AMD, Stargardt disease) | Neurodegenerative disease (ex: Alzheimer's disease and Parkinson's disease) | Neuro-muscular and muscular diseases | Cardio-vascular diseases |
|---|---|---|---|---|
| $C_{21}$) alkyl or —CO—($C_{15}$-$C_{21}$) alkenyl group, preferably $R^3$ is selected from the group consisting in EPA, ALA, LA and DHA, preferably LA and DHA, more preferably DHA, or its pharmaceutically acceptable salts, racemates, diastereoisomers, enantiomers or mixtures thereof. Examples: Q-3DHA-7OiP, Q-3LA-7OiP, Q-3ALA-7OiP, preferably Q-3DHA-7OiP Q-3DHA-5OiP, Q-3LA-5OiP, Q-3ALA-5OiP, | | | | |
| 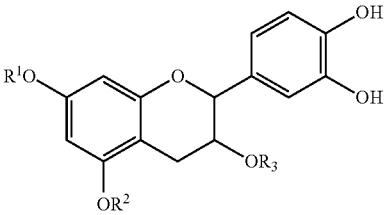<br>(III)<br>wherein<br>$R^2$ is an isopropyl group and $R^1$ is H, more preferably $R^1$ is a ($C_1$-$C_6$) alkyl and $R^2$ is H and even more preferably $R^1$ is an isopropyl group and $R^2$ is H, $R^3$ is a linear —CO—($C_{13}$-$C_{21}$) alkyl or —CO—($C_{13}$-$C_{21}$) alkenyl group, preferably-a linear CO—($C_{15}$-$C_{21}$) alkyl or —CO—($C_{15}$-$C_{21}$) alkenyl group, preferably $R^3$ is selected from the group consisting in EPA, ALA, LA and DHA, preferably LA and DHA, more preferably DHA, or its pharmaceutically acceptable salts, racemates, diastereoisomers, enantiomers or mixtures thereof Examples: C-3LA-5OiP, C-7LA-7OiP | x | x | x | x |

In a particular embodiment, compounds according to the invention for use in the prevention or treatment of metabolic disorders are selected in the group consisting of:

Compounds of formula (I), wherein X and $R^1$ to $R^8$ are as disclosed above, provided that one of $R^1$ or $R^2$ is H and the other is not H, in particular $R^2$ is a ($C_1$-$C_6$)alkyl and $R^1$ is H, preferably $R^2$ is an isopropyl group and $R^1$ is H, or more preferably $R^1$ is a ($C_1$-$C_6$)alkyl and $R^2$ is H, even more preferably $R^1$ is an isopropyl group and $R^2$ is H, and $R^3$ to $R^8$ are as disclosed above;

Compounds of formula (I), wherein X and $R^1$ to $R^8$ are as disclosed above, provided that one of $R^1$ or $R^2$ is H and the other is not H, and wherein at least two of $R^4$ to $R^8$ are OH, the other groups are H;

Compounds of formula (II) as disclosed hereunder;

Compounds of formula (III) as disclosed hereunder.

In a particular embodiment, compounds according to the invention for use in the prevention or treatment of inflammatory disorders are selected in the group consisting of:

Compounds of formula (I), wherein X and $R^1$ to $R^8$ are as disclosed above, provided that one of $R^1$ or $R^2$ is H and the other is not H, in particular $R^2$ is a ($C_1$-$C_6$)alkyl and $R^1$ is H, preferably $R^2$ is an isopropyl group and $R^1$ is H, or more preferably $R^1$ is a ($C_1$-$C_6$)alkyl and $R^2$ is H, even more preferably $R^1$ is an isopropyl group and $R^2$ is H, and $R^3$ to $R^8$ are as disclosed above;

Compounds of formula (I), wherein X and $R^1$ to $R^8$ are as disclosed above, provided that one of $R^1$ or $R^2$ is H and the other is not H, and wherein at least two of $R^4$ to $R^8$ are OH, the other groups are H;

Compounds of formula (II) as disclosed hereunder;

Compounds of formula (III) as disclosed hereunder.

In a particular embodiment, compounds according to the invention for use in the prevention or treatment of cancer are selected in the group consisting of:

Compounds of formula (I), wherein X and $R^1$ to $R^8$ are as disclosed above, provided that one of $R^1$ or $R^2$ is H and the other is not H, in particular $R^2$ is a $(C_1-C_6)$alkyl and $R^1$ is H, preferably $R^2$ is an isopropyl group and $R^1$ is H, or more preferably $R^1$ is a $(C_1-C_6)$alkyl and $R^2$ is H, even more preferably $R^1$ is an isopropyl group and $R^2$ is H, and $R^3$ to $R^8$ are as disclosed above;

Compounds of formula (I), wherein X and $R^1$ to $R^8$ are as disclosed above, provided that one of $R^1$ or $R^2$ is H and the other is not H, and wherein at least two of $R^4$ to $R^8$ are OH, the other groups are H;

Compounds of formula (II) as disclosed hereunder;

Compounds of formula (III) as disclosed hereunder.

In another aspect, the present invention relates to a method for preventing, reducing the progression or treating a disease or disorder involving both carbonyl and oxidative stresses, comprising administering to a patient in need thereof a therapeutically effective amount of a compound of formula (I) as defined above or a hydrate or a solvate thereof.

Specific Compounds

The present invention also relates to a compound of formula (I):

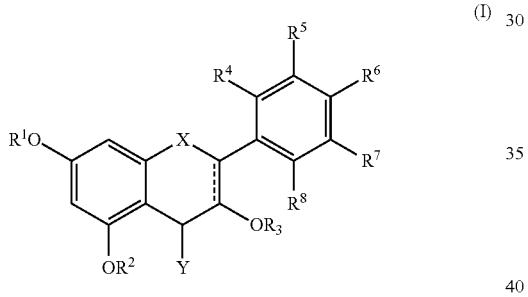

wherein $R^1$ and $R^2$ are identical or different and are each independently selected from the group consisting of H, $(C_1-C_6)$alkyl, —C(O)—$(C_{11}-C_{21})$alkyl or —C(O)—$(C_{11}-C_{21})$alkenyl, provided that one of $R^1$ or $R^2$ is H and the other is not H, $R^3$ is selected from the group consisting of $(C_1-C_6)$alkyl, —C(O)—$(C_{11}-C_{21})$alkyl or —C(O)—$(C_{11}C_{21})$alkenyl, $R^4$ to $R^8$ are identical or different and are each independently selected from the group consisting of H, OH, O$(C_1-C_6)$alkyl, —OC(O)—$(C_{11}-C_{21})$alkyl or —OC(O)—$(C_{11}-C_{21})$alkenyl, X is selected from the group consisting of O, S, $CH_2$ or NH, Y is absent or oxo group, --- is simple or double bond, or its pharmaceutically acceptable salts, racemates, diastereoisomers, enantiomers or mixtures thereof.

Advantageously, X is O.

In a particular embodiment Y is an oxo group and --- is a double bond.

In a preferred embodiment, at least two of $R^4$ to $R^8$ are OH and the other are H.

In a particular embodiment, the present invention also relates to a compound of formula (I):

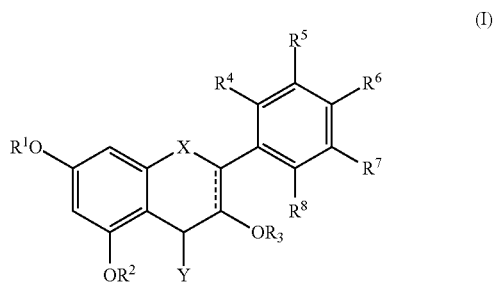

wherein $R^2$ is a $(C_1-C_6)$alkyl and $R^1$ is H, preferably $R^2$ is an isopropyl group and $R^1$ is H, or more preferably $R^1$ is a $(C_1-C_6)$alkyl and $R^2$ is H, even more preferably $R^1$ is an isopropyl group and $R^2$ is H, $R^3$ is selected from the group consisting of —C(O)—$(C_{11}-C_{21})$alkyl or —C(O)—$(C_{11}-C_{21})$alkenyl, preferably —C(O)—$(C_{15}-C_{21})$alkyl or —C(O)—$(C_{15}-C_{21})$alkenyl, at least two $R^4$ to $R^8$ are OH and the other are H, X is O, Y is an oxo group, --- is a double bond, or its pharmaceutically acceptable salts, racemates, diastereoisomers, enantiomers or mixtures thereof.

In a preferred embodiment, compound of the invention is a compound of formula (II):

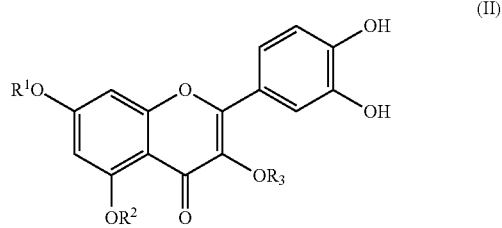

wherein $R^1$, $R^2$ and $R^3$ are as defined above.

In a preferred embodiment, $R^2$ is a $(C_1-C_6)$alkyl and $R^1$ is H. Preferably, $R^2$ is an isopropyl group and $R^1$ is H, more preferably $R^1$ is a $(C_1-C_6)$alkyl and $R^2$ is H and even more preferably $R^1$ is an isopropyl group and $R^2$ is H.

Preferably, $R^3$ is a linear —CO—$(C_{11}-C_{21})$alkyl or —CO—$(C_{11}-C_{21})$alkenyl group. In a preferred embodiment, $R^3$ is a linear —CO—$(C_{13}-C_{21})$alkyl or —CO—$(C_{13}-C_{21})$alkenyl group, preferably—a linear CO—$(C_{15}-C_{21})$alkyl or —CO—$(C_{15}-C_{21})$alkenyl group.

In another preferred embodiment, $R^3$ is selected from the group consisting in EPA, ALA, LA and DHA, preferably LA and DHA, more preferably DHA.

In another particular embodiment, Y is absent and --- is a simple bond.

In another preferred embodiment, compound of the invention is a compound of formula (III):

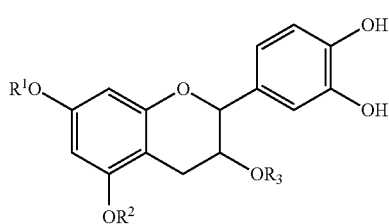

wherein $R^1$, $R^2$ and $R^3$ are as defined above. In a particular embodiment, one of $R^1$ and $R^2$ is not H.

In a preferred embodiment, $R^2$ is a $(C_1-C_6)$alkyl and $R^1$ is H. Preferably, $R^2$ is an isopropyl group and $R^1$ is H, more preferably $R^1$ is a $(C_1-C_6)$alkyl and $R^2$ is H and even more preferably $R^1$ is an isopropyl group and $R^2$ is H.

Preferably, $R^3$ is a linear —CO—$(C_{11}-C_{21})$alkyl or —CO—$(C_{11}-C_{21})$alkenyl group. In a preferred embodiment, $R^3$ is a linear —CO—$(C_{13}-C_{21})$alkyl or —CO—$(C_{13}-C_{21})$alkenyl group, preferably—a linear CO—$(C_{15}-C_{21})$alkyl or —CO—$(C_{15}-C_{21})$alkenyl group.

In another preferred embodiment, $R^3$ is selected from the group consisting in EPA, ALA, LA and DHA, preferably LA and DHA, more preferably DHA.

In another preferred embodiment, compounds of formula (I) according to the present invention correspond to the following compounds:

Q-3LA-5OiP

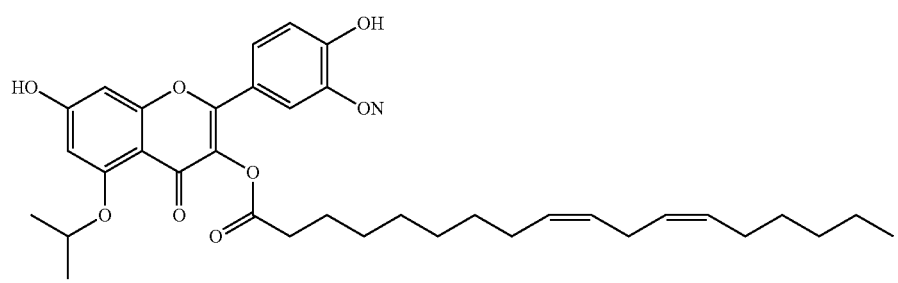

Q-3ALA-5OiP

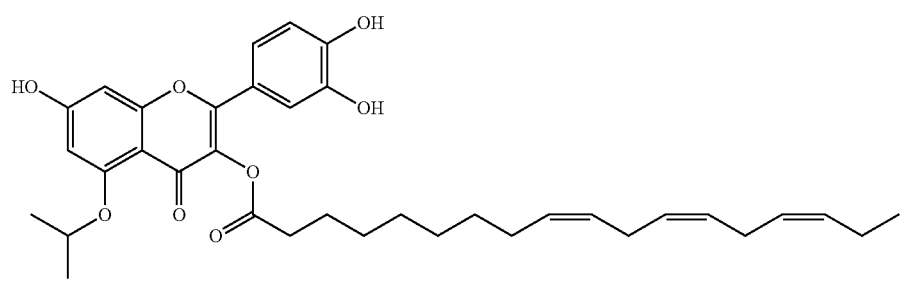

Q-3DHA-5OiP

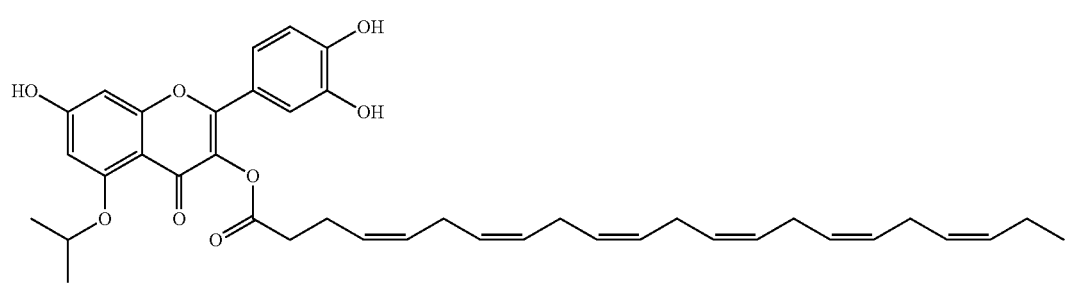

Q-3LA-7OiP

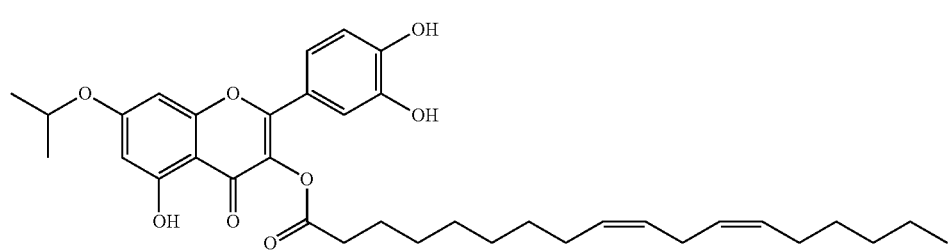

-continued
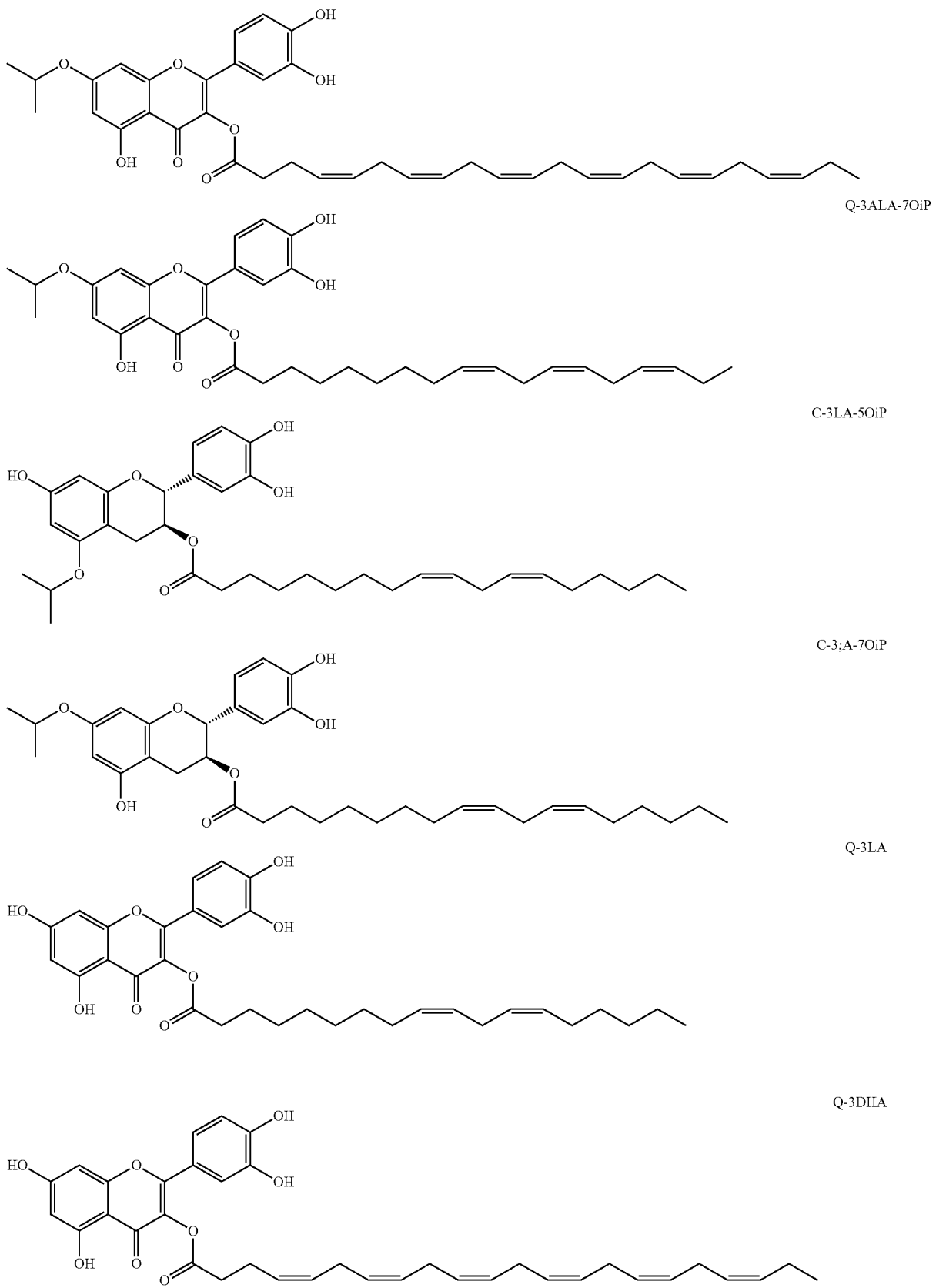

-continued
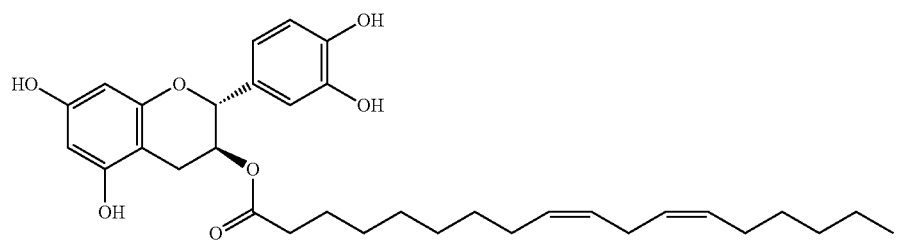
C-3LA
in particular
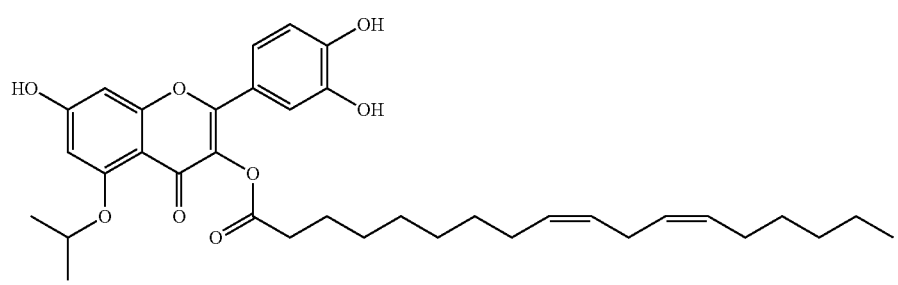
Q-3LA-5OiP
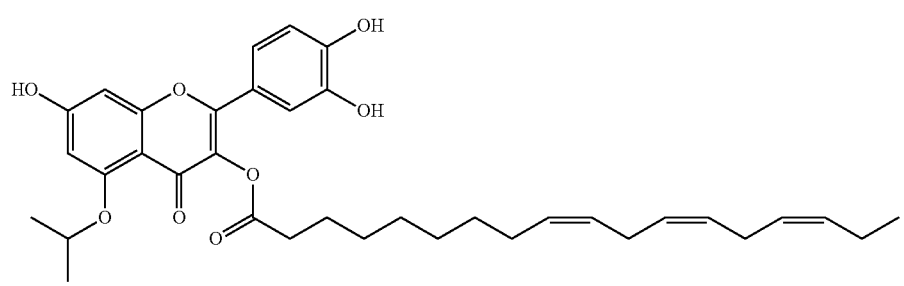
Q-3ALA-5OiP
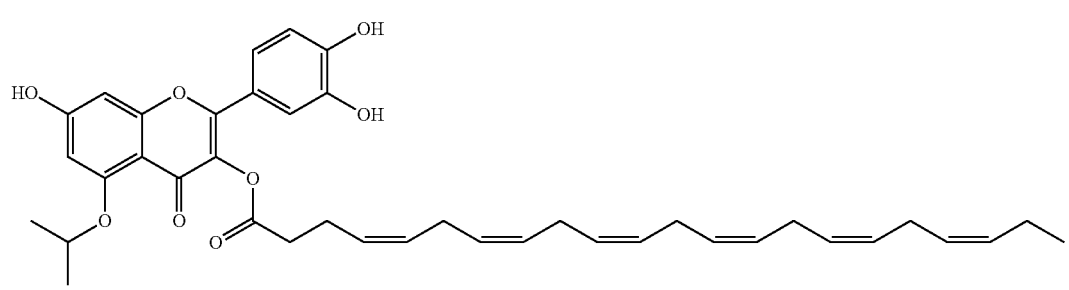
Q-3DHA-5OiP
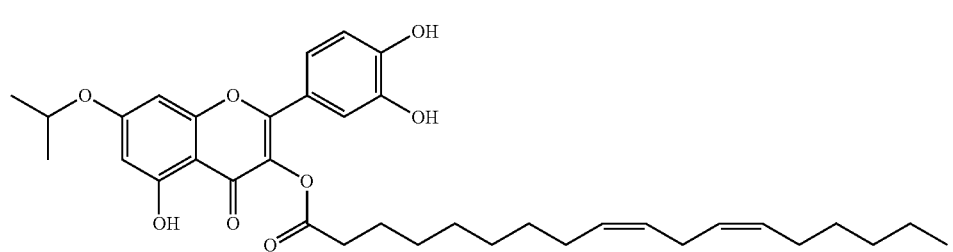
Q-3LA-7OiP -continued
Q-3DHA-7OiP
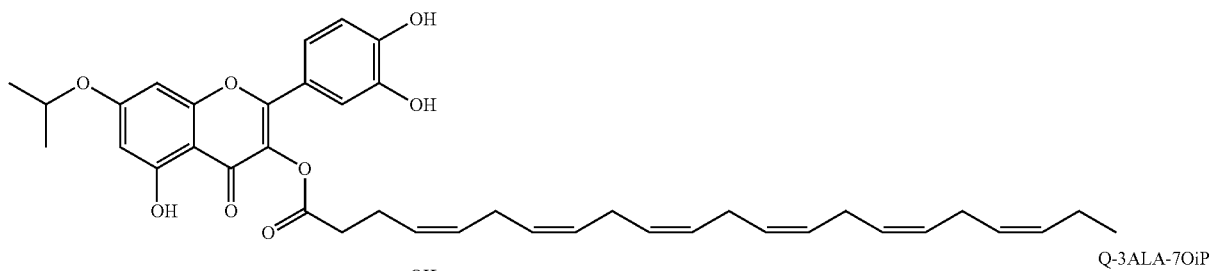
Q-3ALA-7OiP
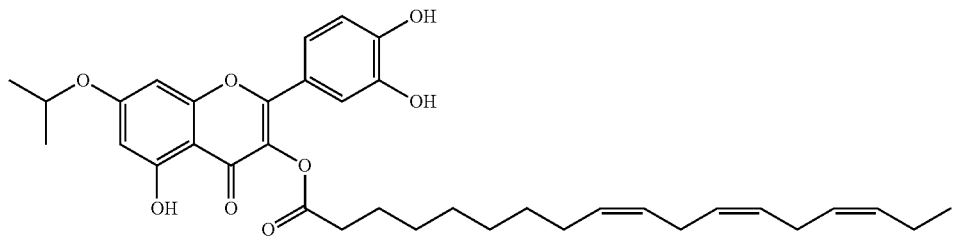
C-3LA-5OiP
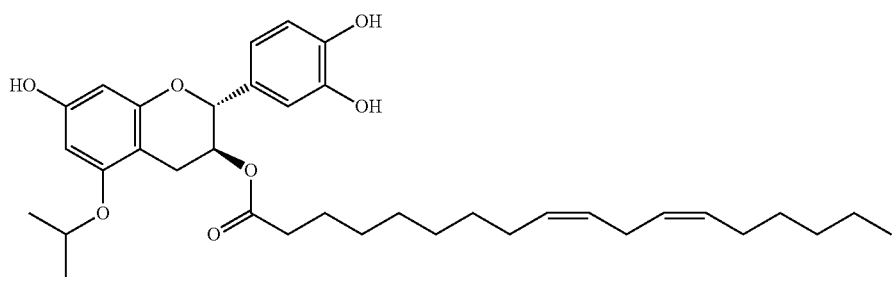
C-3LA-7OiP
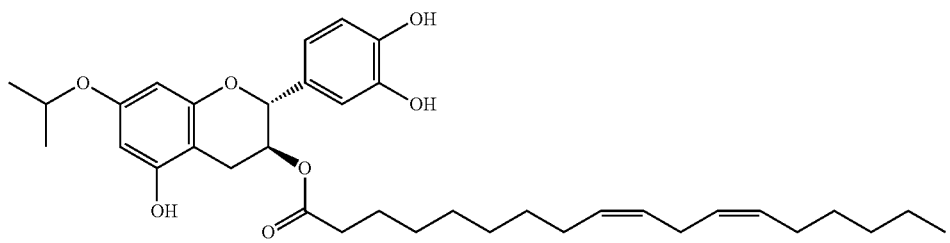
more preferably
Q-3LA-5OiP
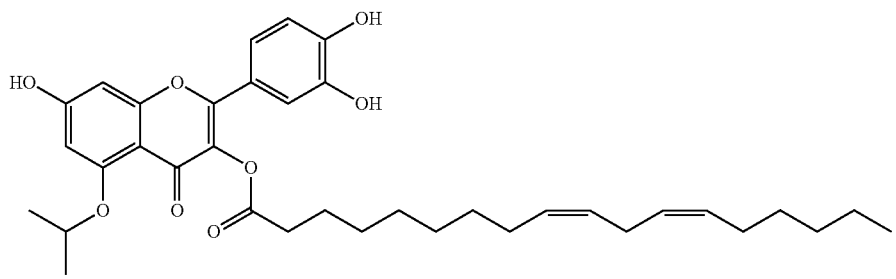

-continued

Q-3ALA-5OiP
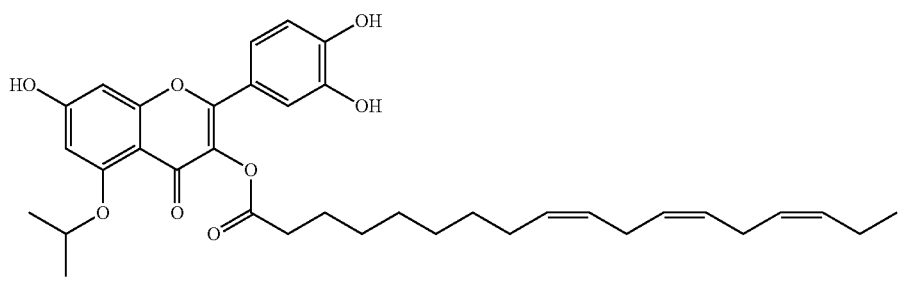

Q-3DHA-5OiP
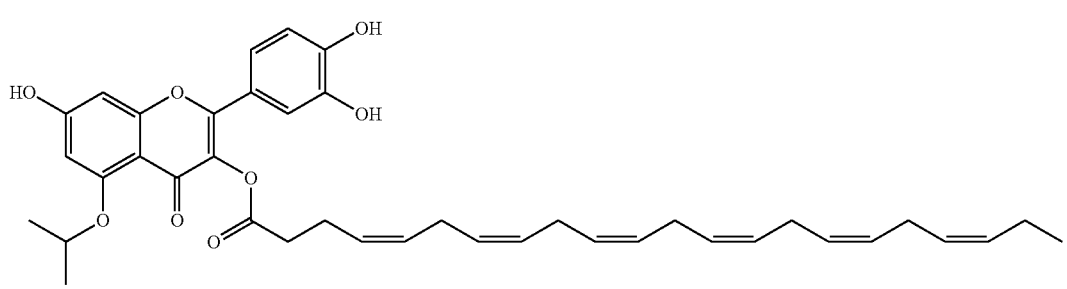

Q-3LA-7OiP
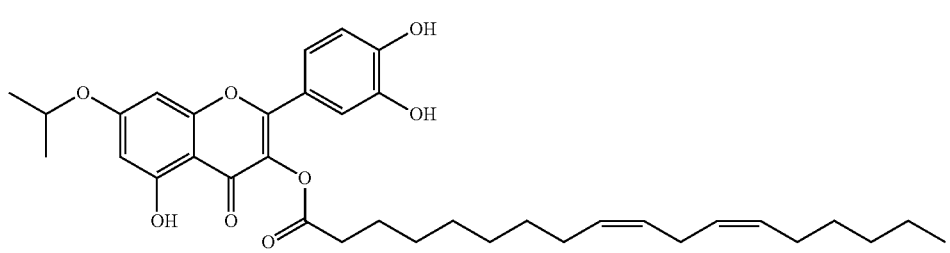

Q-3DHA-7OiP
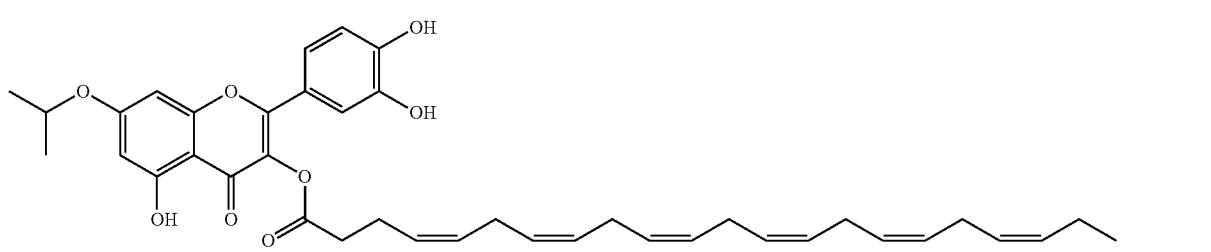

Q-3ALA-7OiP
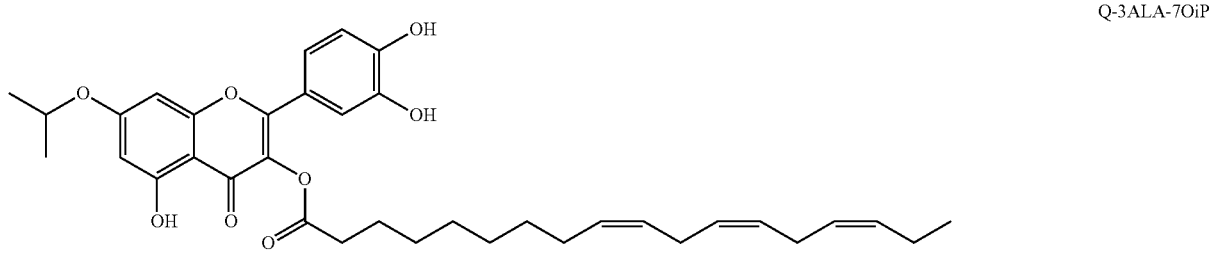

The compound of the invention may be used as such but is preferably formulated in a composition, in particular a cosmetic, nutritional, or pharmaceutical composition comprising at least one cosmetically acceptable, food-grade excipient or pharmaceutically acceptable vehicle.

Compositions

So, another object of the invention is a composition, in particular a cosmetic, nutritional or pharmaceutical composition comprising, in a cosmetically, food-grade or pharmaceutically acceptable vehicle, at least one compound of the invention.

In the present description, by food-grade or pharmaceutically or cosmetically acceptable vehicle or excipient is meant a compound or combination of compounds included in a nutritional, pharmaceutical or cosmetic composition which does not cause secondary reactions and for example allows facilitated administering of the active compound(s), increased lifetime thereof and/or efficacy in the body, increased solubility in solution etc. These acceptable excipients are well known and can be adapted by persons skilled in the art to the type and mode of administration of the selected active compound(s).

In a particular embodiment, the composition is a cosmetic composition.

In another particular embodiment, the composition is a nutritional composition. The term "nutritional composition" particularly encompasses nutraceutical compositions (particularly food supplements), health-food compositions and beverages, particularly of dietary or nutritional nature such as beverages with antioxidant properties.

In another and preferred embodiment, the composition is a pharmaceutical composition comprising, in a pharmaceutically acceptable vehicle, at least one compound of formula (I) defined above.

In a particular embodiment Y is an oxo group and $=\!=\!=$ is a double bond.

In a preferred embodiment, at least two $R^4$ to $R^8$ are OH and the other are H.

In a preferred embodiment, compound of the invention is a compound of formula (II):

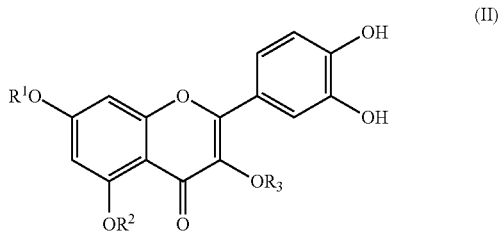

(II)

wherein $R^1$, $R^2$ and $R^3$ are as defined above.

In a preferred embodiment, $R^2$ is a $(C_1$-$C_6)$alkyl and $R^1$ is H. Preferably, $R^2$ is an isopropyl group and $R^1$ is H, more preferably $R^1$ is a $(C_1$-$C_6)$alkyl and $R^2$ is H and even more preferably $R^1$ is an isopropyl group and $R^2$ is H.

Preferably, $R^3$ is a linear —CO—$(C_{11}$-$C_{21})$alkyl or —CO—$(C_{11}$-$C_{21})$alkenyl group. In a preferred embodiment, $R^3$ is a linear —CO—$(C_{13}$-$C_{21})$alkyl or —CO—$(C_{13}$-$C_{21})$ alkenyl group, preferably—a linear CO—$(C_{15}$-$C_{21})$alkyl or —CO—$(C_{15}$-$C_{21})$alkenyl group.

In another preferred embodiment, $R^3$ is selected from the group consisting in EPA, ALA, LA and DHA, preferably LA and DHA, more preferably DHA.

In another particular embodiment, Y is absent and $=\!=\!=$ is a simple bond.

In another preferred embodiment, compound of the invention is a compound of formula (III):

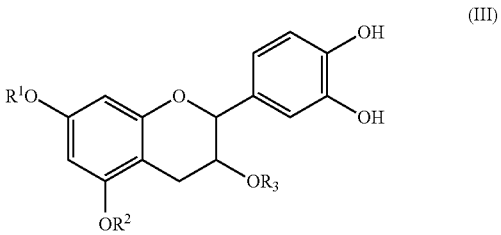

(III)

wherein $R^1$, $R^2$ and $R^3$ are as defined above.

In a preferred embodiment, $R^2$ is a $(C_1$-$C_6)$alkyl and $R^1$ is H. Preferably, $R^2$ is an isopropyl group and $R^1$ is H, more preferably $R^1$ is a $(C_1$-$C_6)$alkyl and $R^2$ is H and even more preferably $R^1$ is an isopropyl group and $R^2$ is H.

Preferably, $R^3$ is a linear —CO—$(C_{11}$-$C_{21})$alkyl or —CO—$(C_{11}$-$C_{21})$alkenyl group. In a preferred embodiment, $R^3$ is a linear —CO—$(C_{13}$-$C_{21})$alkyl or —CO—$(C_{13}$-$C_{21})$ alkenyl group, preferably—a linear CO—$(C_{15}$-$C_{21})$alkyl or —CO—$(C_{15}$-$C_{21})$alkenyl group.

In another preferred embodiment, $R^3$ is selected from the group consisting in EPA, ALA, LA and DHA, preferably LA and DHA, more preferably DHA.

In a particular embodiment, the pharmaceutical composition comprises, in a pharmaceutically acceptable vehicle, at least one compound selected from the group consisting of:

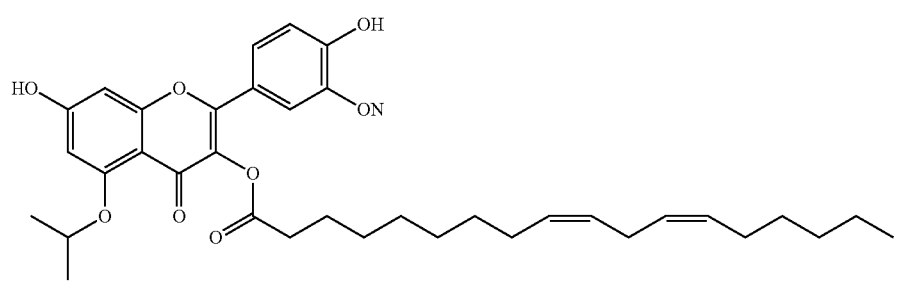

Q-3LA-5OiP

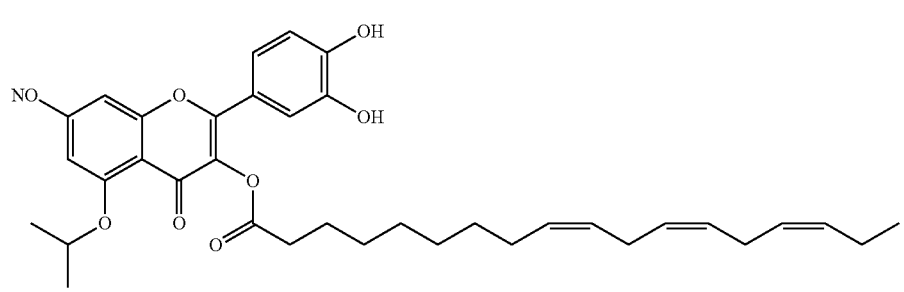

Q-3ALA-5OiP

-continued
Q-3DHA-5OiP
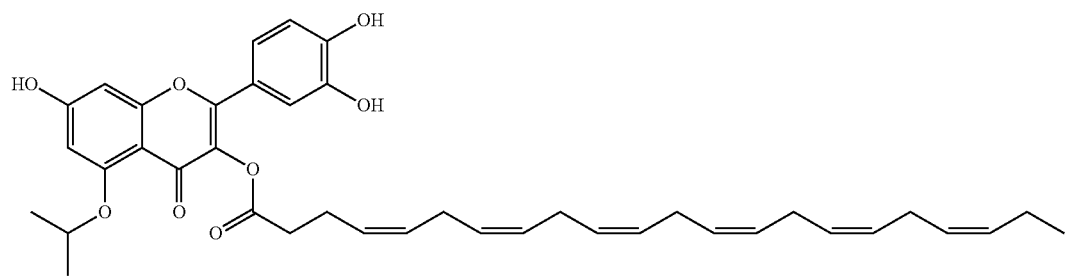
Q-3LA-7OiP
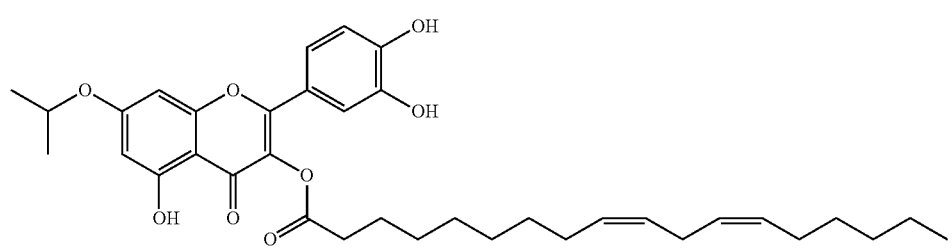
Q-3DHA-7OiP
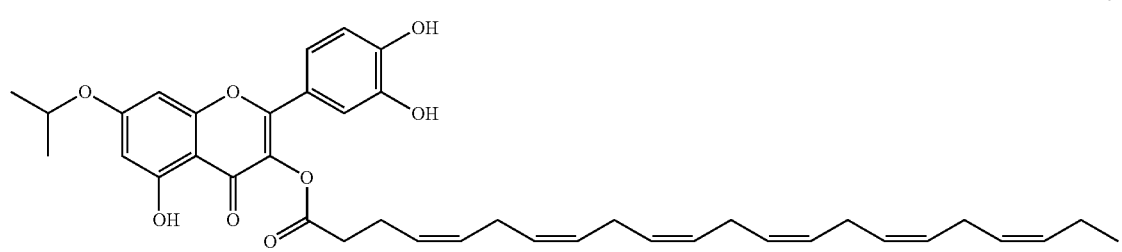
Q-3ALA-7OiP
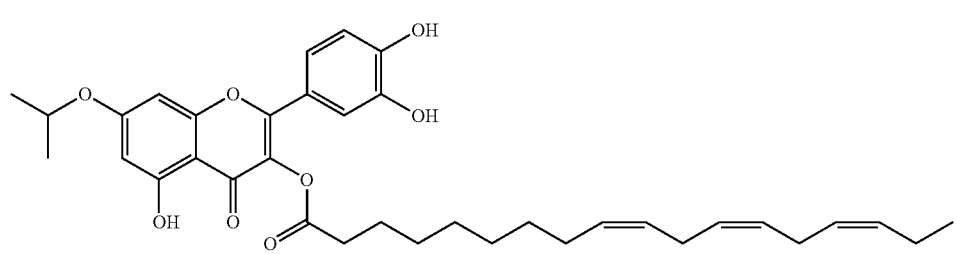
C-3LA-5OiP
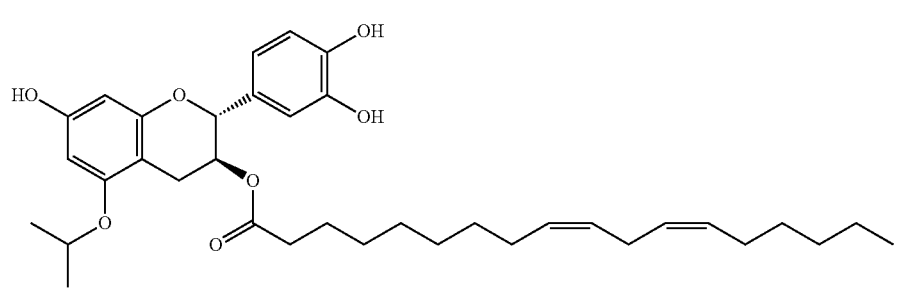
C-3;A-7OiP
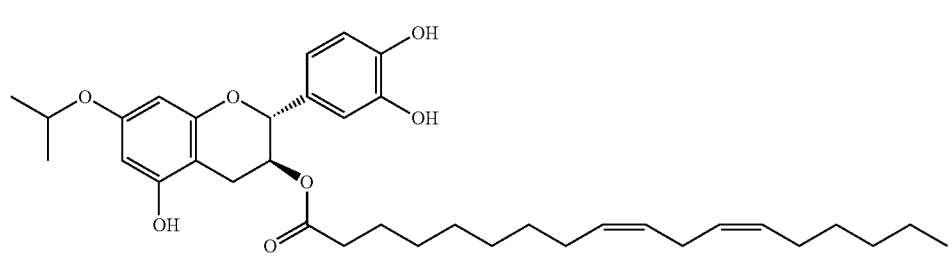

-continued
Q-3LA
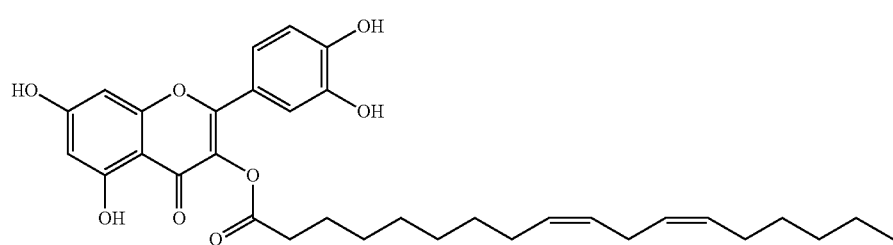
Q-3DHA
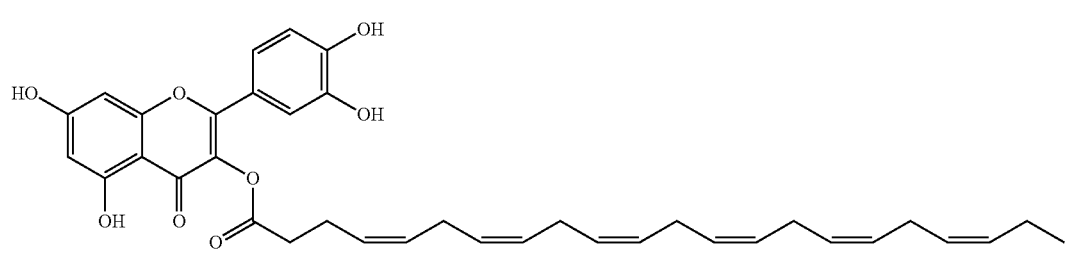
C-3LA
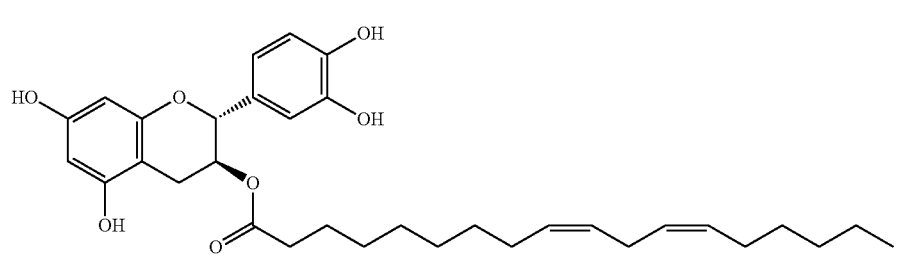
preferably
Q-3LA-5OiP
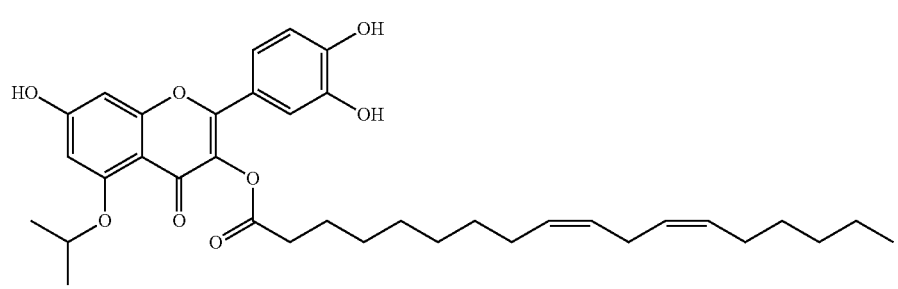
Q-3ALA-5OiP
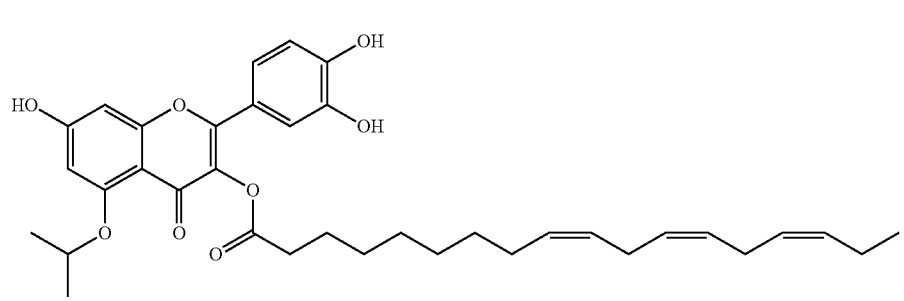

-continued
Q-3DHA-5OiP
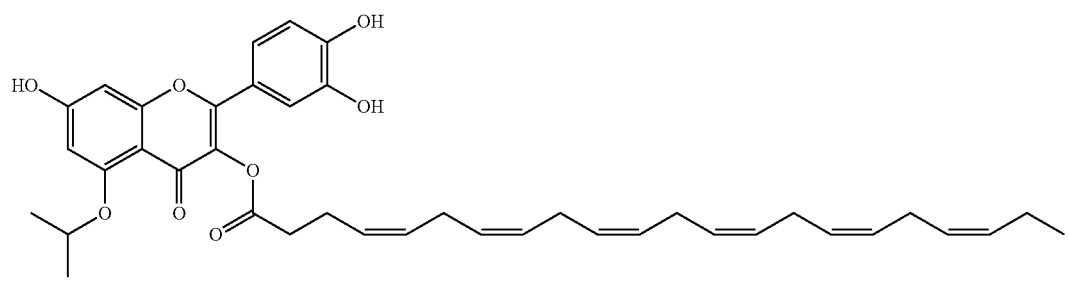
Q-3LA-7OiP
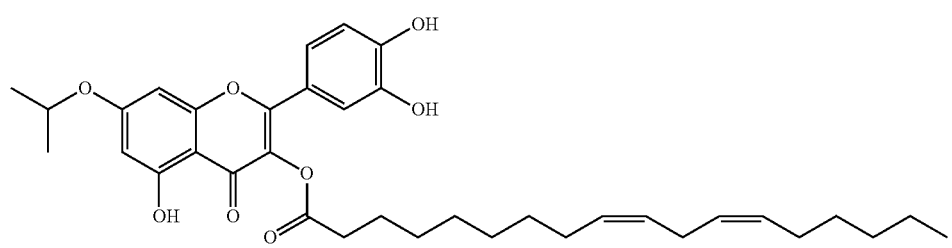
Q-3DHA-7OiP
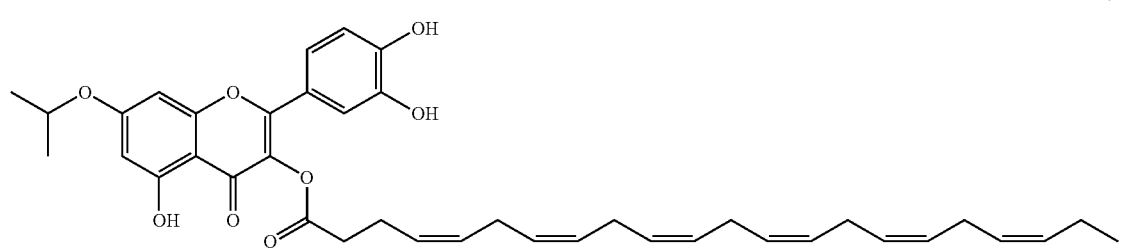
Q-3ALA-7OiP
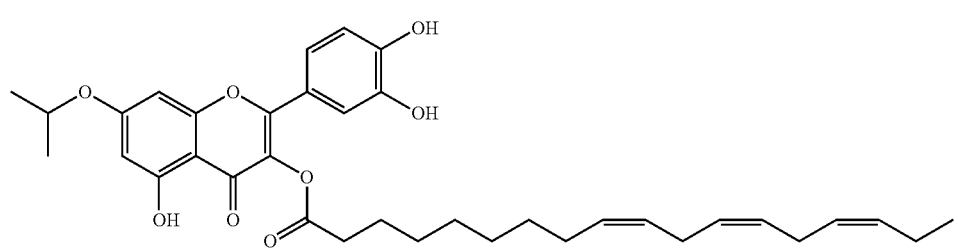
C-3LA-5OiP
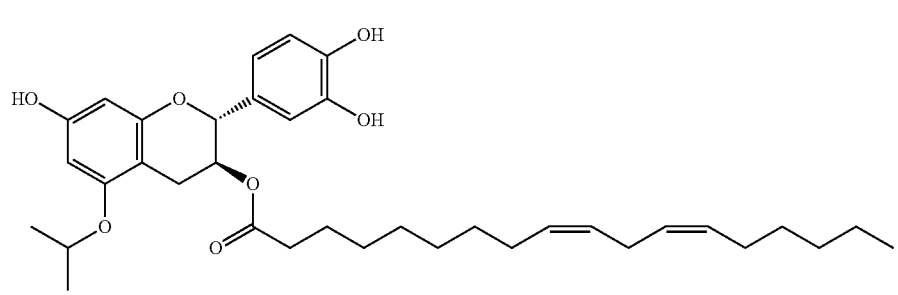
C-3LA-7OiP
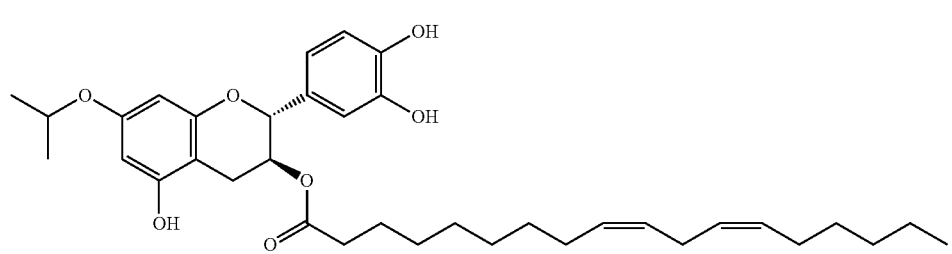

more preferably
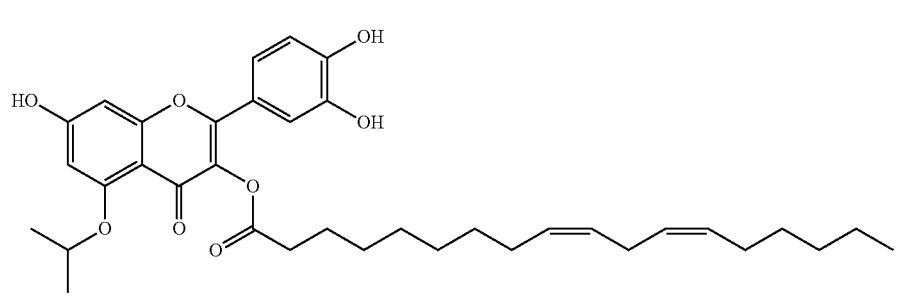
Q-3LA-5OiP
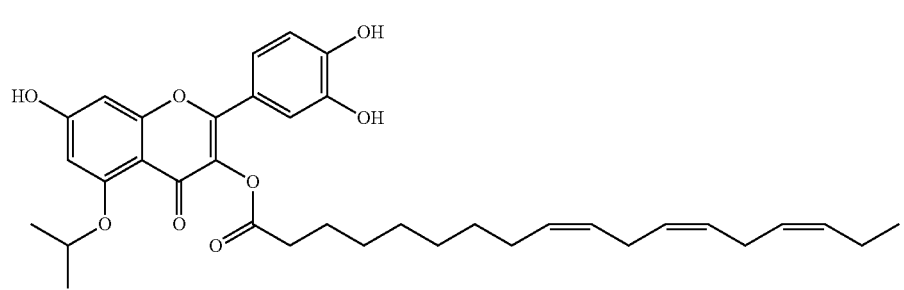
Q-3ALA-5OiP
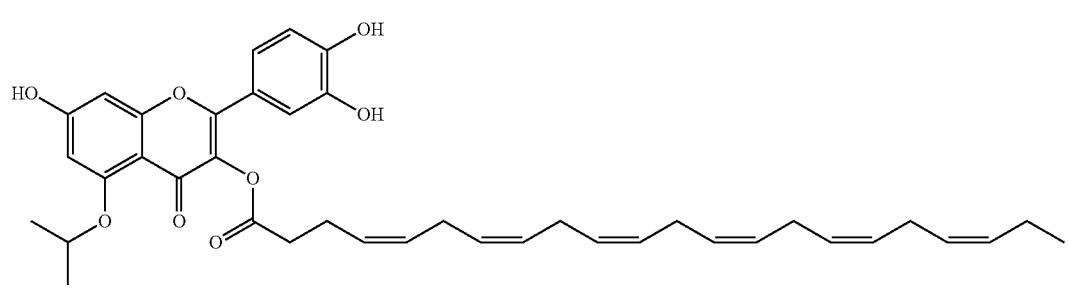
Q-3DHA-5OiP
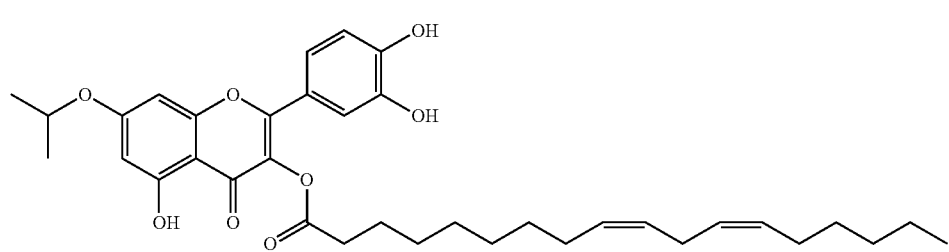
Q-3LA-7OiP
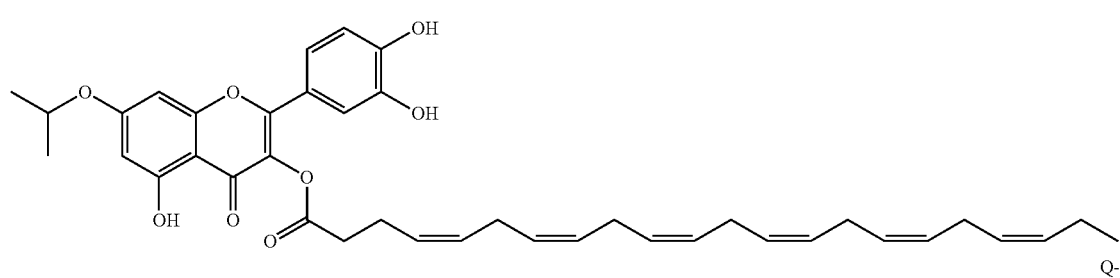
Q-3DHA-7OiP
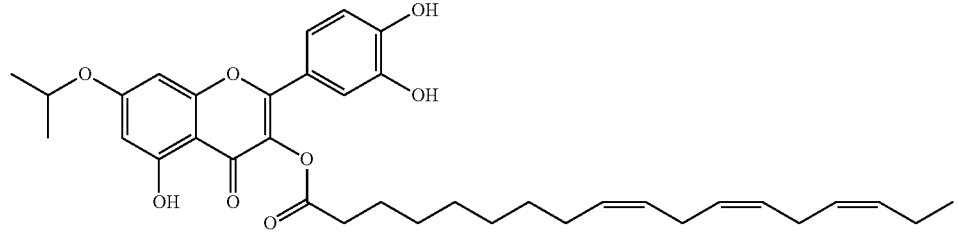
Q-3ALA-7OiP The pharmaceutical compositions, both for veterinary and for human use, useful according to the present invention comprise at least one compound having formula (I) as above defined, together with one or more pharmaceutically acceptable carriers and possibly other therapeutic ingredients. In certain preferred embodiments, active ingredients necessary in combination therapy may be combined in a single pharmaceutical composition for simultaneous administration.

As used herein, the term "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not to be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The pharmaceutical compositions can be administered in a suitable formulation to humans and animals by topical or systemic administration, including oral, rectal, nasal, buccal, ocular, sublingual, transdermal, topical, vaginal, parenteral (including subcutaneous, intra-arterial, intramuscular, intravenous, intradermal, intrathecal and epidural), intracisternal and intraperitoneal. It will be appreciated that the preferred route may vary with for example the condition of the recipient. The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Figure 1:
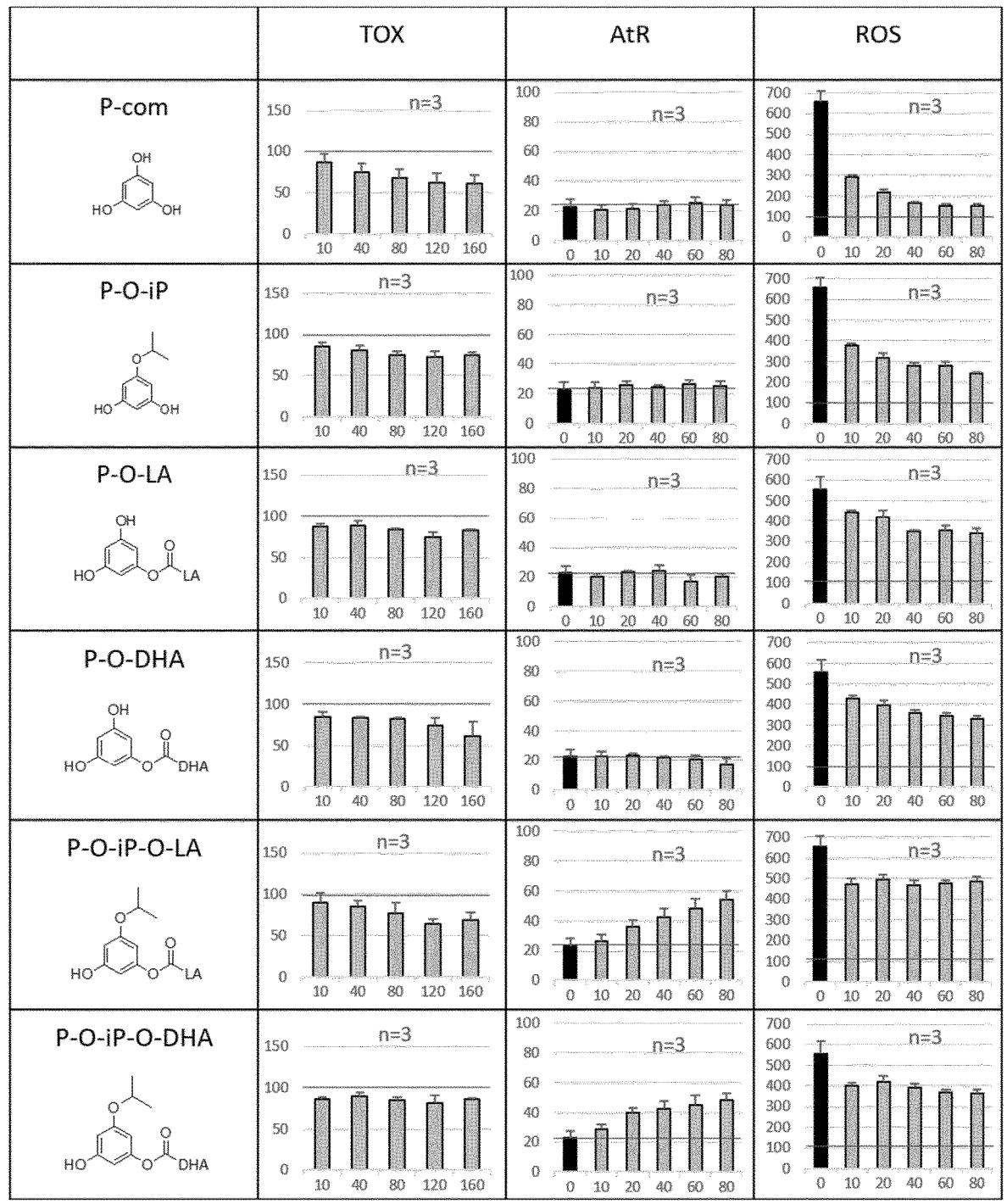
FIG. 1: Evaluation of biological activity of phloroglucinol derivatives (toxicity, trans-retinal protection, ROS scavenging in ARPE-19 cells).

The invention will be illustrated in the following non-limitative examples.

EXAMPLES

1—Synthesis of Lipophenolic Derivatives a) Material and Methods

All solvents were anhydrous reagents from commercial sources. Unless otherwise noted, all chemicals and reagents were obtained commercially and used without purification. Commercial quercetin, rutin or (+)-catechin were dried at 100° C. for 48 h under vacuum before use. The reactions were monitored by using TLC on plates that were pre-coated with silica gel 60 (Merck). The reaction components were visualized by using a 254 nm UV lamp, staining with acidic p-anisaldehyde solution followed by gentle heating. Purifications of synthesized compounds by column chromatography were performed on silica gel 40-63 mm. Melting points (Mp) were determined on a Stuart capillary apparatus and are uncorrected. NMR spectra were recorded at 300 or 500 MHz ($^1$H) and 75 or 126 MHz ($^{13}$C) on Bruker spectrometers. The chemical shifts are reported in parts per million (ppm, δ) relative to residual deuterated solvent peaks. The NMR spectra were assigned with the help of 2D NMR analysis (COSY, HSQC, and HMBC). The multiplicities are reported as follows: bs=broad signal, m=multiplet, s=singlet, d=doublet, t=triplet, q=quadruplet, qt=quintuplet, or combinations thereof. For the peak assignation, the following abbreviations were used: Ar=aromatic, Cq=quaternary carbon, iP=O-isopropyl, TIPS=triisopropylsilyl, CH═CH=aliphatic alkene, tBu=tert-butyl. Proton numbering was assigned according to IUPAC nomenclature. The possible inversion of two values in the NMR spectra is expressed by an asterisk.

The compounds are numbered as follows in their NMR spectra interpretation:

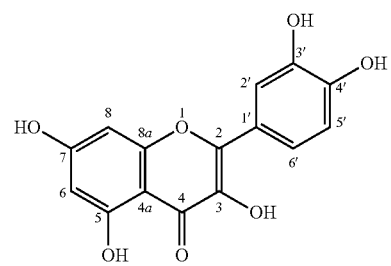

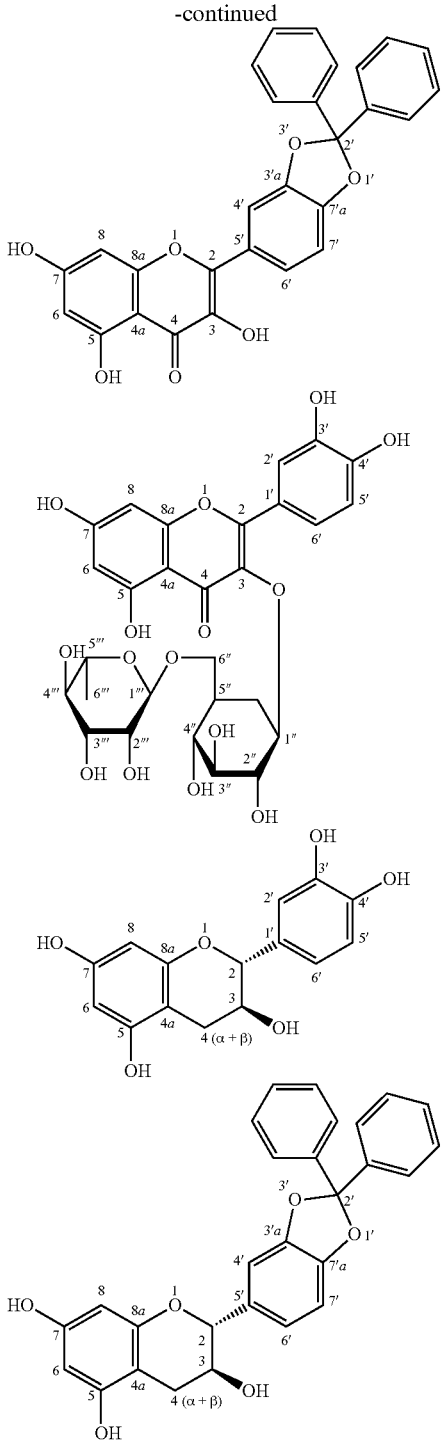

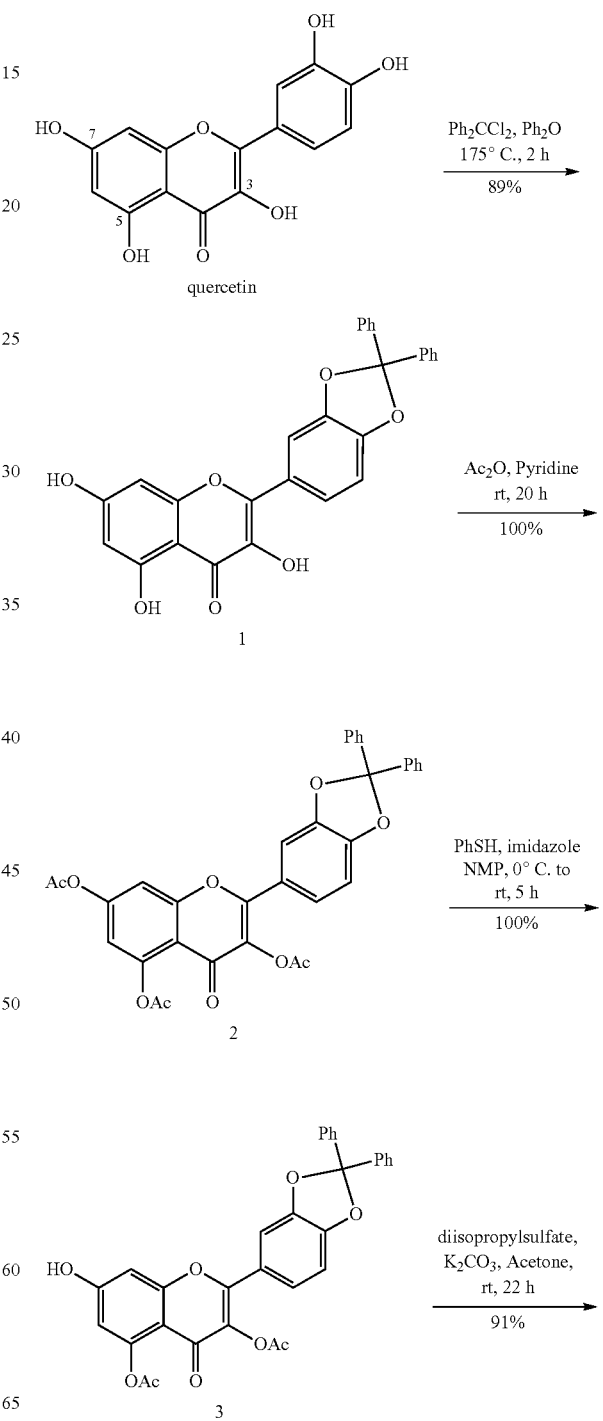

b) Synthesis of Quercetin Derivatives
Synthesis of Q-3FA-7OiP Series

Three quercetin derivatives carrying an isopropyl group on their position 7 and a fatty acid on the position 3, have been synthesized. The synthesis is described on schema 1 hereunder.

From quercetin as starting material, after protection of hydroxyl group of the catechol with a diphenyldioxol (compound 1), followed by an acetylation, compound 2 was obtained. A selective deprotection of the position 7 was performed to lead to compound 3 which was then alkylated on said position 7 with an isopropyl group (compound 4). After diphenyldioxol deprotection, silylated protection of catechol hydroxyls and deacetylation of remaining OH at 3 and 5 positions, compounds 7 was obtained. A coupling step with three different fatty acids (LA, DHA and ALA) and a final deprotection of silylated protecting groups lead to the three desired quercetin derivatives: Q-3LA-7OiP, Q-3DHA-7OiP and Q-3ALA-7OiP.

-continued

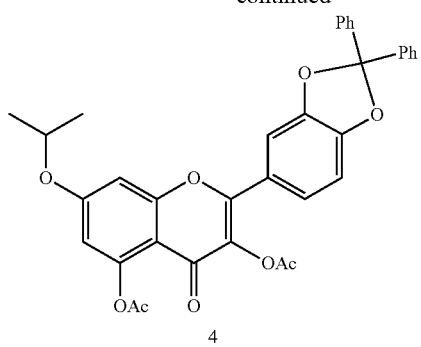
4

H₂, Pd(OH)₂
THF/EtOH,
20 h
47%

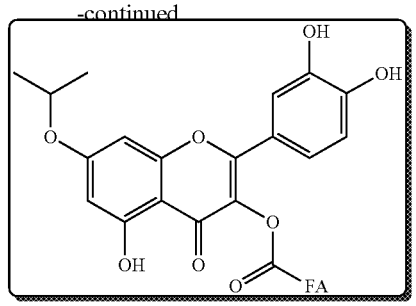

LA = 92%
DHA = 92%
ALA = 89%

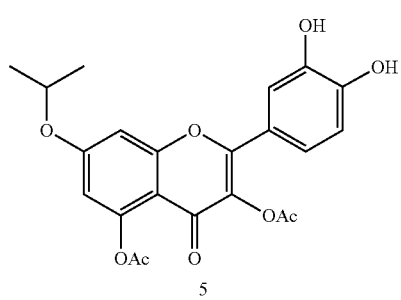
5

TIPS-OTf, NEt₃
THF, rt, 10 min
71%

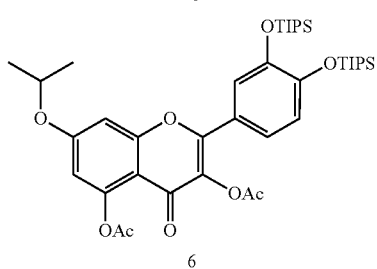
6

NH₃/MeOH
DCM, 0° C., 1 h
100%

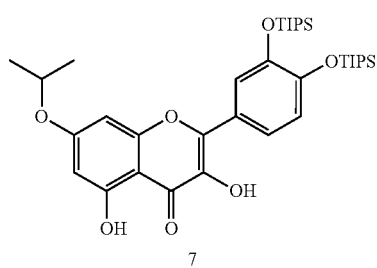
7

DCC, DMAP, FA
DCM, rt, 5 h
LA = 86%
DHA = 85%
ALA = 88%

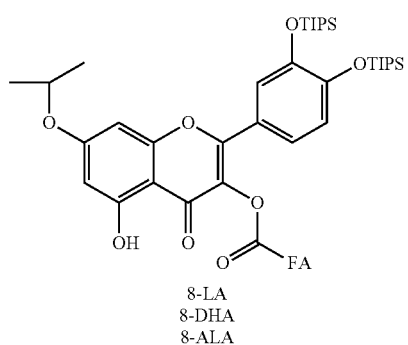
8-LA
8-DHA
8-ALA

Et₃N/3HF, THF
rt, 10-30 min

EXPERIMENTAL PART (9Z,12Z)-5-hydroxy-2-(3,4-dihydroxyphenyl)-7-isopropoxy-4-oxo-4H-chromen-3-yl octadeca-9,12-dienoate (Q-3LA-7OiP)

$R_f$ (pentane/EtOAc, 50:50)=0.67. Mp 123.4° C. $^1$H NMR (300 MHz, CDCl₃) δ 7.37-7.28 (m, 2H, H2', H6'), 6.90 (d, J=8.9 Hz, 1H, H5'), 6.36 (d, J=2.1 Hz, 1H, H8), 6.33 (d, J=2.1 Hz, 1H, H6), 5.46-5.24 (m, 4H, 2×CH═CH), 4.59 (qt, J=6.1 Hz, 1H, CHiP), 2.77 (t, J=5.7 Hz, 2H, H11"), 2.56 (t, J=7.6 Hz, 2H, H2"), 2.12-1.96 (m, 4H, H8", H14"), 1.77-1.59 (m, 2H, H3"), 1.37 (d, J=6.1 Hz, 6H, 2×CH₃iP), 1.34-1.18 (m, 14H, H4", H5", H6", H7", H15", H16", H17"), 0.88 (t, J=6.8 Hz, 3H, H18"). $^{13}$C NMR (75 MHz, CDCl₃) δ 175.89 (C4), 171.72 (C1"), 164.48 (C7), 161.71 (C5), 157.01 (C8a), 156.75 (C2), 147.45 (C3'), 143.72 (C4'), 130.53 (C3), 130.26 (CH═CH), 130.04 (CH═CH), 128.07 (CH═CH), 127.89 (CH═CH), 122.01 (C6'), 121.60 (C1'), 115.19 (C5'*), 114.96 (C2'*), 105.04 (C4a), 99.42 (C6), 93.95 (C8), 70.94 (CHiP), 33.91 (C2"), 31.50 (C16"), 29.56 (C15"*), 29.32 (C4"*), 29.13 (C5"*), 29.06 (C6"*), 28.98 (C7"*), 27.17 (2C, C8", C14"), 25.61 (C11"), 24.66 (C3"), 22.55 (C17"), 21.84 (2C, CH₃iP), 14.05 (C18").

(4Z,7Z,10Z,13Z,16Z,19Z)-5-hydroxy-2-(3,4-dihydroxyphenyl)-7-isopropoxy-4-oxo-4H-chromen-3-yl docosa-4,7,10,13,16,19-hexaenoate (Q-3DHA-7OiP)

$R_f$ (CH₂Cl₂/MeOH, 90:10)=0.65. Mp 116.8° C. $^1$H NMR (300 MHz, MeOD) δ 7.35 (d, J=2.1 Hz, 1H, H2'), 7.30 (dd, J=8.4, 2.1 Hz, 1H, H6'), 6.89 (d, J=8.4 Hz, 1H, H5'), 6.58 (d, J=2.1 Hz, 1H, H8), 6.33 (d, J=2.1 Hz, 1H, H6), 5.47-5.20 (m, 12H, 6×CH═CH), 4.73 (qt, J=6.3 Hz, 1H, CHiP), 2.95-2.73 (m, 10H, H6", H9", H12", H15", H18"), 2.69 (t, J=7.3 Hz, 2H, H2"), 2.48 (dd, J=12.7, 7.3 Hz, 2H, H3"), 2.04 (qt, J=7.2 Hz, 2H, H21"), 1.36 (d, J=6.3 Hz, 6H, 2×CH₃iP), 0.93 (t, J=7.2 Hz, 3H, H22"). $^{13}$C NMR (75 MHz, MeOD) δ 177.22 (C4), 171.93 (C1"), 165.95 (C7), 162.93 (C5), 158.68 (C8a*), 158.61 (C2*), 150.44 (C3'), 146.68 (C4'), 132.76 (CH═CH), 131.62 (C3), 130.63 (2C, CH═CH), 129.40 (CH═CH), 129.15 (2C, CH═CH), 129.08 (2C, CH═CH), 128.92 (CH═CH), 128.69 (2C, CH═CH), 128.19 (CH═CH), 122.30 (C6'), 121.97 (C1'), 116.51 (C5'*), 116.34 (C2'*), 105.95 (C4a), 100.32 (C6), 94.83 (C8), 72.18 (CHiP), 34.71 (C2"), 30.69 (C6"*), 26.57 (2C, C9"*, C12"*), 26.40 (2C, C15"*, C18"*), 23.69 (C3"), 22.14 (2C, CH₃iP), 21.45 (C21"), 14.59 (C22").

(9Z,12Z,15Z)-5-hydroxy-2-(3,4-dihydroxyphenyl)-7-isopropoxy-4-oxo-4H-chromen-3-yl octadeca-9,12,15-trienoate (Q-3ALA-7OiP)

$R_f$ (pentane/EtOAc, 50:50)=0.69. Mp 129.8° C. $^1$H NMR (300 MHz, MeOD) δ 7.35 (d, J=2.2 Hz, 1H, H2'), 7.30 (dd, J=8.4, 2.2 Hz, 1H, H6'), 6.89 (d, J=8.4 Hz, 1H, H5'), 6.59 (d, J=2.2 Hz, 1H, H8), 6.33 (d, J=2.2 Hz, 1H, H6), 5.47-5.20 (m, 6H, 3×CH=CH), 4.73 (qt, J=6.1 Hz, 1H, CHiP), 2.89-2.73 (m, 4H, H11", H14"), 2.63 (t, J=7.3 Hz, 2H, H2"), 2.15-1.99 (m, 4H, H8", H17"), 1.70 (qt, J=7.3 Hz, 2H, H3"), 1.37 (d, J=6.1 Hz, 6H, 2×CH$_3$iP), 1.41-1.25 (m, 8H, H4", H5", H6", H7"), 0.95 (t, J=7.5 Hz, 3H, H18"). $^{13}$C NMR (75 MHz, MeOD) δ 177.23 (C4), 172.51 (C1"), 165.92 (C7), 162.91 (C5), 158.69 (C8a*), 158.60 (C2*), 150.47 (C3'), 146.66 (C4'), 132.71 (CH=CH), 131.59 (C3), 131.13 (CH=CH), 129.24 (CH=CH), 129.17 (CH=CH), 128.83 (CH=CH), 128.24 (CH=CH), 122.23 (C6'), 121.90 (C1'), 116.47 (C5'*), 116.26 (C2'*), 105.88 (C4a), 100.28 (C6), 94.73 (C8), 72.10 (CHiP), 34.63 (C2"), 30.63 (C4"*), 30.20 (C5"*), 30.14 (C6"*), 29.99 (C7"*), 28.15 (C8"), 26.52 (C11"), 26.40 (C14"), 25.81 (C3"), 22.14 (2C, CH$_3$iP), 21.48 (C17"), 14.66 (C18").

Synthesis of Q-3FA-5OiP Series

Three quercetin derivatives carrying an isopropyl group on their position 5 and a fatty acid on the position 3, have been synthesized. The synthesis is described on schema 2 hereunder.

Schema 2: Synthesis of Q-3FA-5OiP

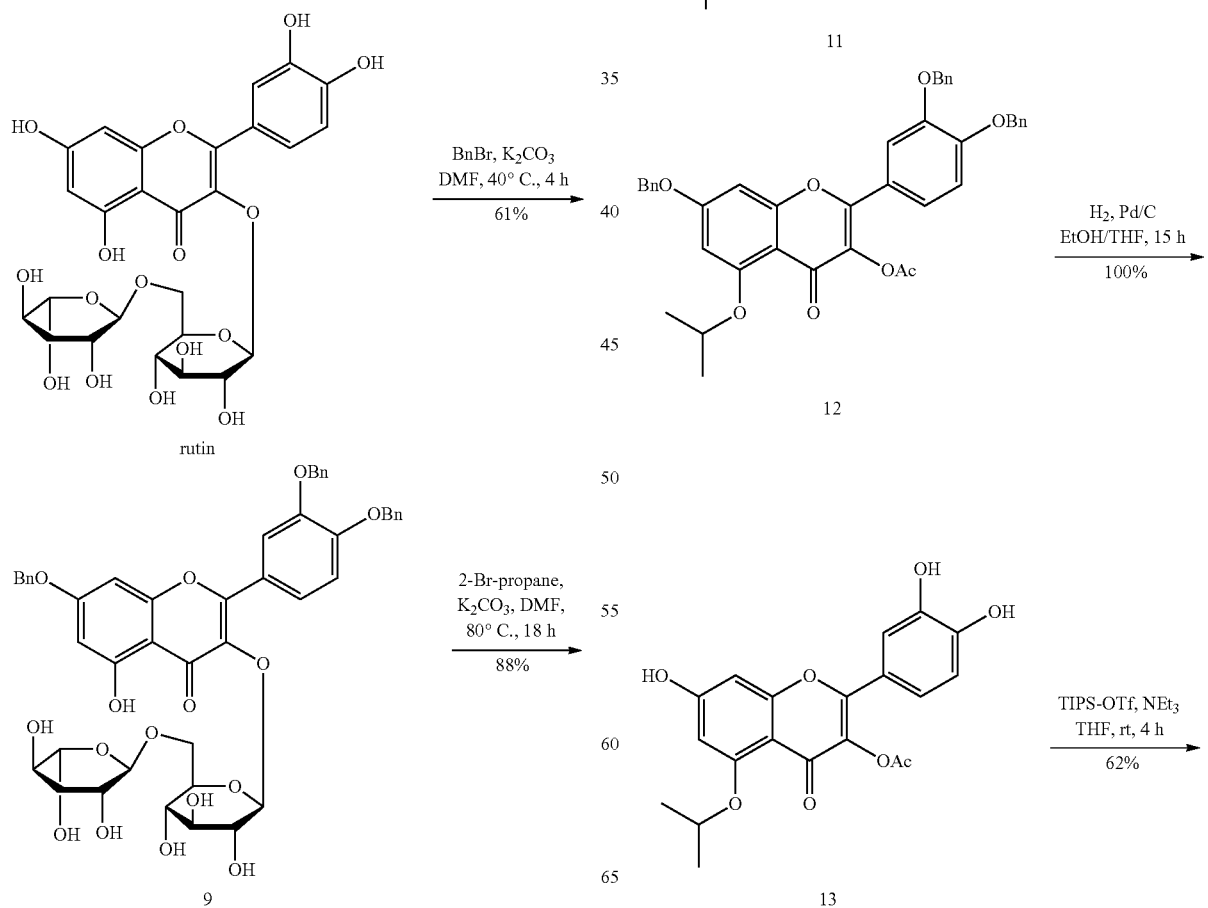

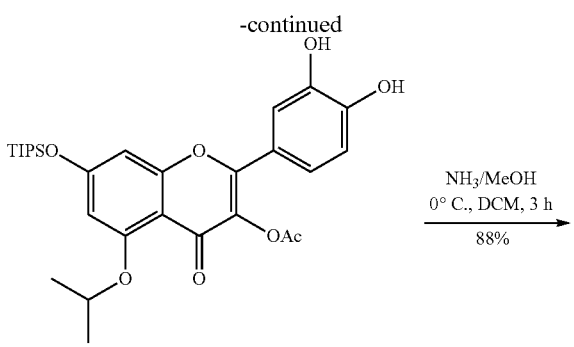

14

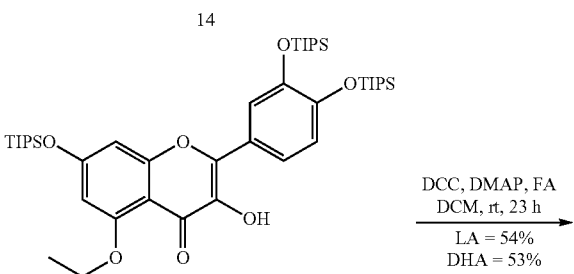

15

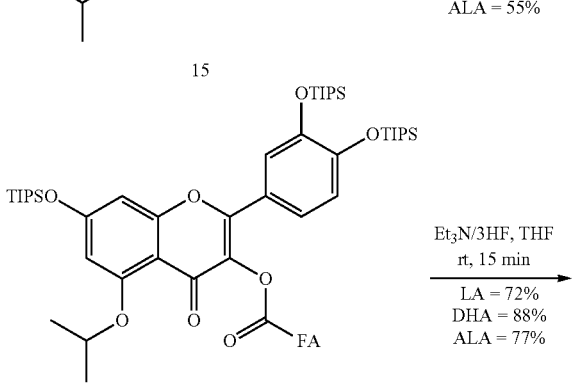

16-LA
6-DHA
16-ALA

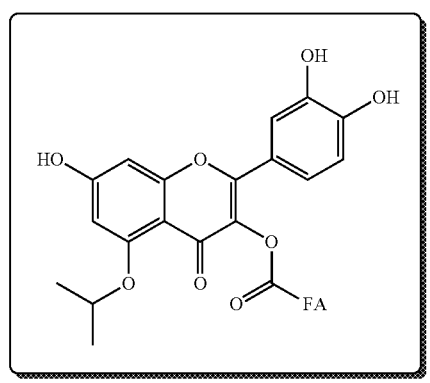

The synthesis starts from rutin, a natural quercetin diglycoside. Hydroxyl groups on position 7 and on the catechol moiety are first benzylated and the compound 9 is obtained. The free hydroxyl group at the 5 position is then etherified with an isopropyl group to lead to compound 10. Then, the diglycoside is removed in acidic conditions and the resulted compound 11 is acetylated to afford compound 12. A hydrogenation step allows the removal of benzyl group (compound 13) replaced by silylated protective groups to give compound 14 which is deacetylated with methanolic ammonia. The resulted compound 15 is then engaged in a coupling step with three fatty acids (LA, DHA and ALA) to give compounds 16-LA, 16-DHA and 16-ALA respectively. A final step of deprotection affords the three compounds of interest: Q-3LA-5OiP, Q-3DHA-5OiP and Q-3ALA-5OiP.

EXPERIMENTAL PART (9Z,12Z)-7-hydroxy-2-(3,4-dihydroxyphenyl)-5-isopropoxy-4-oxo-4H-chromen-3-yl octadeca-9,12-dienoate (Q-3LA-5OiP)

$R_f$ (CH$_2$Cl$_2$/MeOH, 90:10)=0.53. Mp 84.2° C. $^1$H NMR (300 MHz, MeOD) δ 7.32 (d, J=2.2 Hz, 1H, H2'), 7.26 (dd, J=8.4, 2.2 Hz, 1H, H6'), 6.88 (d, J=8.4 Hz, 1H, H5'), 6.49 (d, J=2.0 Hz, 1H, H8), 6.42 (d, J=2.0 Hz, 1H, H6), 5.42-5.24 (m 4H, 2×CH═CH), 4.65 (qt, J=6.0 Hz, 1H, CHiP), 2.76 (t, J=5.8 Hz, 2H, H11"), 2.63 (t, J=7.3 Hz, 2H, H2"), 2.12-1.98 (m, 4H, H8", H14"), 1.69 (qt, J=7.0 Hz, 2H, H3"), 1.41 (d, J=6.0 Hz, 6H, CH$_3$iP), 1.38-1.23 (m, 14H, H4", H5", H6", H7", H15", H16", H17"), 0.88 (t, J=6.8 Hz, 3H, H18"). $^{13}$C NMR (75 MHz, MeOD) δ 173.05 (C4), 172.76 (C1"), 164.94 (C7), 161.12 (C5), 160.66 (C8a), 155.76 (C2), 149.89 (C3'), 146.56 (C4'), 133.54 (C3), 130.92 (2C, CH═CH), 129.06 (2C, CH═CH), 122.21 (C1'), 121.80 (C6'), 116.39 (C5'), 116.04 (C2'), 108.90 (C4a), 99.83 (C6), 96.18 (C8), 73.17 (CHiP), 34.73 (C2"), 32.66 (C16"), 30.67 (C4"*), 30.47 (C5"*), 30.27 (C6"*), 30.17 (C7"*), 30.11 (C15"*), 28.15 (2C, C8", C14"), 26.53 (C11"), 25.79 (C3"), 23.64 (C17"), 21.95 (2C, CH$_3$iP), 14.46 (C18").

(4Z,7Z,10Z,13Z,16Z,19Z)-7-hydroxy-2-(3,4-dihydroxyphenyl)-5-isopropoxy-4-oxo-4H-chromen-3-yl docosa-4,7,10,13,16,19-hexaenoate (Q-3DHA-5OiP)

$R_f$ (CH$_2$Cl$_2$/MeOH, 90:10)=0.50. Mp 112.4° C. $^1$H NMR (300 MHz, MeOD) δ 7.32 (d, J=2.2 Hz, 1H, H2'), 7.26 (dd, J=8.4, 2.2 Hz, 1H, H6'), 6.88 (d, J=8.4 Hz, 1H, H5'), 6.50 (d, J=2.1 Hz, 1H, H8), 6.42 (d, J=2.1 Hz, 1H, H6), 5.50-5.19 (m, 12H, 6×CH═CH), 4.66 (qt, J=6.0 Hz, 1H, CHiP), 2.92-2.65 (m, 12H, H2", H6", H9", H12", H15", H18"), 2.52-2.45 (m, 2H, H3"), 2.14-1.97 (m, 2H, H21"), 1.41 (d, J=6.0 Hz, 6H, 2×CH$_3$iP), 0.94 (t, J=7.5 Hz, 3H, H22"). $^{13}$C NMR (75 MHz, MeOD) δ 172.97 (C4), 172.18 (C1"), 164.98 (C7), 161.15 (C5), 160.68 (C8a), 155.73 (C2), 149.91 (C3'), 146.58 (C3), 133.58 (C3), 132.75 (CH═CH), 130.52 (2C, CH═CH), 129.39 (CH═CH), 129.14 (2C, CH═CH), 129.09 (2C, CH═CH), 128.91 (CH═CH), 128.84 (2C, CH═CH), 128.20 (CH═CH), 122.22 (C1'), 121.86 (C6'), 116.42 (C5'), 116.06 (C2'), 108.94 (C4a), 99.89 (C6), 96.21 (C8), 73.21 (CHiP), 34.79 (C2"), 26.56 (4C, C6", C9", C12", C15"), 26.41 (C18"), 23.66 (C3"), 21.96 (2C, CH$_3$iP), 21.48 (C21"), 14.66 (C22").

(9Z,12Z,15Z)-7-hydroxy-2-(3,4-dihydroxyphenyl)-5-isopropoxy-4-oxo-4H-chromen-3-yl octadeca-9,12,15-trienoate (Q-3ALA-5OiP)

$R_f$ (CH$_2$Cl$_2$/MeOH, 90:10)=0.43. Mp 77.0° C. $^1$H NMR (300 MHz, MeOD) δ 7.32 (d, J=2.1 Hz, 1H, H2'), 7.25 (dd, J=8.4, 2.1 Hz, 1H, H6'), 6.88 (d, J=8.4 Hz, 1H, H5'), 6.49 (d, J=2.0 Hz, 1H, H8), 6.42 (d, J=2.0 Hz, 1H, H6), 5.44-5.20 (m, 6H, 6×CH═CH), 4.65 (qt, J=6.0 Hz, 1H, CHiP), 2.80 (t, J=5.8 Hz, 4H, H11", H14"), 2.63 (t, J=7.3 Hz, 2H, H2"), 2.13-1.99 (m, 4H, H8", H17"), 1.70 (qt, J=7.3 Hz, 2H, H3"), 1.41 (d, J=6.0 Hz, 6H, 2×CH$_3$iP), 1.38-1.23 (m, 8H, H4", H5", H6", H7"), 0.95 (t, J=7.5 Hz, 3H, H18"). $^{13}$C NMR (75

MHz, MeOD) δ 173.04 (C4"), 172.79 (C1"), 164.93 (C7), 161.12 (C5), 160.66 (C8a), 155.77 (C2), 149.87 (C3'), 146.56 (C4'), 133.55 (C3), 132.70 (CH=CH), 131.13 (CH=CH), 129.22 (CH=CH), 129.17 (CH=CH), 128.80 (CH=CH), 128.23 (CH=CH), 122.24 (C1'), 121.80 (C6'), 116.40 (C5'), 116.06 (C2'), 108.94 (C4a), 99.90 (C6), 96.21 (C8), 73.20 (CHiP), 34.73 (C2"), 30.65 (C4"*), 30.26 (C5"*), 30.16 (C6"*), 30.10 (C7"*), 28.15 (C8"), 26.51 (C11"), 26.39 (C14"), 25.78 (C3"), 21.95 (2C, CH$_3$iP), 21.47 (C17"), 14.65 (C$_{18}$").

Synthesis of Q-3FA Series

Compounds Q-3LA and Q-3DHA, without isopropyl group, are synthesized from quercetin, first engaged in a coupling step with free fatty acid (LA and DHA) to give compounds 17-LA and 17-DHA wherein all hydroxyl groups are acylated by fatty acids. Then, an enzymatic selective deprotection is performed to give desired compounds wherein only position 3 is carrying a fatty acid.

Schema 3: Synthesis of Q-3FA

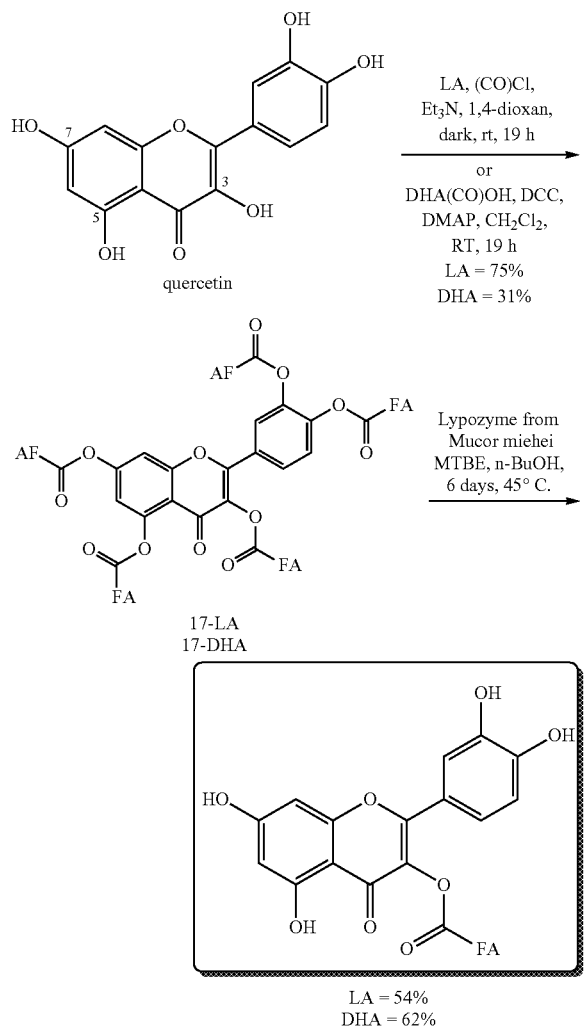

(9Z,12Z)-2-(3,4-dihydroxyphenyl)-5,7-dihydroxy-4-oxo-4H-chromen-3-yl octadeca-9,12-dienoate (Q-3LA)

R$_f$ (pentane/EtOAc, 50:50)=0.25. Mp 193.8° C. $^1$H NMR (500 MHz, MeOD) δ 7.33 (d, J=2.2 Hz, 1H, H2'), 7.28 (dd, J=8.4, 2.2 Hz, 1H, H6'), 6.89 (d, J=8.4 Hz, 1H, H5'), 6.43 (d, J=2.1 Hz, 1H, H8), 6.24 (d, J=2.1 Hz, 1H, H6), 5.41-5.27 (m, 4H, 2×CH=CH), 2.77 (t, J=6.5 Hz, 2H, H11"), 2.63 (t, J=7.3 Hz, 2H, H2"), 2.12-2.00 (m, 4H, H8", H14"), 1.70 (qt, J=7.3 Hz, 2H, H3"), 1.43-1.24 (m, 14H, H4", H5", H6", H7", H15", H16", H17"), 0.89 (t, J=6.8 Hz, 3H, H18"). $^{13}$C NMR (126 MHz, MeOD) δ 177.22 (C4), 172.55 (C1"), 166.30 (C7), 163.13 (C5), 158.68 (C8a), 158.45 (C2), 150.37 (C3'), 146.64 (C4'), 131.43 (C3), 130.91 (CH=CH), 130.90 (CH=CH), 129.07 (CH=CH), 129.06 (CH=CH), 122.13 (C6'), 121.97 (C1'), 116.45 (C5'), 116.18 (C2'), 105.27 (C4a), 100.14 (C6), 95.03 (C8), 34.61 (C2"), 32.65 (C16"), 30.63 (C4"*), 30.48 (C5"*), 30.19 (C6"*), 30.13 (C7"*), 29.98 (C15"*), 28.15 (C8"), 28.12 (C14"), 26.53 (C11"), 25.80 (C3"), 23.63 (C17"), 14.42 (C18").

(4Z,7Z,10Z,13Z,16Z,19Z)-2-(3,4-dihydroxyphenyl)-5,7-dihydroxy-4-oxo-4H-chromen-3-yl docosa-4,7,10,13,16,19-hexaenoate (Q-3DHA)

R$_f$ (CH$_2$Cl$_2$/MeOH, 95:5)=0.20. Mp 191.3° C. $^1$H NMR (300 MHz, MeOD) δ 7.34 (d, J=2.2 Hz, 1H, H2'), 7.28 (dd, J=8.4, 2.2 Hz, 1H, H6'), 6.89 (d, J=8.4 Hz, 1H, H5'), 6.43 (d, J=2.1 Hz, 1H, H8), 6.24 (d, J=2.1 Hz, 1H, H6), 5.51-5.16 (m, 12H, 6×CH=CH), 2.89-2.74 (m, 10H, H6", H9", H12", H15", H18"), 2.70 (t, J=7.3 Hz, 2H, H2"), 2.48 (q, J=7.3 Hz, 2H, H3"), 2.04 (qt, J=7.5 Hz, 2H, H21"), 0.94 (t, J=7.5 Hz, 3H, H22"). $^{13}$C NMR (75 MHz, MeOD) δ 177.15 (C4), 171.95 (C1"), 166.27 (C7), 163.13 (C5), 158.67 (C8a), 158.38 (C2), 150.38 (C3'), 146.67 (C4'), 132.73 (CH=CH), 131.46 (C3), 130.61 (2C, CH=CH), 129.38 (3C, CH=CH), 129.12 (2C, CH=CH), 129.06 (CH=CH), 128.89 (CH=CH), 128.68 (CH=CH), 128.18 (CH=CH), 122.19 (C6'), 121.96 (C1'), 116.47 (C5'), 116.20 (C2'), 105.30 (C4a), 100.14 (C6), 95.04 (C8), 34.68 (C2"), 26.55 (4C, C6"*, C9"*, C12"*, C15"*), 26.39 (C18"*), 23.67 (C3"), 21.46 (C21"), 14.65 (C22").

c) Synthesis of Catechin Derivatives

Synthesis of C-3LA-7OiP and C-3LA-5OiP

The synthesis of compound C-3LA-5OiP and C-3LA-7OiP, carrying a linoleic acid on position 3 and an isopropyl group on position 7 or 5 is described on schema 4 above. The catechol moiety of the (+)-catechin is protected with a diphenyldioxol to give compound 18. An isopropyl group is then introduced on position 7 to afford compound 19 or in position 5 to afford compound 20. Both compounds are obtained in one step, separated on silicagel chromatography and then used separately. A hydrogenation step is then performed to remove the diphenyldioxol group on the catechol moiety (compounds 21 and 22 from compounds 19 and 20 respectively). A last coupling is then realized using linoleoyl chloride give the compounds C-3LA-7OiP and C-3LA-5OiP. Final compounds are obtained in small amount (mg), sufficiently for identification and evaluation.

Synthesis of C-3LA

C-3LA was obtained starting from catechin by acylation using linoleoyl chloride. Mono acylated C-3LA was isolated in small amount due to degradation issue.

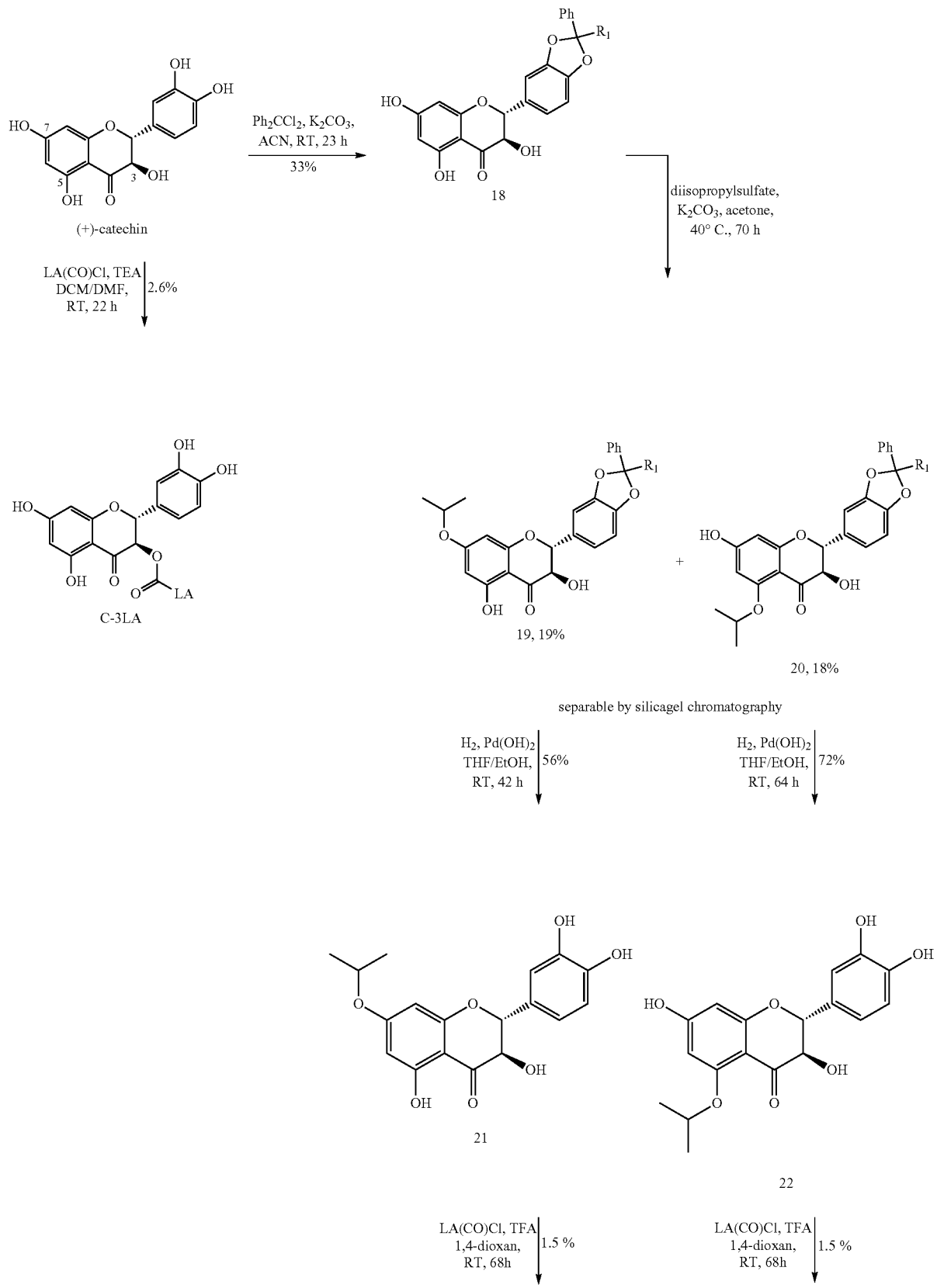
Schema 4: Synthesis of catechin derivatives

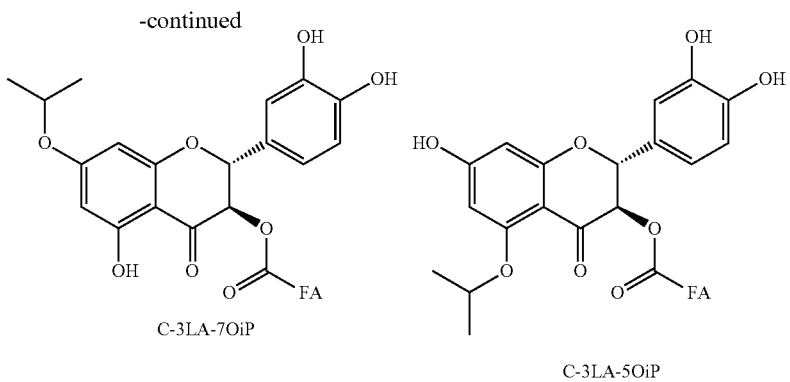

C-3LA-7OiP  C-3LA-5OiP

EXPERIMENTAL PART

(9Z,12Z)-(2R,3S)-2-(3,4-dihydroxyphenyl)-5-hydroxy-7-isopropoxy-chroman-3-yl octadeca-9,12-dienoate (C-3LA-7OiP)

$R_f$ (pentane/EtOAc, 50:50)=0.64. $^1$H NMR (300 MHz, MeOD) δ 6.79 (d, J=1.9 Hz, 1H, H2'), 6.76-6.65 (m, 2H, H5', H6'), 6.02-5.96 (m, 2H, H6, H8), 5.43-5.26 (m, 4H, 2×CH=CH), 5.21 (dd, J=12.2, 6.8 Hz, 1H, H3), 4.89-4.85 (m, 1H, H2), 4.46 (qt, J=6.0 Hz, 1H, CHiP), 2.89-2.73 (m, 3H, H4β, H11"), 2.62 (dd, J=16.3, 7.0 Hz, 1H, H4α), 2.21 (t, J=7.2 Hz, 2H, H2"), 2.06 (q, J=6.5 Hz, 4H, H8", H14"), 1.45 (qt, J=7.0 Hz, 2H, H3"), 1.39-1.14 (m, 20H, 2×CH$_3$iP, H4", H5", H6", H7", H15", H16", H17"), 0.90 (t, J=6.9 Hz, 3H, H18"). $^{13}$C NMR (75 MHz, MeOD) δ 174.61 (C1"), 159.13 (C7), 156.64 (2C, C8a, C5), 146.34 (2C, C3', C4'), 131.08 (C'), 130.99 (2C, CH=CH), 129.05 (2C, CH=CH), 119.47 (C6'), 116.11 (C5'), 114.73 (C2'), 100.80 (C4a), 97.17 (C6*), 95.86 (C8*), 79.69 (C2), 70.87 (2C, C3, CHiP), 35.23 (C2"), 32.68 (C16"), 30.71 (C4"*), 30.49 (C5"*), 30.19 (C6"*), 30.12 (C7"*), 29.90 (C15"*), 28.16 (2C, C8", C14"), 26.56 (C11"), 26.03 (C3"), 25.03 (C4), 23.65 (C17"), 22.43 (2C, CH$_3$iP), 14.45 (C18").

(9Z,12Z)-(2R,3S)-2-(3,4-dihydroxyphenyl)-7-hydroxy-5-isopropoxy-chroman-3-yl octadeca-9,12-dienoate (C-3LA-5OiP)

$R_f$ (pentane/EtOAc, 50:50)=0.63. $^1$H NMR (300 MHz, MeOD) δ 6.78 (d, J=1.9 Hz, 1H, H2'), 6.77-6.63 (m, 2H, H5', H6'), 6.04 (d, J=2.1 Hz, 1H, H8), 5.95 (d, J=2.1 Hz, 1H, H6), 5.44-5.25 (m, 4H, 2×CH=CH), 5.18 (dd, J=12.3, 6.9 Hz, 1H, H3), 4.86 (d, J=6.9 Hz, 1H, H2), 4.49 (qt, J=6.0 Hz, 1H, CHiP), 2.86-2.70 (m, 3H, H4β, H11"), 2.58 (dd, J=16.5, 7.1 Hz, 1H, H4α), 2.21 (t, J=7.2 Hz, 2H, H2"), 2.06 (q, J=6.5 Hz, 4H, H8", H14"), 1.45 (qt, J=7.3 Hz, 2H, H3"), 1.40-1.13 (m, 20H, 2×CH$_3$iP, H4", H5", H6", H7", H15", H16", H17"), 0.90 (t, J=6.8 Hz, 3H, H18"). $^{13}$C NMR (75 MHz, MeOD) δ 174.61 (C1"), 158.41 (C5*), 158.24 (C7*), 156.54 (C8a), 146.47 (C3'), 146.33 (C4'), 131.06 (C1'), 130.97 (2C, CH=CH), 129.06 (2C, CH=CH), 119.48 (C6'), 116.10 (C5'), 114.73 (C2'), 101.57 (C4a), 96.32 (C6*), 95.13 (C8*), 79.62 (C2), 71.23 (C3), 70.93 (CHiP), 35.22 (C2"), 32.68 (C16"), 30.68 (C4"*), 30.48 (C5"*), 30.17 (C6"*), 30.10 (C7"*), 29.88 (C15"*), 28.15 (2C, C8", C14"), 26.55 (C11"), 26.02 (C3"), 25.31 (C4), 23.64 (C17"), 22.51 (CH$_3$iP), 22.46 (CH$_3$iP), 14.45 (C18").

(9Z,12Z)-(2R,3S)-2-(3,4-dihydroxyphenyl)-5,7-dihydroxy-chroman-3-yl octadeca-9,12-dienoate (C-3LA)

$R_f$ (CH$_2$Cl$_2$/MeOH, 80:20)=0.80. $^1$H NMR (500 MHz, MeOD) δ 6.80 (d, J=2.0 Hz, 1H, H2'), 6.73 (d, J=8.1 Hz, 1H, H5'), 6.68 (dd, J=8.1, 2.0 Hz, 1H, H6'), 5.95 (d, J=2.2 Hz, 1H, H8), 5.89 (d, J=2.2 Hz, 1H, H6), 5.42-5.27 (m, 4H, 2×CH=CH), 5.20 (dd, J=12.4, 7.0 Hz, 1H, H3), 4.85 (d, J=7.0 Hz, 1H, H2), 2.84-2.74 (m. 3H, H4β, H11"), 2.60 (dd, J=16.3, 7.0 Hz, 1H, H4α), 2.20 (td, J=7.3, 1.8 Hz, 2H, H2"), 2.06 (q, J=6.9 Hz, 4H, H8", H14"), 1.50-1.40 (m, 2H, H3"), 1.40-1.11 (m, 14H, H4", H5", H6", H7", H15", H16", H17"), 0.90 (t, J=6.9 Hz, 3H, H18"). $^{13}$C NMR (126 MHz, MeOD) δ 174.61 (C1"), 158.17 (C7), 157.61 (C5), 156.60 (C8a), 146.45 (C3'*), 146.31 (C4'*), 131.15 (C1'), 130.98 (CH=CH), 130.93 (CH=CH), 129.09 (CH=CH), 129.04 (CH=CH), 119.53 (C6'), 116.10 (C5'), 114.79 (C2'), 99.72 (C4a), 96.49 (C8), 95.56 (C6), 79.68 (C2), 70.97 (C3), 35.22 (C2"), 32.65 (C16"), 30.68 (C4"*), 30.47 (C5"*), 30.17 (C6"*), 30.10 (C7"*), 29.90 (C15"*), 28.16 (C8"), 28.14 (C14"), 26.54 (C11"), 26.00 (C3"), 25.13 (C4), 23.61 (C17"), 14.41 (C18").

2—Evaluation of Biological Activity of Lipophenolic Derivatives a) Material and Methods Chemicals All lipophenols were dissolved in dimethylsulfoxide (DMSO) to prepare a stock solution at 80 mM. Hydrogen peroxide solution (H$_2$O$_2$, 30 wt. % in H$_2$O), α-tocopherol and all-trans-retinal were purchased from Sigma-Aldrich. 3-(4,5-dimethylthiazol-2-yl)-2,5-diphenyl tetrazolium bromide (MTT) was obtained from Sigma-Aldrich. N-retinylidene-N-retinylethanolamine (A2E) was synthesized as previously described by Parish et al., Proc. Natl. Acad. Sci. USA, 1998, 95, 14609-613. 2',7'-dichlorofluorescin diacetate (DCFDA) was purchased from Abcam and dissolved in DMSO to prepare stock solution at 20 mM. All stock solutions of lipophenols, α-tocopherol, all-trans-retinal, A2E and probe were stored at −20° C. in the dark.

Cell Culture

ARPE-19 cells (cells from the retinal pigment epithelium) were obtained from ATCC, and were grown following the instructions in Dulbecco's Modified Eagle's Medium (DMEM)/Ham F12 (GIBCO) containing 10% v/v fetal bovine serum (FBS) and 1% v/v penicillin/streptomycin under a humidified air (95%)/CO$_2$ (5%) atmosphere at 37° C. For experimental cell seeding and sub-culturing, cells were dissociated with 0.25% trypsin-EDTA, re-suspended in the culture medium and then plated at 1-3×10$^5$ cells/mL.

Cell Viability

Cell viability was determined by MTT colorimetric assay. Cells were incubated for 2 h with MTT reagent (0.5 mg/mL). During this incubation time, dehydrogenases of living cells reduced MTT to insoluble purple formazan, which was then dissolved in DMSO. The absorbance at 570 nm and 655 nm of individual wells was measured using a microplate reader (BioRad 550). The percentage of viable cells was calculated as [(OD570 sample–OD655 sample)/(OD570 control–OD655 control)]×100%.

Statistical Analyses for Biological Tests

The data are presented as means±SEM determined from at least three independent experiments. In each experiment, all conditions were done at least in quadruplicate.

Cytotoxicity of Lipophenols

ARPE-19 cells were plated into 96-well plates ($4\times10^4$ cells/well) and cultured for 24 h to reach confluence before lipophenol treatment. The cell cultures were treated with serum free medium containing the lipophenols at different concentrations (0-160 µM) for 24 h. Control cells were incubated with DMSO (0.2%). The viability of the cells was determined using a MTT colorimetric assay. All samples are expressed as percentage of viability compared to non-treated control cells (normalized at 100% survival).

Protection of Lipophenols Against all-Trans-Retinal

ARPE-19 cells were plated into 96-well plates ($4\times10^4$ cells/well) and cultured for 24 h to reach confluence before lipophenol treatment. The cell cultures were treated with serum free medium containing lipophenols at different concentrations (0-80 µM) for 1 h. Then all-trans-retinal was added to a final concentration of 15 µM for 4 h, before rinsing with medium. Control cells were incubated with DMSO (0.2%)±all-trans-retinal. The cell viability was determined 16-20 h later using a MTT colorimetric assay. All samples are expressed as percentage of viability compared to non-treated and exposed to all-trans-retinal control cells. Non-treated and non-exposed to all-trans-retinal control cells are normalized at 100% survival.

Protection of Lipophenols Against ROS Production

Reactive oxygen species (ROS) were measured in ARPE-19 cells with the probe DCFDA. The cell permeant reagent DCFDA is deacetylated by cellular esterases to dichlorofluorescein (DCFH), which can be oxidized by ROS into the fluorophore 2',7'-dichlorofluorescein (DCF). ARPE-19 cells were plated into black, opaque bottom 96-well plates ($4\times10^4$ cells/well) and cultured for 24 h to reach confluence before drug treatment. The cell cultures were incubated with 2 µM of DCFDA for 45 min in DMEM/F12 medium without phenol red+1% FBS. The cells were rinsed and incubated with medium containing lipophenols at different concentrations (0-80 µM) for 1 h. Then $H_2O_2$ was added to a final concentration of 600 µM for 4 h, followed by the measurement of DCF production by fluorescence spectroscopy with excitation wavelength at 485 nm and emission wavelength at 535 nm. Control cells were incubated with DMSO (0.2%) ±DCFDA±$H_2O_2$. All samples are expressed as percentage of ROS production compared to non-oxidized control cells (normalized at 100% of ROS production).

Protection of Lipophenols Against A2E

ARPE-19 cells were plated into 96-well plates ($4\times10^4$ cells/well) and cultured for 24 h to reach confluence before lipophenol treatment. The cell cultures were treated with serum free DMEM/F12 medium without phenol red containing lipophenols at different concentrations (0-80 µM) for 1 h. Then A2E was added to a final concentration of 20 µM for 6 h, before rinsing with medium. Control cells were incubated with DMSO (0.2%)+A2E. Cells were exposed to intense blue light (4600 LUX) for 30 min to induce phototoxicity of A2E and incubated at 37° C. The cell viability was determined 16-20 h later using a MTT colorimetric assay. All samples are expressed as percentage of viability compared to non-treated and exposed to A2E control cells. Non-treated and non-exposed to A2E control cells are normalized at 100% survival.

b) Results

Compounds according to the invention, from quercetin and catechin series, are compared to phloroglucinol compounds already known in the art.

Figure 2:
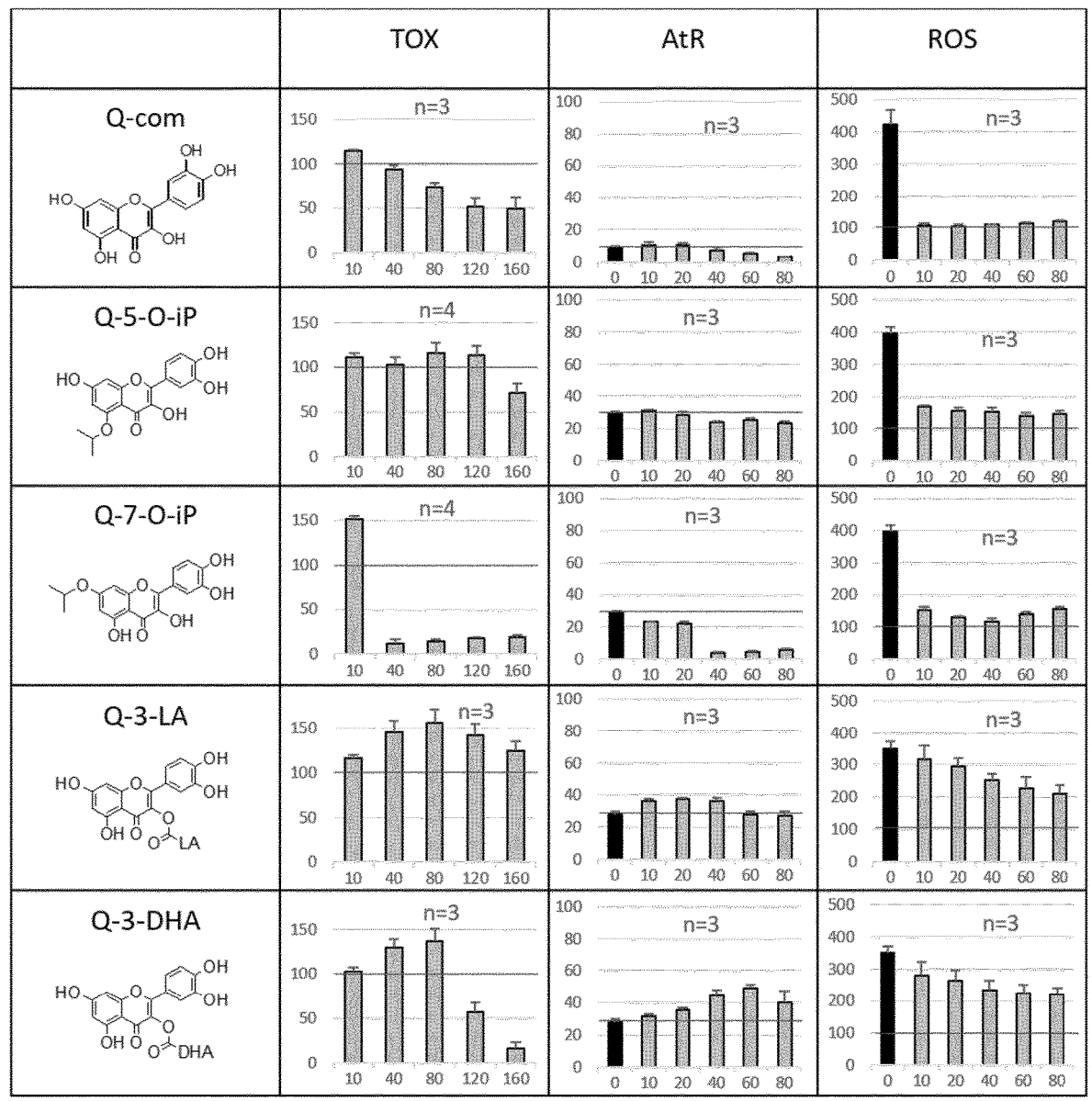
FIG. 2: Evaluation of biological activity of quercetin derivatives (toxicity, trans-retinal protection, ROS scavenging in ARPE-19 cells).
Figure 3:
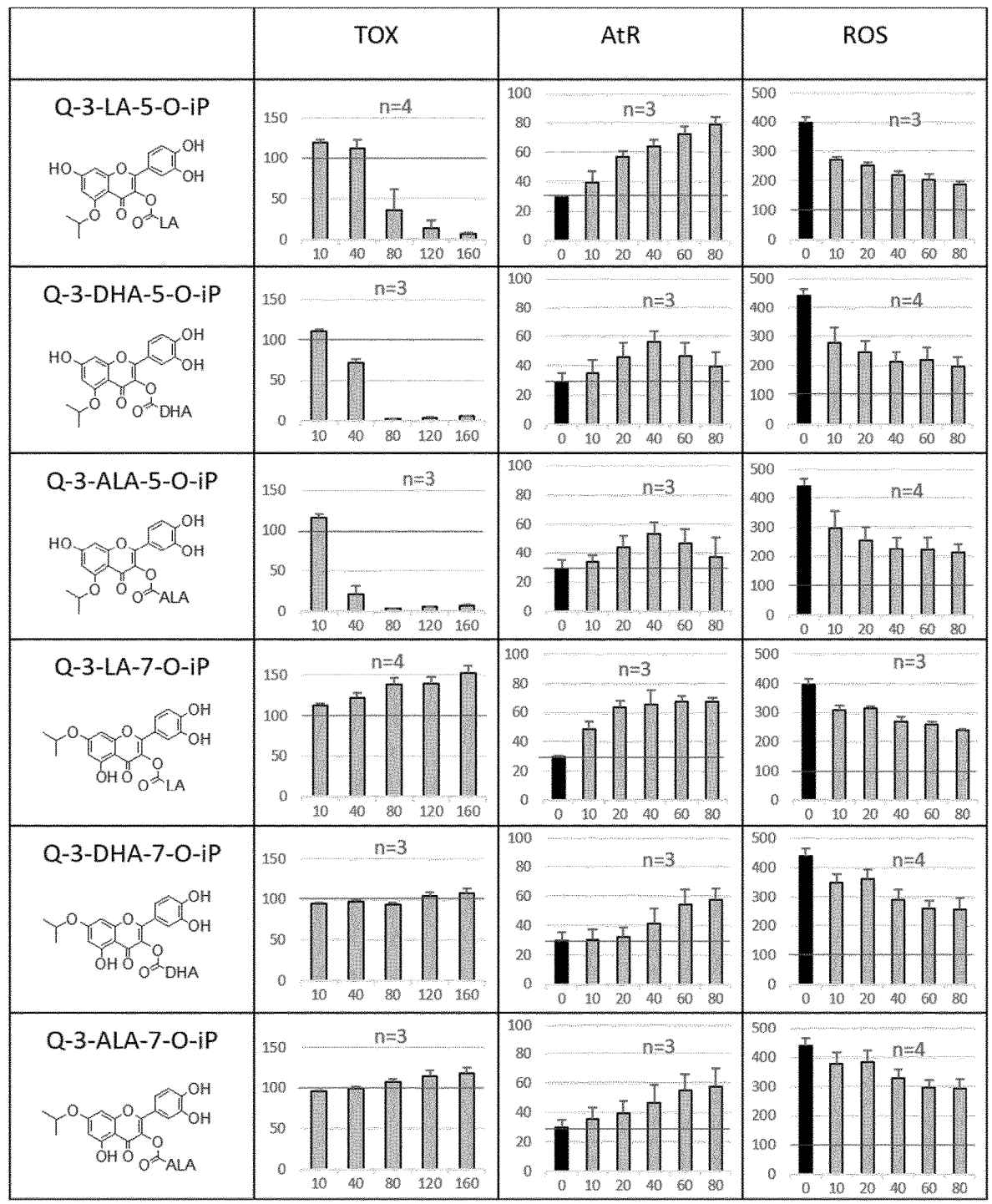
FIG. 3: Evaluation of biological activity of quercetin derivatives (toxicity, trans-retinal protection, ROS scavenging in ARPE-19 cells).
Figure 4:
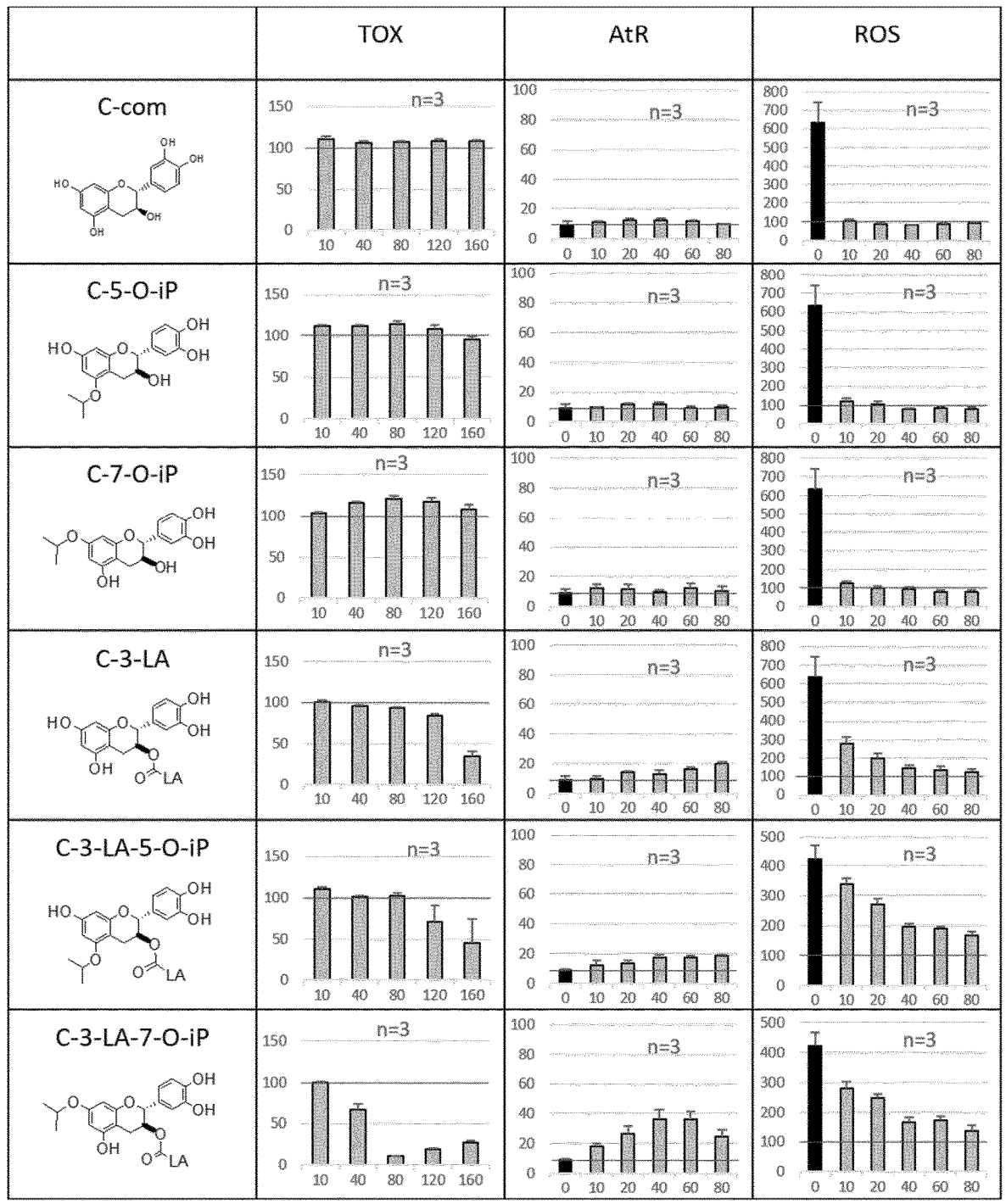
FIG. 4: Evaluation of biological activity of catechin derivatives (toxicity, trans-retinal protection, ROS scavenging in ARPE-19 cells).
Figure 5:
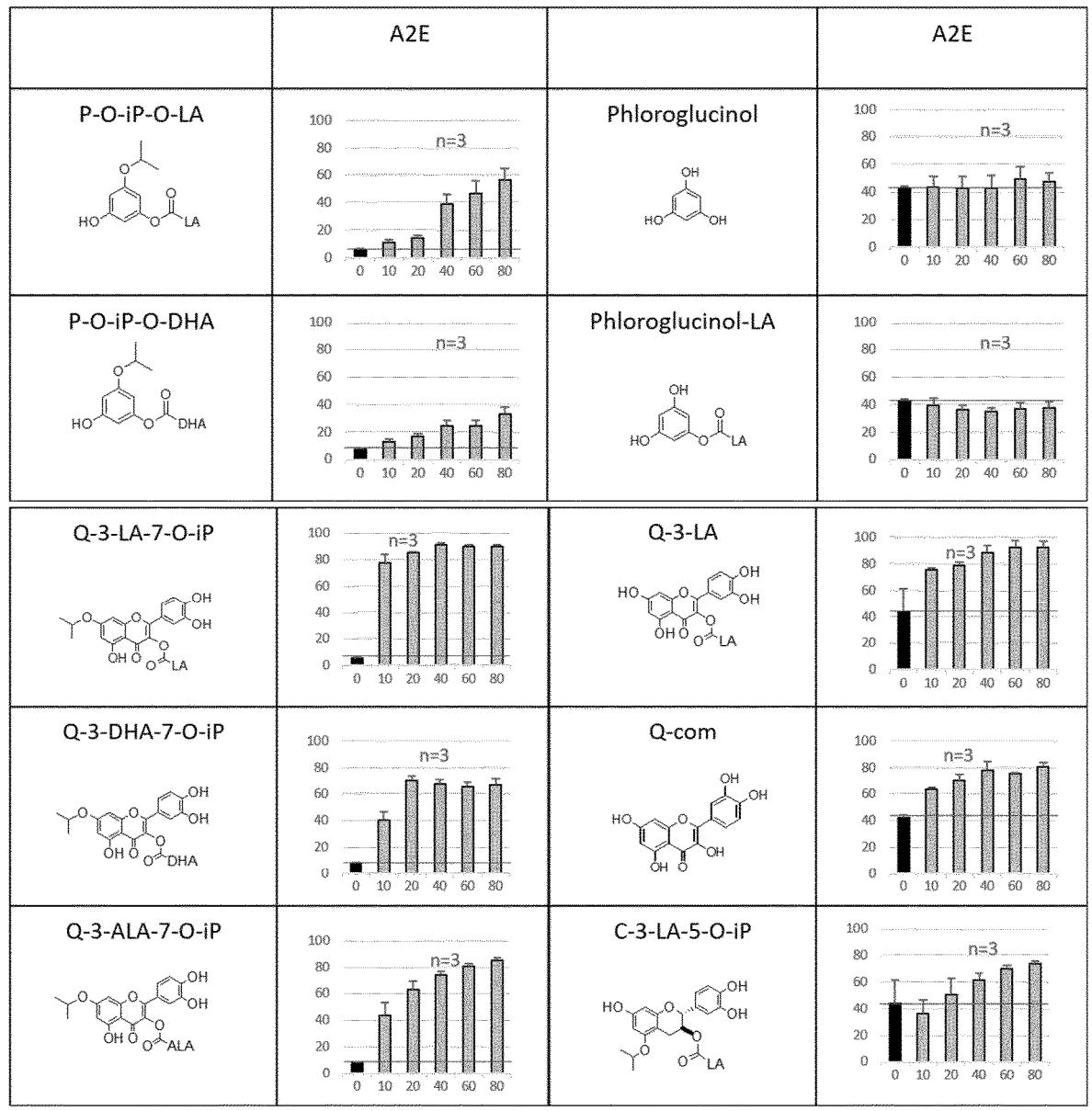
FIG. 5: Protection against photoactivated A2E in ARPE-19 cells

The discussion below is based on the results illustrated on FIGS. 1 to 5.

Cytotoxicity on ARPE-19 Cells

Results on the measurement of lipophenol toxicity will be discussed in % cell survival at a given lipophenol concentration compared to untreated cells. Any toxicity observed will give an indication of the cytotoxic concentration 50 (CC50) of the derivatives. Any concentration of lipophenol resulting in cell survival of less than 5% (zero survival) will be considered a highly toxic concentration.

Phloroglucinol Series (Comparative)

A slight toxicity is observed on ARPE-19 cells regardless of the phloroglucinol derivative. This toxicity does not appear to increase with phloroglucinol concentration (between 10 and 160 µM) and allows survival between 61% (commercial phloroglucinol) and 86% (P-OiP-ODHA) after incubation of a maximum concentration of 160 µM.

Catechin Series

Commercial catechin and both C-50iP and C-70iP derivative (which do not carry a fatty acid portion) show no toxicity for concentration until 160 µM. However, for compound carrying a linoleic acid C-3LA (without isopropyl group), the toxicity increases with a $CC_{50}$<160 µM. Similar toxicity is observed for compound C-3LA-50iP, suggesting that the introduction of an isopropyl group in position 5 does not allow to decrease the toxicity due to the linoleic acid. C-3LA-7OiP derivative ended in a toxicity much more important than C-3LA-5OiP with a cell survival equal to 0 starting from 80 µM.

Quercetin Series

Commercial quercetin induces cytotoxicity at a concentration below 160 µM with a $CC_{50}$ of approximately 120 µM. When substituted with isopropyl at position 5 (Q-50iP), this toxicity decreases to 72% survival at 160 µM. On the other hand, if isopropyl is introduced in position 7 (Q-70iP), a high toxicity is observed with zero survival as early as 40 µM of alkyl-phenol, suggesting an importance of isopropyl position in the toxicity of the alkylated-quercetin without a fatty acid moiety.

The introduction of a lipid chains on commercial quercetin lead to different toxicity profiles according to the type of fatty acid (LA or DHA). Thus, Q-3LA show a protective ability regardless cells since it increases survival up to 156% at 80 µM and remains protective even at 160 µM (124%). However, Q-3DHA is protective at low concentrations but is toxic at higher concentrations with a $CC_{50}$<160 µM.

For doubly substituted derivatives, the series having isopropyl in position 5 (Q-3FA-5OiP wherein FA=LA or DHA or ALA) induces cytotoxicity from 40-80 µM. Since Q-5OiP shows almost no toxicity, the induced toxicity seems to be due to the introduction of the lipid chain in position 3 when an isopropyl is at the position 5. The observed toxicity profile appears to be in the same direction as for Q-3FA (where FA=LA or DHA since the toxicity observed for the DHA derivative (Q-3DHA-5OiP, $CC_{50}$>40 µM) is higher than for the LA derivative (Q-3LA-50iP, $CC_{50}$<80 µM).

However, for the series having an isopropyl in position 7 (Q-3FA-7OiP where FA=LA or DHA or ALA) no toxicity is observed up to 160 µM, whatever the lipid introduced. These derivatives even seem to have a more or less important protective effect on the cells, going up to 153% survival for Q-3LA-7OiP at 160 µM. These protections are all the more surprising as the Q-70iP derivative (without fatty acid) shows a very important cytotoxicity even at low concentration, suggesting that the ester bond is stable in cellular medium during the duration of the test (24 h).

Conclusion on toxicity: This study shows that the toxicity profile of quercetin and catechin series differs from one derivative to another and seems to be related to the position of the substituents. Concerning the quercetin series, compounds with an isopropyl group in position 7 and a fatty acid in position 3 allow avoiding any toxicity until 160 µM.

Anti-Carbonyl Stress Activity: Protection Against Trans-Retinal Toxicity in ARPE-19 Cells.

The results on the measurement of anti-carbonyl stress activity will be discussed in % cell survival gain compared to cells stressed by trans-retinal (at 15 µM) and not treated with lipophenols. Any survival gain greater than +5% will be considered as a proven anti-carbonyl stress activity.

Phloroqlucinol Series (Comparative)

The need for double functionalization of phloroglucinol by isopropyl and lipid has already been demonstrated in order to obtain anti-carbonyl stress activity (patent WO2015162265A1, Brabet et al., New lipophenol compounds and uses thereof). The results reproduced here for the phloroglucinol series confirm the importance of the two groups. Indeed, commercial phloroglucinol, P-OiP as well as P-OLA and P-ODHA show no survival gain on cells in the presence of trans-retinal whatever the concentration used. On the other hand, the two derivatives P-OiP-OLA and P-OiP-ODHA increase cell survival in the presence of trans-retinal up to +31% and +25% respectively, at 80 µM.

Catechin Series

Like the phloroglucinol series, commercial catechin, C-50iP and C-70iP show no anti-carbonyl stress activity up to 80 µM. However, unlike the phloroglucinol series, C-3LA (isopropyl-free) shows slight cell protection up to +11% at 80 µM.

Concerning the double functionalization of catechins, C-3LA-5OiP shows moderate anti-carbonyl stress activity (+9% at 80 µM) while C-3LA-7OiP seems three times more protective at lower concentrations (+27% at 40 µM).

Compared to the lead of the phloroglucinol P-OiP-OLA series, C-3LA-7OiP has a higher anti-carbonyl stress activity at low doses (40 µM) increasing cell survival by +27% compared to +20% for phloroglucinol derivative.

Quercetin Derivatives

Like in the phloroglucinol and catechin series, the commercial quercetin and the isopropylated analogues (Q-50iP and Q-70iP, without fatty acid), did not show anti-carbonyl stress potency. Conversely, the two derivatives Q-3LA and Q-3DHA (without isopropyl group) show moderate cell protection against trans-retinal toxicity, with a maximum protection of +9% (obtained at 20 µM) and +21% (at 60 µM) respectively.

All quercetins doubly functionalized with isopropyl and fatty acid, Q-3FA-5OiP and Q-3FA-7OiP (where FA=LA or DHA or ALA) show interesting anti-carbonyl stress activity in the tested concentration range.

The Q-3FA-5OiP series (where FA=LA or DHA or ALA) where isopropyl is in position 5, has a protective effect against the toxicity of trans-retinal despite significant toxicity of lipophenols above 40 µM. The Q-3LA-5OiP shows the best anti-carbonyl stress properties with a maximum survival gain of +49% to 80 µM. Even at lower doses (40 µM, non-cytotoxic concentration) the Q-3LA-5OiP allows to reach a cellular survival increased by +34% which is much higher than that observed by the lead P-OiP-OLA at the same concentration (+20% survival). The Q-3DHA-5OiP and Q-3ALA-5OiP derivatives have a similar activity profile, since at low concentrations (up to 40 µM) they are protective but their beneficial effect is counteracted by their toxicity (from 60 µM). Thus at 40 µM the Q-3DHA-5OiP and Q-3ALA-5OiP allow a survival gain of +27% and +24% respectively, which is higher than the gain observed for the P-OiP-ODHA lead (+20% at 40 µM).

Concerning the series Q-3FA-70iP (where FA=LA or DHA or ALA) having isopropyl in position 7, the derivative showing the best anti-carbonyl stress activity is also the derivative LA: Q-3LA-70iP, which makes it possible to obtain a survival gain of +38% at 80 µM. Its protective activity seems to reach a limit value as early as 20 µM suggesting that this concentration would be sufficient to obtain the maximum anti-carbonyl stress activity of this derivative. For Q-3DHA-70iP, the maximum protection is reached less rapidly and it is necessary to increase the concentrations to observe the protective effect: +29% at 80 µM. This anti-carbonyl stress activity is however slightly higher than that observed for P-OiP-ODHA lead (+25% at 80 µM). Finally, for the Q-3ALA-7OiP derivative, the maximum observed survival gain is similar to that of Q-3DHA-7OiP (+29% at 80 µM). The higher value observed for Q-3LA-7OiP giving maximum anti-carbonyl stress activity is not reached for the two derivatives Q-3DHA-7OiP and Q-3ALA-7OiP suggesting that they may confer better cell protection against trans-retinal at higher concentrations since they show no toxicity up to 160 µM.

Conclusion on anti-carbonyl stress activity: These results show that compounds substituted by isopropyl only, do not present any anti-carbonyl stress activity. In some cases, derivative with only one fatty acid can lead to a slight protective effect against carbonyl stress. Best protective results are obtained for di-substituted (by isopropyl and fatty acid) derivative in quercetin series>catechin series and with 7-OiP close to 5-OiP activities, however 7-OiP series would be preferred due to toxicity issue of the 5-OiP series.

Antioxidant Activity: Reduction of ROS

The results on the measurement of antioxidant activity linked to the trapping of ROS (Reactive Oxygen Species) of lipophenols, will be discussed by comparing the gain of % of ROS production compared to non-stressed cells (to be as comparable as possible given the high variability of the % of ROS produced by cells stressed by hydrogen peroxide and not treated by lipophenols). We therefore consider that above +300% ROS, lipophenol derivatives do not have antioxidant activity. The lowest percentages of increase will therefore be representative of the most protective derivatives.

Phloroqlucinol Series (Comparative)

Measurement of the antioxidant activity of the phloroglucinol series shows that only commercial phloroglucinol can significantly reduce the production of ROS in stressed cells (+50% ROS at 80 µM). The mono-substituted P-OiP derivative retains part of the antioxidant activity with +142% ROS at 80 µM. The lipidic mono-substituted P-OLA and P-ODHA derivatives lose almost all of the antioxidant properties with +238% and +231% ROS at 80 µM respectively. Concerning the two di-substituted leads (P-OiP-OLA and P-OiP-ODHA), no antioxidant property could be observed based on ROS trapping (+300% of ROS whatever the lipophenol concentration).

Catechin Series

Measurement of the antioxidant activity of the catechin series shows that the derivatives provide good cell protection with a relatively small increase in the % ROS. The commercial catechin, C-5oiP and C-7oiP derivatives make it possible to fully protect cells with 0% increase in ROS from 20 µM. For C-3LA, the increase in ROS is also small with only +24% at 80 µM. The ROS trapping activity of the two di-substituted derivatives is slightly reduced but remains nevertheless interesting with only +67% of ROS for C-3LA-5OiP and +37% of ROS for C-3LA-7OiP at 80 µM.

Quercetin Derivatives

The measurement of the antioxidant activity of the quercetin series shows that all the derivatives have a more or less important antioxidant activity and allow reducing the production of ROS. Both Q-7oiP and Q-5oiP derivatives have good antioxidant properties with +31% ROS at 20 µM (non-cytotoxic concentration) and +46% ROS at 80 µM respectively.

The Q-3FA derivatives (where FA=LA or DHA) show a similar antioxidant profile ranging from +109 to +120% ROS (at 80 µM) suggesting that antioxidant activity does not depend on the type of lipid introduced.

Concerning the series of di-functionalized derivatives Q-3FA-5OiP (where FA=LA or DHA or ALA) having isopropyl in 5, the antioxidant activity profiles are similar whatever the lipid introduced in position 3 ranging from +88 to +114% of ROS at 80 µM. Similarly, for the series of di-functionalized derivatives Q-3FA-7OiP (where FA=LA or DHA or ALA) having isopropyl in 7, the profiles are similar whatever the fatty acid in position 3 with slightly weaker activities ranging from +141 to +192% of ROS at 80 µM. Although these antioxidant activities appear more moderate than those observed for commercial quercetin, they represent a maximum decrease in ROS production of 53% for the Q-3FA-7OiP series (where FA=LA or DHA or ALA) and 71% for the Q-3FA-5OiP series (where FA=LA or DHA or ALA) compared to stressed and untreated cells.

Conclusion on antioxidant activity: It appears from this study that three of the catechin derivatives have dual anti-carbonyl stress and antioxidant activity: C-3LA, C-3LA-5OiP and C-3LA-7OiP. Concerning the quercetin series, two mono-substituted derivatives have a double anti-carbonyl stress and antioxidant activity and are potentially interesting for the development of anti-COS: Q-3LA and Q-3DHA. In addition, the six di-functionalized quercetin derivatives have shown strong dual anti-carbonyl stress and antioxidant activity and are of interest for future development and/or in vivo evaluations: Q-3LA-5OiP, Q-3DHA-5OiP, Q-3ALA-5OiP, Q-3LA-7OiP, Q-3DHA-7OiP and Q-3ALA-7OiP. Due to their low toxicity, Q-3FA-7OiP derivatives (where FA=LA or DHA or ALA) with isopropyl at the 7 position are preferred in this study.

Protection Against Toxicity of Photoactivated A2E in ARPE-19 Cells:

Photoactivation of A2E leads to its oxidation and can generate cytotoxic derivatives, in particular carbonyl derivatives responsible for carbonyl stress. Results on lipophenol protection against photoactivated A2E toxicity will be discussed in % cell survival gain compared to cells stressed by A2E and not treated by lipophenols. This additional evaluation was not performed for all synthesized lipophenolic derivatives but only a selection of them to discuss the results obtained.

Concerning the series of phloroglucinol derivatives, the two leads P-OiP-OLA and P-OiP-ODHA (anti-carbonyl stress activities but without effectiveness in ROS trapping) were selected to evaluate their protection against toxicity induced by photoactivated A2E. For comparison, commercial phloroglucinol (no anti-carbonyl stress activity but strong anti-oxidative stress activity) and P-OLA (no anti-carbonyl stress activity but anti-oxidative stress activity) were also evaluated.

For catechin derivatives, C-3LA-5OiP being the least toxic and having shown both anti-carbonyl stress and anti-oxidative stress properties, its protection against photoactivated A2E induced toxicity was also evaluated.

Finally, for the quercetin series, the three derivatives having obtained the best double anti-carbonyl stress and anti-oxidative stress activities, and an absence of toxicity up to 160 µM, are Q-3LA-7OiP, Q-3DHA-7OiP and Q-3ALA-7OiP. They were therefore selected to evaluate their protection against photoactivated A2E induced toxicity. In order to serve as a comparison, commercial quercetin (without anti-carbonyl stress activity but with antioxidant activity) as well as Q-3LA (with low anti-carbonyl stress activity and good antioxidant activity) were also evaluated.

Phloroqlucinol Series (Comparative)

For commercial phloroglucinol and P-OiP, no cell protection could be observed. In contrast, for the two derivatives with anti-carbonyl stress activity P-OiP-OLA and P-OiP-ODHA, a survival gain of +52% and +25% respectively was observed at 80 µM of lipophenol. As these two derivatives do not have ROS trapping activity in the tests performed (unlike commercial phloroglucinol) it would seem that their protection against A2E toxicity could be linked to their anti-carbonyl stress activity.

Catechin Derivative

For C-3LA-5OiP having shown a double activity anti-carbonyl stress and antioxidant, it was observed a gain of survival of +30%. Even with moderate anti-carbonyl stress activity (+9% at 80 µM), this lipophenol is protective against A2E.

Quercetin Derivatives

Commercial quercetin shows a cell protection with a +36% survival gain from 40 µM, which seems to reach a plateau and no longer increase up to 80 µM. This protection against A2E does not seem related to the anti-carbonyl stress activity of commercial quercetin because it shows no cellular protection in the presence of trans-retinal at the concentrations evaluated. All quercetin derivatives tested are protective whether they are antioxidant or active against carbonyl stressor. Q-3LA having shown an anti-carbonyl stress activity and moderate antioxidant properties, allows to reach a +48% survival gain from 60 µM. The Q-3LA-7OiP derivative is the one allowing the best protection with a +86% survival gain from 40 µM. It seems to reach a maximum protection plateau from this concentration. The Q-3DHA-7OiP derivative also seems to reach a plateau as early as 20 µM with a survival gain of +62%. The Q-3ALA-7OiP derivative seems to require higher concentrations to confer good cell protection and allow a survival gain of +77% at 80 µM. Concerning the quercetin derivative series, part of the cells protection against photoactivated A2E is conferred by the skeleton (and potentially its antioxidant properties) but in order to exacerbate this protection, the activity against carbonyl stress seems essential, allowing to pass from a survival gain of +36% to +86%.

All these biological results demonstrate that the double substituted flavonoid derivatives, preferably the double substituted quercetin, and even more preferably quercetin carrying an isopropyl group on position 7 and a fatty acid DHA or LA on position 3, are the most efficient compounds against both carbonyl and oxidative stresses.

The invention claimed is:

1. A method for preventing and/or treating a disease or disorder involving both carbonyl and oxidative stresses, comprising the administration to a subject in need thereof of a compound of formula (I):

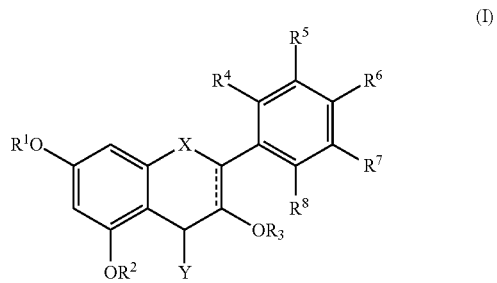

wherein
$R^1$ and $R^2$ are each independently selected from the group consisting of H or $(C_1-C_6)$alkyl, provided that one of $R^1$ or $R^2$ is H and the other is not H,
$R^3$ is selected from the group consisting of —C(O)—$(C_{11}-C_{21})$alkyl or —C(O)—$(C_{11}-C_{21})$alkenyl,
$R^4$ to $R^8$ are identical or different and are each independently selected from the group consisting of H, OH, $O(C_1-C_6)$alkyl, —C(O)—$(C_{11}-C_{21})$alkyl or —C(O)—$(C_{11}-C_{21})$alkenyl,
X is selected from the group consisting of O, S, $CH_2$ or NH,
Y is oxo group,
⸺ is a double bond,
or its pharmaceutically acceptable salts, racemates, diastereoisomers, enantiomers or mixtures thereof.

2. The method according to claim 1, wherein at least two of $R^4$ to $R^8$ are OH and the others are H in the compound of formula (I).

3. The method according to claim 1, wherein X is O in the compound of formula (I).

4. The method according to claim 1, wherein the compound has the following formula (II):

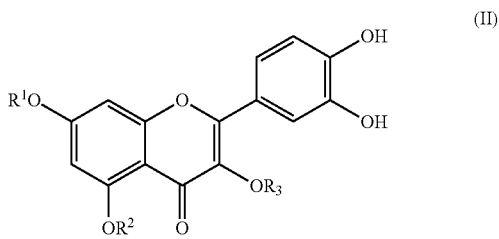

or its pharmaceutically acceptable salts, racemates, diastereoisomers, enantiomers or mixtures thereof, wherein $R^1$, $R^2$ and $R^3$ are as defined in claim 1.

5. The method according to claim 1, wherein:
$R^1$ is $(C_1-C_6)$ alkyl and $R^2$ is H or $R^2$ is $C_1-C_6$ alkyl and $R^1$ is H in the compound of formula (I).

6. The method according to claim 1, wherein $R^1$ is isopropyl group, and $R^2$ is H in the compound of formula (I).

7. The method according to claim 1, wherein $R_3$ is a linear —CO—$(C_{15}-C_{21})$alkenyl chain in the compound of formula (I).

8. The method according to claim 1, wherein $R_3$ is selected from the group consisting of:

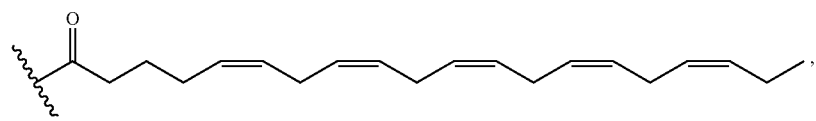

(EPA)

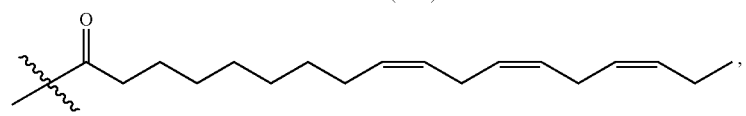

(ALA)

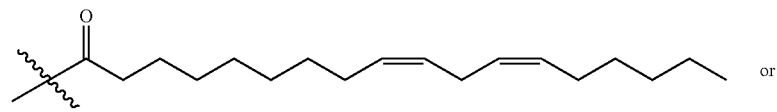

(LA) or

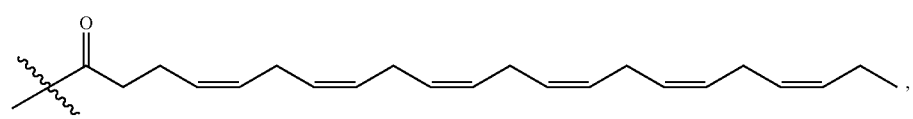

(DHA)

in the compound of formula (I).

9. The method according to claim 1, wherein the compound is selected from the group consisting of:
Q-3LA-5OiP
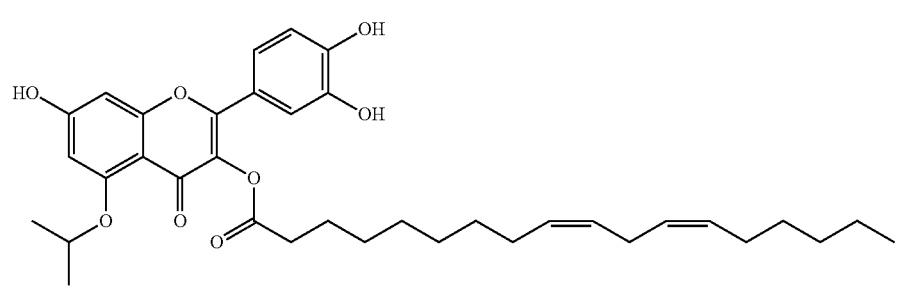
Q-3DHA-5OiP
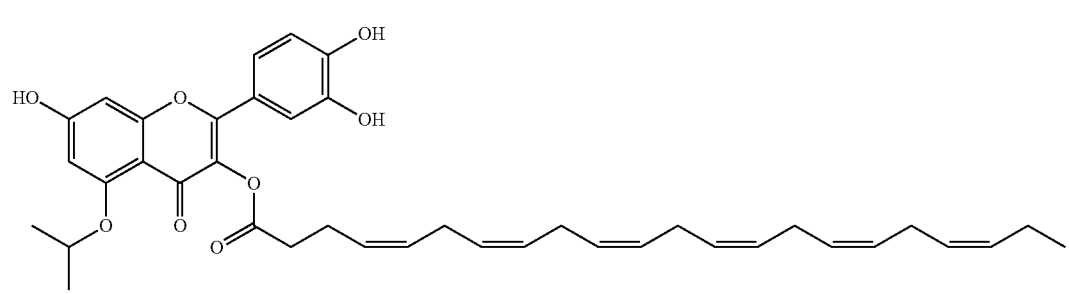
Q-3ALA-5OiP
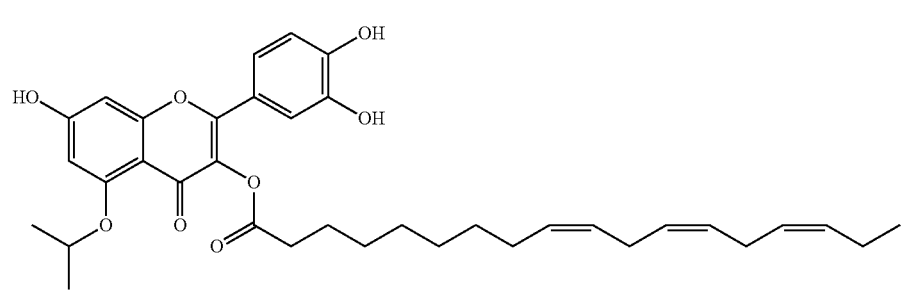
Q-3DHA-7OiP
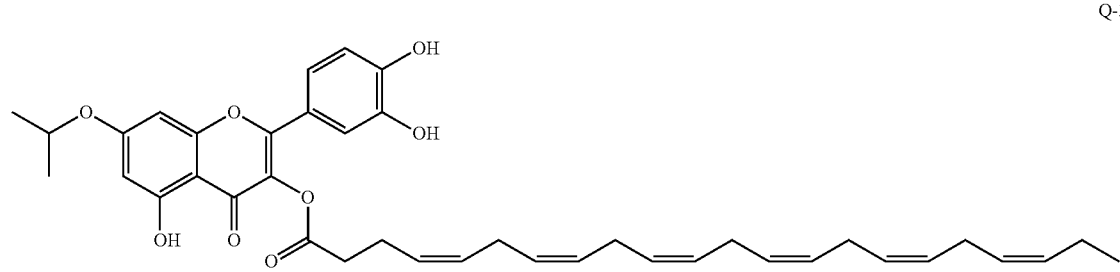
Q-3LA-7OiP
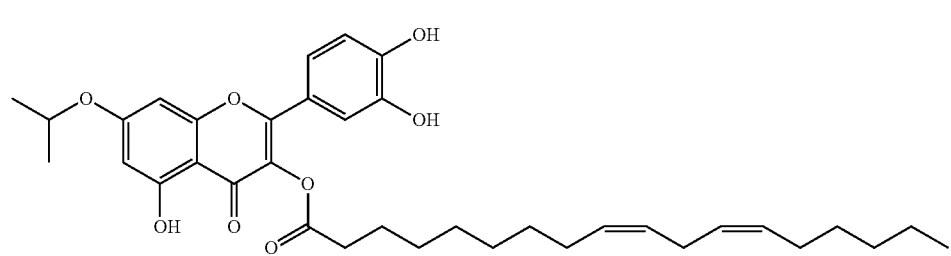

-continued

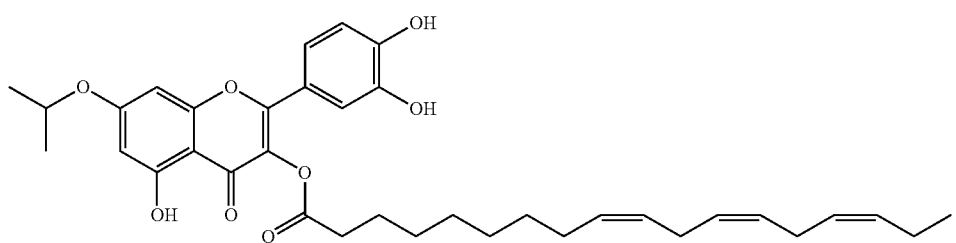
Q-3ALA-7OiP

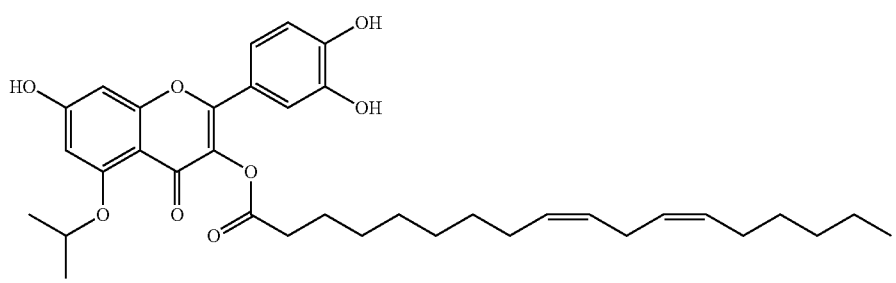
Q-3LA-5OiP

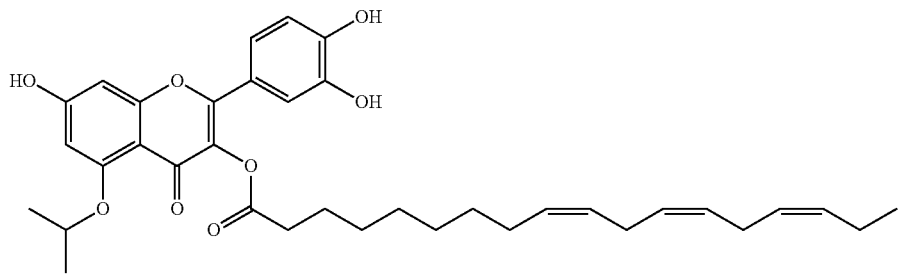
Q-3ALA-5OiP

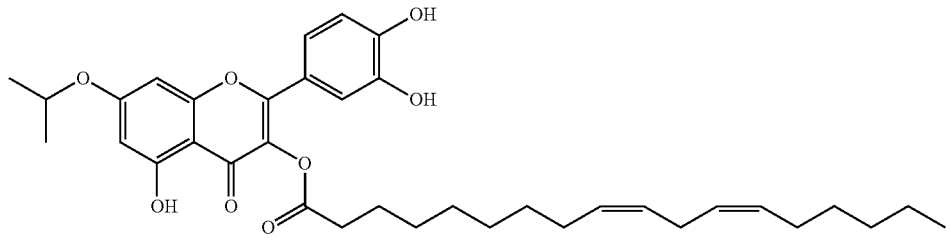
Q-3LA-7OiP

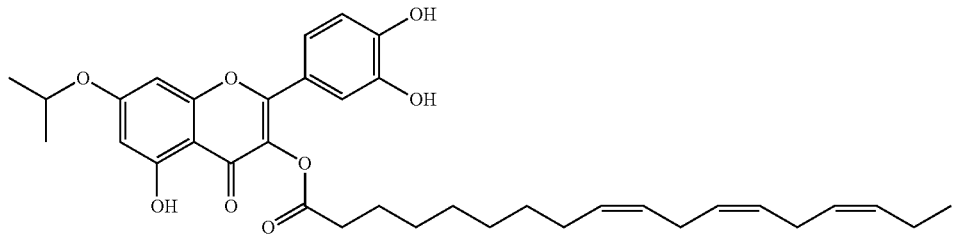
Q-3ALA-7OiP

10. The method according to claim 1, wherein the disease or disorder involving both carbonyl and oxidative stresses is selected from the group consisting of inflammatory and infectious diseases, cardiovascular diseases, metabolic diseases, cancer, infertility, retinal pathologies, neuromuscular and muscular diseases, psychiatric diseases and neurodegenerative diseases, or food oxidation, ageing or sporting activities.

11. The method according to claim 10, wherein the retinal pathology is selected from retinal aging-associated pathologies, and retinal genetic pathologies.

12. The method according to claim 10, wherein the neurodegenerative disease is selected from Alzheimer's disease and Parkinson's disease.

13. The method according to claim 1, wherein the compound is selected from the group consisting of:

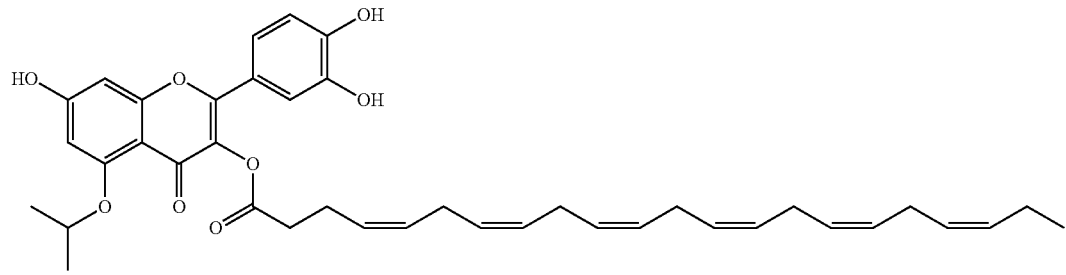

Q-3DHA-5OiP

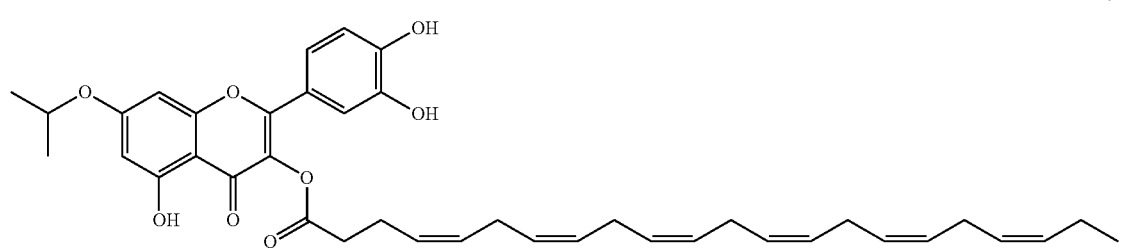

Q-3DHA-7OiP

14. A non-therapeutic method for preventing a non-pathologic disorder involving both carbonyl and oxidative stresses and selected in the group consisting of food oxidation, ageing and sporting activities, comprising the administration to a subject in need thereof of compound of formula (I):

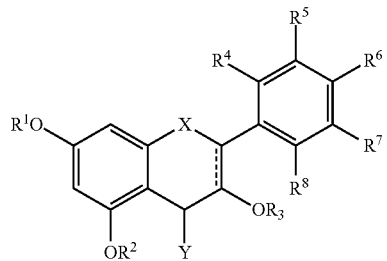

are as defined in claim 1,
or its pharmaceutically acceptable salts, racemates, diastereoisomers, enantiomers or mixtures thereof.

15. A compound of formula (II):

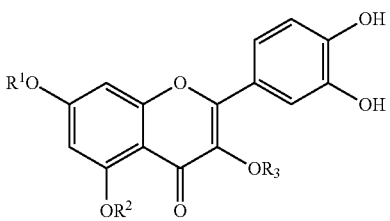

wherein
$R^1$ and $R^2$ are different and are selected from the group consisting of H or ($C_1$-$C_6$) alkyl, and
$R_3$ is selected from the group consisting of —CO—($C_{11}$-$C_{21}$)alkyl or —CO—($C_{11}$-$C_{21}$)alkenyl.

16. The compound of claim 15, wherein the compound is selected from the group consisting of:

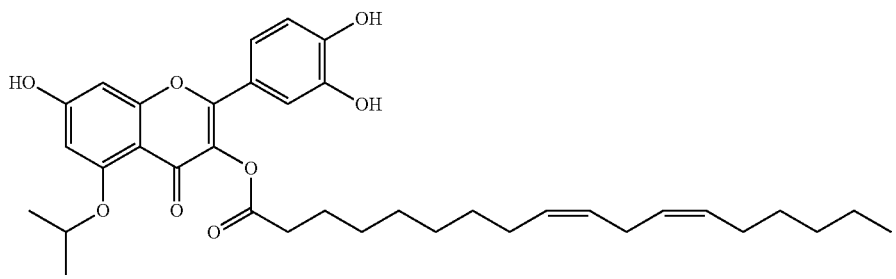

Q-3LA-5OiP

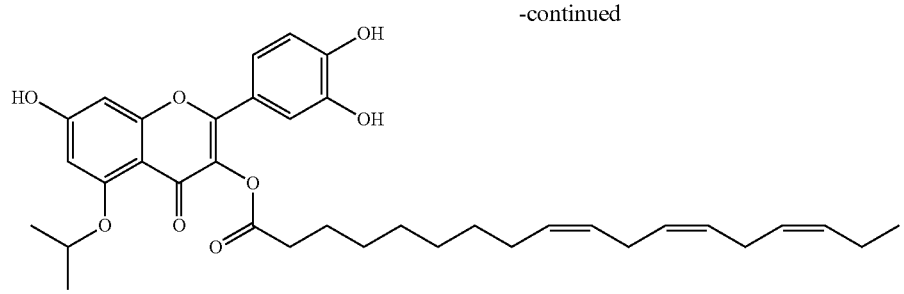
Q-3ALA-5OiP
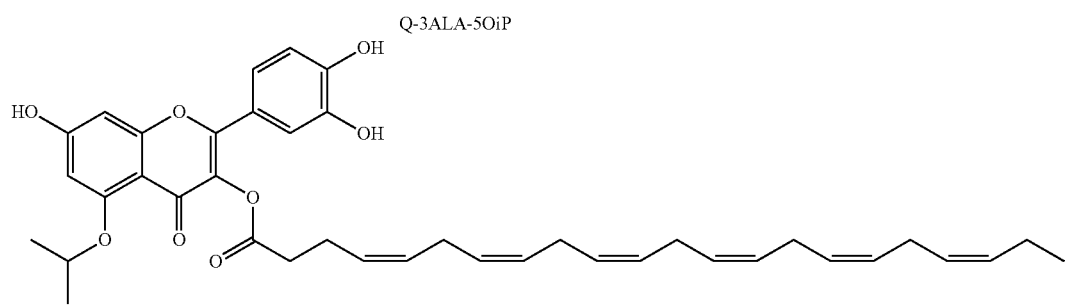
Q-3DHA-5OiP
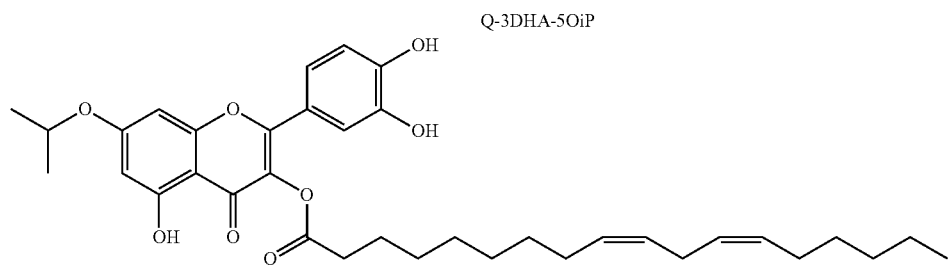
Q-3LA-7OiP
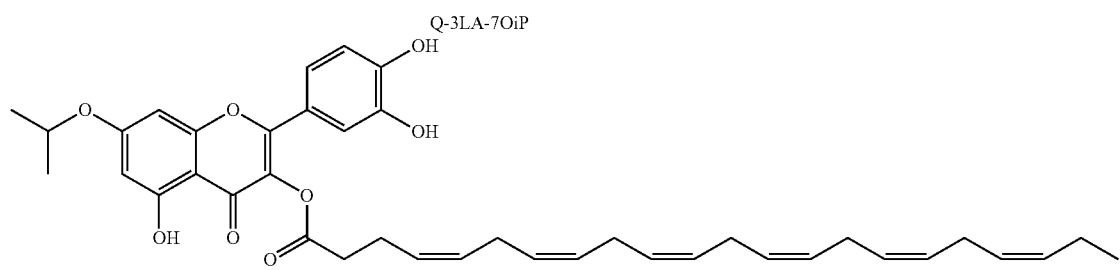
Q-3DHA-7OiP
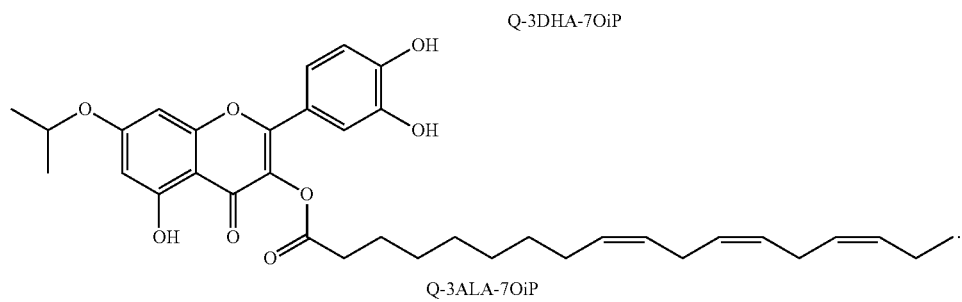
Q-3ALA-7OiP
17. A composition comprising, in a cosmetic, food-grade or pharmaceutically acceptable vehicle, at least one compound as defined in claim 15.
18. The composition according to claim 17, which is a cosmetic, nutritional or pharmaceutical composition.
* * * * *